US009751928B2

(12) United States Patent
Schmitt et al.

(10) Patent No.: US 9,751,928 B2

(45) Date of Patent: Sep. 5, 2017

(54) ENHANCED AFFINITY T CELL RECEPTORS AND METHODS FOR MAKING THE SAME

(71) Applicant: Fred Hutchinson Cancer Research Center, Seattle, WA (US)

(72) Inventors: Thomas M. Schmitt, Seattle, WA (US); Philip D. Greenberg, Mercer Island, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 83 days.

(21) Appl. No.: 14/398,206

(22) PCT Filed: May 2, 2013

(86) PCT No.: PCT/US2013/039316

§ 371 (c)(1),
(2) Date: Oct. 31, 2014

(87) PCT Pub. No.: WO2013/166321

PCT Pub. Date: Nov. 7, 2013

(65) Prior Publication Data

US 2015/0118208 A1 Apr. 30, 2015

Related U.S. Application Data

(60) Provisional application No. 61/642,358, filed on May 3, 2012.

(51) Int. Cl.

| | |
|---|---|
| ***C07K 14/725*** | (2006.01) |
| ***A61K 38/17*** | (2006.01) |
| ***C12N 5/078*** | (2010.01) |
| ***C12N 5/0783*** | (2010.01) |
| ***G01N 33/569*** | (2006.01) |
| ***A61K 39/00*** | (2006.01) |
| ***A61K 35/17*** | (2015.01) |

(52) U.S. Cl.

CPC .......... *C07K 14/7051* (2013.01); *A61K 35/17* (2013.01); *A61K 38/1774* (2013.01); *A61K 39/0011* (2013.01); *C12N 5/065* (2013.01); *C12N 5/0636* (2013.01); *G01N 33/56966* (2013.01); *A61K 2039/5156* (2013.01); *A61K 2039/5158* (2013.01); *C12N 2501/42* (2013.01); *C12N 2502/1394* (2013.01); *C12N 2502/99* (2013.01); *G01N 2333/7051* (2013.01)

(58) Field of Classification Search

None

See application file for complete search history.

(56) References Cited

U.S. PATENT DOCUMENTS

| | | | |
|---|---|---|---|
| 6,040,177 | A | 3/2000 | Riddell et al. |
| 6,759,243 | B2 | 7/2004 | Kranz et al. |
| 7,575,925 | B2 | 8/2009 | Schmitt et al. |
| 8,119,772 | B2 | 2/2012 | Yang et al. |
| 2002/0001826 | A1 | 1/2002 | Wager et al. |
| 2009/0217403 | A1 | 8/2009 | Spits |

OTHER PUBLICATIONS

Ha, et al (2010) "Transplantation of mouse HSCs genetically modified to express a CD4-restricted TCR results in long term immunity that destroys tumors and initiates spontaneous autoimmunity", The Journal of Clinical Investigation, 120(12): 4273-88.*

Holmes, et al. (2009) "The OP9-DL1 System: Generation of T-Lymphocytes from Embryonic or Hematopoietic Stem Cells In Vitro", Cold Spring Harbor Protocols, 4(2): 1-12.*

Mohtashami, et al. (2013) "Induction of T-cell development by Delta-like 4-expressing fibroblasts", International Immunology, 25(10): 601-611.*

Chervin et al., "Engineering higher affinity T cell receptors using a T cell display system," *Journal of Immunological Methods 339*:175-184 (2008).

Moysey et al., "Directed evolution of human T-cell receptors with picomolar affinities by phage display," *Nature Biotechnology 23*(3):349-354 (Mar. 2005).

Weber et al., "Class II-restricted T cell receptor engineered in vitro for higher affinity retains peptide specificity and function," *PNAS 102*(52):19033-19038 (Dec. 27, 2005).

Aggen, "Engineering Human Single-Chain T Cell Receptors," Dissertation, submitted to the University of Illinois at Urbana-Champaign, 2010, 181 pages.

Akatsuka et al., "Efficient cloning and expression of HLA class I cDNA in human B-lymphoblastoid cell lines," *Tissue Antigens* 59:502-511, 2002.

Alli et al., "Rational Design of T Cell Receptors with Enhanced Sensitivity for Antigen," *PLoS One 6*(3):e18027, 2011, 11 pages.

Altman et al., "Phenotypic Analysis of Antigen-Specific T Lymphocytes," *Science 274*(5284):94-96, 1996.

Berger et al., "Adoptive transfer of effector CD8+ T cells derived from central memory cells establishes persistent T cell memory in primates," *The Journal of Clinical Investigation 118*(1):294-305, 2008.

Birkholz et al., "A fast and robust method to clone and functionally validate T-cell receptors," *Journal of Immunological Methods 346*:45-54, 2009.

Borràs et al., "Findings on T cell specificity revealed by synthetic combinatorial libraries," *Journal of Immunological Methods 267*:79-97, 2002.

Brusko et al., "Human regulatory T cells: role in autoimmune disease and therapeutic opportunities," *Immunological Reviews 223*:371-390, 2008.

Dossett et al., "Adoptive Immunotherapy of Disseminated Leukemia With TCR-transduced, CD8+ T Cells Expressing a Known Endogenous TCR," *Molecular Therapy 17*(4):742-749, 2009.

(Continued)

*Primary Examiner* — Robert M Kelly

(74) *Attorney, Agent, or Firm* — Seed IP Law Group LLP

(57) ABSTRACT

The present disclosure provides methods for generating enhanced affinity T cell receptors by agonist selection of hematopoietic progenitor cells expressing an antigen specific TCRα cultured with stromal cells expressing Delta-like-1 or Delta-like-4, compositions prepared from such methods, and uses of thereof.

20 Claims, 11 Drawing Sheets

(56) References Cited

OTHER PUBLICATIONS

Egawa et al., "Lineage Diversion of T Cell Receptor Transgenic Thymocytes Revealed by Lineage Fate Mapping," *PLoS One 1*:e1512, 2008, 7 pages.
Engels et al., "Retroviral Vectors for High-Level Transgene Expression in T Lymphocytes," *Human Gene Therapy 14*:1155-1168, 2003.
Frecha et al., "Advances in the Field of Lentivector-based Transduction of T and B Lymphocytes for Gene Therapy," *Molecular Therapy 18*(10):1748-1757, 2010.
Fujio et al., "Gene Therapy of Arthritis With TCR Isolated from the Inflamed Paw," the Journal of Immunology 177(11):8140-8147, 2006.
Gaiger et al., "Immunity to WT1 in the animal model and in patients with acute myeloid leukemia," *Blood 96*(4): 1480-1489, 2000.
Garcia et al., "Kinetics and thermodynamics of T cell receptor-autoantigen interactions in murine experimental autoimmune encephalomyelitis," *PNAS 98*(12):6818-6823, 2001.
Hiemstra et al., "Antigen arrays in T cell immunology," *Current Opinion in Immunology 12*(1):80-84, 2000.
Hinrichs et al., "Adoptively transferred effector cells derived from naive rather than central memory CD8+ T cells mediate superior antitumor immunity," *PNAS 106*(41):17469-17474, 2009.
Hogquist et al., "T Cell Receptor Antagonist Peptides Induce Positive Selection," *Cell 76*:17-27, 1994.
Hung et al., "Control of mesothelin-expressing ovarian cancer using adoptive transfer of mesothelin peptide-specific $CD8^+$ T cells," *Gene Ther. 14*(12):921-929, 2007. (18 pages).
Itoh et al., "Reproducible Establishment of Hemopoietic Supportive Stromal Cell Lines from Murine Bone Marrow," *Experimental Hematology 17*(2):145-153, 1989.
James et al., "Visualizing Antigen Specific CD4+ T Cells using MHC Class II Tetramers," *Journal of Visualized Experiments 25*: 2009, 5 pages.
Jun., "Adoptive T cell therapy for cancer in the clinic," *The Journal of Clinical Investigation 117*(6):1466-1476, 2007.
Kalergis et al., "A simplified procedure for the preparation of MHC / peptide tetramers: chemical biotinylation of an unpaired cysteine engineered at the C-terminus of MHC-I," *Journal of Immunological Methods 234*:61-70, 2000.
Kieback et al., "Enhanced T cell receptor gene therapy for cancer," *Expert Opin. Biol. Ther. 10*(5):749-762, 2010.
Kitchen et al., "Engineering Antigen-Specific T Cells from Genetically Modified Human Hematopoietic Stem Cells in Immunodeficient Mice," *PLoS One 4*(12):e8208, 2009, 9 pages.
Kodama et al., "Involvement of the *c-kit* receptor in the adhesion of hematopoietic stem cells to stromal cells," *Experimental Hematology 22*:979-984, 1994.
Kuball et al., "Increasing functional avidity of TCR-redirected T cells by removing defined *N*-glycosylation sites in the TCR constant domain," *J. Exp. Med. 206*(2):463-475, 2009.
Kurokawa et al., "Paired cloning of the T cell receptor α and β genes from a single T cell without the establishment of a T cell clone," *Clinical and Experimental Immunology 123*(2):340-345, 2001.
La Motte-Mohs et al., "Induction of T-cell development from human cord blood hematopoietic stem cells by Delta-like 1 in vitro," *Blood 105*(4):1431-1439, 2005.
Laugel et al., "Different T Cell Receptor Affinity Thresholds and CD8 Coreceptor Dependence Govern Cytotoxic T Lymphocyte Activation and Tetramer Binding Properties," *The Journal of Biological Chemistry 282*(33):23799-237810, 2007.
Letourneur et al., "Derivation of a T cell hybridoma variant deprived of functional T cell receptor α and β chain transcripts reveals a nonfunctional α-mRNA of BW5147 origin," *Eur. J. Immunol. 19*:2269-2274, 1989.
Luo et al., "Development of genetically engineered $CD4^+$ and $CD8^+$ T cells expressing TCRs specific for a *M. tuberculosis* 38-kDa antigen," *J Mol Med 89*:903-913, 2011.
Molloy et al., "Soluble T cell receptors: novel immunotherapies," *Current Opinion in Pharmacology 5*:438-443, 2005.
Morgan et al., "Cancer Regression in Patients After Transfer of Genetically Engineered Lymphocytes," *Science 314*(5796):126-129, 2006. (10 pages).
Pennington et al., "γδ T cell development—having the strength to get there," *Current Opinion in Immunology 17*:108-115, 2005.
Pouw et al., "Gene transfer of human TCR in primary murine T cells is improved by pseudo-typing with amphotropic and ecotropic envelopes," *The Journal of Gene Medicine 9*:561-570, 2007.
Richman et al., "Display, engineering, and applications of antigen-specific T cell receptors," *Biomolecular Engineering* 24:361-373, 2007.
Rossi et al., "Genetic therapies against HIV," *Nature Biotechnology 25*(12):1444-1455, 2007.
Sandberg et al., "Human T-cell lines with well-defined T-cell receptor gene rearrangements as controls for the BIOMED-2 multiplex polymerase chain reaction tubes," *Leukemia 21*(2):230-237, 2007.
Scholten et al., "Codon modification of T cell receptors allows enhanced functional expression in transgenic human T cells," *Clinical Immunology 119*:135-145, 2006.
Schmid et al., "Evidence for a TCR Affinity Threshold Delimiting Maximal CD8 T Cell Function," *The Journal of Immunology 184*(9):4936-4946, 2010.
Schmitt et al., "Induction of T Cell Development from Hematopoietic Progenitor Cells by Delta-like-1 In Vitro," *Immunity 17*(6):749-756, 2002.
Schmitt et al., "Induction of T cell development and establishment of T cell competence from embryonic stem cells differentiated in vitro," *Nature Immunology 5*(4):410-417, 2004.
Schmitt et al., "T Cell Receptor Gene Therapy for Cancer," *Human Gene Therapy 20*:1240-1248, 2009.
Szymczak et al., "Correction of multi-gene deficiency in vivo using a single 'self-cleaving' 2A peptide-based retroviral vector," *Nature Biotechnology 22*(5):589-594, 2004.
Udyavar et al., "Subtle affinity-enhancing mutations in a MOG-specific TCR alter specificity and generate new self-reactivity," *J Immunol. 182*(7):4439-4447, 2009. (19 pages).
Verhoeyen et al., "Lentiviral Vector Gene Transfer into Human T Cells," *Methods in Molecular Biology 506*:97-114, 2009.
Wälchli et al., "A Practical Approach to T-Cell Receptor Cloning and Expression," *PLoS One 6*(11):e27930 2011, 11 pages.
Xu et al., "MHC/peptide tetramer-based studies of T cell function," *Journal of Immunological Methods 268*:21-28, 2002.
Zhang et al., "Transduction of Human T Cells with a Novel T-Cell Receptor Confers Anti-HCV Reactivity," *PLoS Pathogens 6*(7):e1001018, 2010, 13 pages.
Zhao et al., "High-Affinity TCRs Generated by Phage Display Provide $CD4^+$ T Cells with the Ability to Recognize and Kill Tumor Cell Lines," *J Immunol. 179*(9):5845-5854, 2007. (19 pages).
Zhao et al., "Primary Human Lymphocytes Transduced with NY-ESO-1 Antigen-Specific TCR Genes Recognize and Kill Diverse Human Tumor Cell Lines," *J Immunol. 174*(7):4415-4423, 2005. (25 pages).

* cited by examiner

| | 104 | 105 | 106 | 107 | 108 | 109 | 110 | 111 | 112 | 113 | 114 | 115 | 116 | 117 | 118 | |
|---|---|---|---|---|---|---|---|---|---|---|---|---|---|---|---|---|
| 3Dβ | C | A | S | S | P | G | L | G | G | S | Y | E | Q | Y | F | SEQ ID. NO: 32 |
| | tgt | gcc | agc | agc | cct | gga | ctg | ggg | gga | tcc | tat | gaa | cag | tac | ttc | SEQ ID. NO: 33 |
| Vβ10 clone#1 | C | A | S | S | Q | G | L | G | S | S | Y | E | Q | Y | F | SEQ ID. NO: 34 |
| | tgt | gcc | agc | agc | cag | gga | ctg | ggg | agc | tcc | tat | gaa | cag | tac | ttc | SEQ ID. NO: 35 |
| Vβ10 clone#2 | C | A | S | S | Y | I | L | | G | A | Y | E | Q | Y | F | SEQ ID. NO: 36 |
| | tgt | gcc | agc | agc | tat | ata | ctg | ... | ggg | gcc | tat | gaa | cag | tac | ttc | SEQ ID. NO: 37 |
| Vβ10 clone#3 | C | A | S | S | S | W | T | | | V | Y | E | Q | Y | F | SEQ ID. NO: 38 |
| | tgt | gcc | agc | agc | tcc | tgg | aca | ... | ... | gtc | tat | gaa | cag | tac | ttc | SEQ ID. NO: 39 |
| Vβ10 clone#4 | C | A | S | S | W | T | G | A | N | T | G | Q | L | Y | F | SEQ ID. NO: 40 |
| | tgt | gcc | agc | agc | tgg | aca | ggg | gca | aac | acc | ggg | cag | ctc | tac | ttt | SEQ ID. NO: 41 |

*Fig. 4B*

ENHANCED AFFINITY T CELL RECEPTORS AND METHODS FOR MAKING THE SAME

CROSS REFERENCE TO RELATED APPLICATION

This application claims the benefit under 35 U.S.C. §119 (e) to U.S. Provisional Application No. 61/642,358 filed on May 3, 2012, which application is incorporated by reference herein in its entirety.

STATEMENT OF GOVERNMENT INTEREST

This invention was made with government support under CA018029 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_412WO_SEQUENCE_LISTING.TXT. The text file is 129KB, was created on May 2, 2013 and is being submitted electronically via EFS-Web.

BACKGROUND

Technical Field

The present disclosure relates to enhanced affinity T cell receptors (TCRs) and, more particularly, to using agonist selection of hematopoietic progenitor cells expressing an antigen specific TCRα to generate enhanced affinity TCRs, and to uses thereof.

Description of the Related Art

TCR gene therapy is an emerging treatment approach that can overcome many of the obstacles associated with conventional T cell adoptive immunotherapy, such as the extensive time and labor required to isolate, characterize, and expand tumor antigen-specific T cell clones (Schmitt, Ragnarsson, & Greenberg, 2009, Hum. Gene Ther. 20:1240-1248). Further benefits of gene therapy include the ability to utilize defined populations of T cells capable of long-term persistence in vivo (Berger et al., 2008, J. Clin. Invest. 118:294-305; Hinrichs et al., 2009, Proc. Natl. Acad. Sci. USA 106:17469-17474). Such T cells can be transduced with genes encoding well-characterized TCRs that have a high affinity for tumor antigens, thereby increasing the likelihood of mediating an antitumor effect. Indeed, a recent report of therapy targeting advanced B cell leukemia with genetically modified T cells expressing a high affinity chimeric receptor targeting a self/tumor-antigen has highlighted the potential of using engineered high avidity T cells for the treatment of leukemia (Kalos et al., 2011, Sci. Transl. Med. 3:95ra73). However, since most tumor antigens targeted by T cell immunotherapy are over-expressed self-proteins, high affinity T cells specific for these antigens are generally subject to negative selection in the thymus. Therefore, one significant limitation of T cell based immunotherapies in general is the limited availability of T cells expressing an endogenous TCR with sufficiently high affinity for non-mutated tumor antigens.

Several strategies have been developed to enhance the affinity of TCRs intended for use in TCR gene therapy (Richman & Kranz, 2007, Biomol. Eng. 24:361-373; Udyavar et al., 2009, J. Immunol. 182:4439-4447; Zhao et al., 2007, J. Immunol. 179:5845-5854). These approaches generally entail the generation of libraries of TCR mutants that have undergone rounds of mutagenesis and subsequent screening for mutations that confer higher affinity for the target peptide/MHC ligand. Mutations are generally made in the CDR regions that are known to interact with peptide/MHC. CDR1 and CDR2 regions predominantly make contact with the MHC molecule, while the hypervariable CDR3 region primarily contacts the peptide (Wucherpfennig et al., 2010, Cold Spring Harbor Perspectives in Biology 2:a005140-a005140). Site-directed mutagenesis strategies generally target selected portions of all three of these regions, but still are not always successful in generating a higher affinity variant, and the improvements are limited to changes only in the specifically targeted regions. Moreover, mutations introduced into the MHC contact residues have the risk of potentially increasing the affinity of the TCR for MHC while decreasing the overall specificity of the receptor for its cognate peptide. Ideally, most mutations introduced to enhance the affinity of a TCR would be restricted to the CDR3 region for this reason. However, current methodologies are limited in the capacity to generate CDR3 diversity, because site-directed mutagenesis is constrained by the original length of the CDR3 region.

Given the difficulty of isolating high affinity T cells that recognize relevant tumor associated antigens, there is a continuing need for alternative methods for generating enhanced affinity TCRs.

BRIEF SUMMARY

In one aspect, the present disclosure provides a method for generating an enhanced affinity TCR comprising: a) contacting hematopoietic progenitor cells with stromal cells and a peptide antigen, under conditions and for a time sufficient to induce differentiation of the hematopoietic progenitor cells into DN TCRαβ[+] thymocytes, wherein the hematopoietic progenitor cells comprise a non-endogenous nucleic acid sequence encoding a TCRα chain from a parent TCR specific for the peptide antigen, and wherein the stromal cells comprise a non-endogenous nucleic acid sequence encoding Delta-like-1 or Delta-like-4 and a nucleic acid sequence encoding an MHC molecule; b) isolating nucleic acid sequences encoding the various TCRβ chains from the DN TCRαβ[+] thymocytes and introducing the nucleic acid sequences encoding the TCRβ chains into cells that are capable of expressing a TCR on the cell surface and comprising the nucleic acid sequence encoding the TCRα chain from step a); and identifying enhanced affinity TCR (e.g., by detecting or selecting high affinity TCRαβ candidate by an MHC tetramer assay, and then measuring binding affinity as compared to a parent TCRαβ).

In further aspects, enhanced affinity TCRs generated by methods disclosed herein are provided, which may be cell-bound or in soluble form, and may further be codon optimized to enhance expression in T cells.

In still further aspects, enhanced affinity TCRs of the present disclosure may be used to treat a disease (such as cancer, infectious disease, or autoimmune disease) in a subject by administering a composition comprising the enhanced affinity TCRs. In further embodiments, enhanced affinity TCRs of the instant disclosure may be used in diagnostic methods or imaging methods, including these methods used in relation to the indications or conditions identified herein.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 4A-C: The retroviral TCRβ library was used to transduce $CD8^{+}3\ D\alpha^{+}58^{-/-}$ cells. (A) Transduced cells were initially sorted on GFP expression only (data not shown), followed by two additional sorts on GFP and high MHC-WT1 peptide tetramer expression as indicated. Sorted $58^{-/-}$ cells were also analyzed for staining with the non-specific, but MHC H-2 Db-peptide tetramer specific for GP33 as a control for non-specific tetramer binding. (B) Sequence analysis of isolated TCRβ chains. (C) Four candidate TCRβ chains were identified by sequence analysis, and were transferred back into MigR1-attR retroviral vector. Retroviral supernatant was generated, and used to transduce $CD8^{+}$ $3D\alpha^{+}58^{-/-}$ cells.

DETAILED DESCRIPTION

Figure 1A:
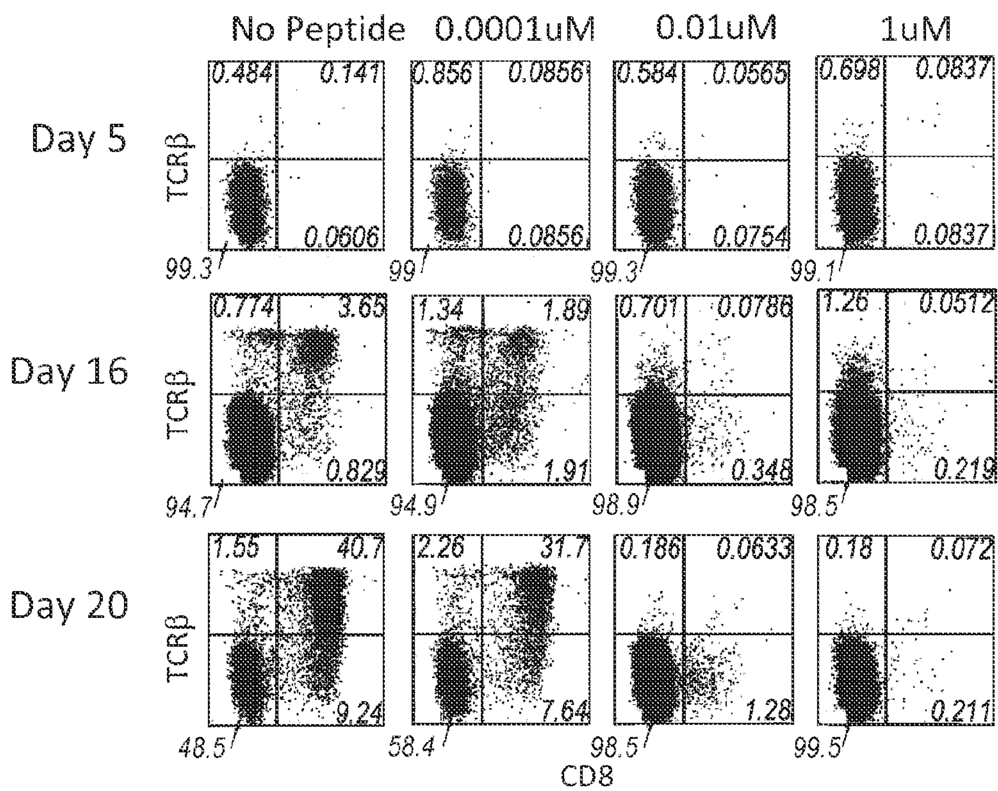
FIGS. 1A-D: Thymocytes from OT-1 transgenic mice were sorted for $TCR\beta^{-}TCR\gamma\delta^{-}CD4^{-}CD8^{-}CD117^{+}CD44^{+}$ DN1 and DN2 progenitor cells and cultured on OP9-DL1 cells expressing MHC Class I H-2 Kb molecule for 20 days in the presence of various concentrations of ovalbumin SIINFEKL peptide (SEQ ID NO:1) as indicated. (A, B, C) Cultures were analyzed by flow cytometry at the timepoints indicated. (D) Total cellularity of each culture was determined on day 20 of culture.

The instant disclosure provides methods and compositions for generating enhanced or high affinity TCRs, in which the TCRα chain from an antigen-specific TCR is used to select de novo generated TCRβ chains that pair with an antigen-specific TCRα chain during T cell development in vitro, to form new, enhanced affinity receptors that can advantageously drive T cell maturation independent of negative selection through a novel selection process in order to target an antigen of interest.

In one aspect, the present disclosure provides a method for generating an enhanced affinity T cell receptor (TCR) by culturing hematopoietic progenitor cells (containing a non-endogenous nucleic acid sequence encoding an antigen specific TCRα chain) with stromal cells (containing a non-endogenous nucleic acid sequence encoding Delta-like-1 or Delta-like-4 and a nucleic acid sequence encoding an MHC molecule) in the presence of a peptide antigen, which will induce differentiation of the hematopoietic progenitor cells into DN $TCR\alpha\beta^{+}$ thymocytes. Then, nucleic acid sequences encoding various TCRβ chains from the DN $TCR\alpha\beta^{+}$ thymocytes are isolated and introduced into cells that are capable of expressing a TCR on the cell surface and also express the TCRα chain noted above. Finally, an enhanced affinity TCR is identified by comparing the binding affinity of candidate TCRαβ with the parent TCRαβ.

Additionally, this disclosure provides enhanced affinity TCRs generated using such methods, as well as compositions and methods for using the enhanced affinity TCRs of the present disclosure in various therapeutic applications, including the treatment of a disease in subject (e.g., cancer, infectious disease, autoimmune disease).

Prior to setting forth this disclosure in more detail, it may be helpful to an understanding thereof to provide definitions of certain terms to be used herein. Additional definitions are set forth throughout this disclosure.

In the present description, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

"T cell receptor" (TCR) refers to a molecule found on the surface of T cells (or T lymphocytes) that, in association with CD3, is generally responsible for recognizing antigens bound to major histocompatibility complex (MHC) molecules. The TCR has a disulfide-linked heterodimer of the highly variable α and β chains (also known as TCRα and TCRβ, respectively) in most T cells. In a small subset of T cells, the TCR is made up of a heterodimer of variable γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease,* 3rd Ed., Current Biology Publications, p. 4:33, 1997). TCR as used in the present disclosure may be from various animal species, including human, mouse, rat, or other mammals. A TCR may be cell-bound or in soluble form.

TCRs and binding domains thereof of this disclosure can be "immunospecific" or capable of binding to a desired degree, including "specifically or selectively binding" a target while not significantly binding other components present in a test sample, if they bind a target molecule with an affinity or $K_a$ (i.e., an equilibrium association constant of a particular binding interaction with units of 1/M) of, for example, greater than or equal to about $10^5$ $M^{-1}$, $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains refers to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater. Alternatively, affinity may be defined as an equilibrium dissociation constant ($K_d$) of a particular binding interaction with units of M (e.g., $10^{-5}$ M to $10^{-13}$ M). Affinities of TCRs and binding domain polypeptides according to the present disclosure can be readily determined using conventional techniques (see, e.g., Scatchard et al. (1949) Ann. N.Y. Acad. Sci. 51:660; and U.S. Pat. Nos. 5,283,173; 5,468,614, Biacore® analysis, or the equivalent). Therefore, "enhanced affinity T cell receptor" (enhanced affinity TCR) refers to a selected or engineered TCR with stronger binding to a target antigen than the wild type (or parent) TCR. Enhanced affinity may be indicated by a TCR with a Ka (equilibrium association constant) for the target antigen higher than that of the wild type (also called parent or original) TCR, a TCR with a $K_d$ (dissociation constant) for the target antigen less than that of the wild type (also called parent or original) TCR, or with an off-rate ($K_{off}$) for the target antigen less than that of the wild type (or parent) TCR.

"Major histocompatibility complex molecules" (MHC molecules) refer to glycoproteins that deliver peptide antigens to a cell surface. MHC class 1 molecules are heterodimers consisting of a membrane spanning a chain (with three α domains) and a non-covalently associated β2 microglobulin. MHC class II molecules are composed of two transmembrane glycoproteins, α and β, both of which span the membrane. Each chain has two domains. MHC class 1 molecules deliver peptides originating in the cytosol to the cell surface, where peptide:MHC complex is recognized by $CD8^+$ T cells. MHC class II molecules deliver peptides originating in the vesicular system to the cell surface, where they are recognized by $CD4^+$ T cells. An MHC molecule may be from various animal species, including human, mouse, rat, or other mammals.

A "hematopoietic progenitor cell" is a cell derived from hematopoietic stem cells or fetal tissue that is capable of further differentiation into mature cells types (e.g., cells of the T cell lineage). In a particular embodiment, $CD24^{lo}$ $Lin^-$ $CD117^+$ hematopoietic progenitor cells are used. As defined herein, hematopoietic progenitor cells may include embryonic stem cells, which are capable of further differentiation to cells of the T cell lineage. Hematopoietic progenitor cells may be from various animal species, including human, mouse, rat, or other mammals.

A "thymocyte progenitor cell" or "thymocyte" is a hematopoietic progenitor cell present in the thymus.

"Hematopoietic stem cells" refer to undifferentiated hematopoietic cells that are capable of essentially unlimited propagation either in vivo or ex vivo and capable of differentiation to other cell types including cells of the T cell lineage. Hematopoietic stem cells may be isolated from, for example, fetal liver, bone marrow, and cord blood.

"Cells of T cell lineage" refer to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g., $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 linage commitment; thymocyte progenitor cells that are $CD4^+CD8^+$ double positive; single positive $CD4^+$ or $CD8^+$; TCRαβ or TCR γδ; or mature and functional or activated T cells.

"Stromal cells" are connective tissue cells of any organ. In a particular embodiment, the stromal cells are bone marrow stromal cells. Examples of stromal cell lines that can be engineered to express DLL1 or DLL4 include the mouse stromal cell line MS5 (Itoh, et al., Exp. Hematol. 1989, 17:145-153) and S17, and the human stromal cell lines HGS2.11, HGS2.52, HGS.18, HGS3.30, HGS3.65, HGS.3.66, HGS3.103, and HGS3.114 (available from Human Genome Sciences Inc., MD, see US Published Application 20020001826). In a particular embodiment, OP9 cells (Kodama et al., 1994, Exp. Hematol. 22:979-984; available from RIKEN cell depository) are used. OP9 cells expressing DLL1 and DLL4 have been previously described (see, e.g., Schmitt et al., 2002, Immunity:17:749-756; U.S. Pat. No. 7,575,925)

"Double negative TCRαβ thymocytes" (DN TCRαβ thymocytes) refer to a population of thymocytes that do not express the CD4 and CD8 co-receptors, but do express TCRα and β chains.

"Peptide antigen" refers to an amino acid sequence, ranging from about 7 amino acids to about 25 amino acids in length that is specifically recognized by a TCR, or binding domains thereof, as an antigen, and which may be derived from or based on a fragment of a longer target biological molecule (e.g., polypeptide, protein) or derivative thereof. An antigen may be expressed on a cell surface, within a cell, or as an integral membrane protein. An antigen may be a host-derived (e.g., tumor antigen, autoimmune antigen) or have an exogenous origin (e.g., bacterial, viral).

"Nucleic acid sequence", or polynucleotides, may be in the form of RNA or DNA, which includes cDNA, genomic DNA, and synthetic DNA. The nucleic acid sequence may be double stranded or single stranded, and if single stranded, may be the coding strand or non-coding (anti-sense strand). A coding sequence may be identical to the coding sequence known in the art or may be a different coding sequence, which, as the result of the redundancy or degeneracy of the genetic code, or by splicing, encodes the same polypeptide.

"Non-endogenous" refers to a molecule (e.g., nucleic acid sequence) that is not present in the host cell(s)/sample into which a molecule is introduced, for example, recombinantly introduced. A non-endogenous molecule may be from the same species or a different species.

Notch ligands "Delta-like-1" (DL1 or DLL1) and "Delta-like-4" (DL4 or DLL4) are homologs of the Notch Delta ligand and are members of the delta/serrate/jagged protein family. They play a role in mediating cell fate decisions during hematopoiesis and may play a role in cell-to-cell communication. Exemplary Delta-like-1 sequences include Genbank Accession No. NM_005618.3 (SEQ ID NO:3) and NP_005609.3 (SEQ ID NO:4) (*Homo sapiens* transcript and protein sequences, respectively) and Genbank Accession No. NM_007865.3 (SEQ ID NO:5) and NP_031891.2 (SEQ ID NO:6) (*Mus musculus* transcript and protein sequences, respectively). Exemplary Delta-like-4 sequences include Genbank Accession No. NM_019074.3 (SEQ ID NO:7) and NP_061947.1 (SEQ ID NO:8) (*Homo sapiens* transcript and protein sequences, respectively) and Genbank Accession No. NM_019454.3 (SEQ ID NO:9) and NP_062327.2 (SEQ ID NO:10) (*Mus musculus* transcript and protein sequences, respectively). Notch ligands are commercially available or can be produced by standard recombinant DNA techniques and purified to various degrees.

"Embryonic stem cells" or "ES cells" or "ESCs" refer to undifferentiated embryonic stem cells that have the ability to integrate into and become part of the germ line of a developing embryo. Embryonic stem cells are capable of differentiating into hematopoietic progenitor cells. Embryonic stem cells that are suitable for use herein include cells from the J1 ES cell line, 129J ES cell line, murine stem cell line D3 (American Type Culture Collection catalog #CRL 1934), the R1 or E14K cell lines derived from 129/Sv mice, cell lines derived from Balb/c and C57Bl/6 mice, and human embryonic stem cells (e.g. from WiCell Research Institute, WI; or ES cell International, Melbourne, Australia).

"WT1" refers to Wilm's tumor 1, a transcription factor that contains four zinc-finger motifs at the C-terminus and a proline/glutamine-rich DNA binding domain at the N-terminus. WT1 has an essential role in the normal development of the urogential system and is mutated in a small subset of patients with Wilm's tumors. High expression of WT1 has been observed in various cancers, including, breast cancer, ovarian cancer, acute leukemias, vascular neoplasms, melanomas, colon cancer, lung cancer, thyroid cancer, bone and soft tissue sarcoma, and esophageal cancer. Alternative splicing has been noted for WT1. Exemplary WT1 sequences include Genbank Accession Nos: NM_000378.4 (SEQ ID NO:11) (human transcript), NP_000369.3 (SEQ ID NO:12) (human protein); NM_024424.3 (SEQ ID NO:13) (human transcript), NP_077742.2 (SEQ ID NO:14) (human protein); NM_024426.4 (SEQ ID NO:15) (human transcript), NP_077744.3 (SEQ ID NO:16); NM_001198552.1 (SEQ ID NO:17), NP_001185481.1 (SEQ ID NO:18) (human protein); NM_001198551.1 (SEQ ID NO:19) (human transcript), NP_001185480.1 (SEQ ID NO:20) (human protein); NM_144783.2 (SEQ ID NO:21) (mouse transcript), and NP_659032.3 (SEQ ID NO:22) (mouse protein).

"Mesothelin" (MSLN) refers to a gene that encodes a precursor protein that is cleaved into two products, megakaryocyte potentiating factor and mesothelin. Megakaryocyte potentiation factor functions as a cytokine that can stimulate colony formation in bone marrow megakaryocytes. Mesothelian is a glycosylphosphatidylinositol-anchored cell-surface protein that may function as a cell adhesion protein. This protein is overexpressed in epithelial mesotheliomas, ovarian cancers and in specific squamous cell carcinomas. Alternative splicing results in multiple transcript variants. Exemplary mesothelin sequences include Genbank Accession Nos: NM_001177355.1 (SEQ ID NO:23), NP_001170826.1 (SEQ ID NO:24) (human transcript and pre-protein sequences, respectively); NM_005823.5 (SEQ ID NO:25), NP_005814.2 (SEQ ID NO:26)(human transcript and pre-protein sequences, respectively); NM_013404.4 (SEQ ID NO:27), NP_037536.2 (SEQ ID NO:28) (human transcript and pre-protein sequences, respectively); NM_018857.1 (SEQ ID NO:29), NP_061345.1 (SEQ ID NO:30) (mouse transcript and precursor protein sequences, respectively).

"MHC-peptide tetramer staining" refers to an assay used to detect antigen-specific T cells, which features a tetramer of MHC molecules, each comprising an identical peptide having an amino acid sequence that is cognate (e.g., identical or related to) at least one antigen, wherein the complex is capable of binding T cells specific for the cognate antigen. Each of the MHC molecules may be tagged with a biotin molecule. Biotinylated MHC/peptides are tetramerized by the addition of streptavidin, which is typically fluorescently labeled. The tetramer may be detected by flow cytometry via the fluorescent label. In certain embodiments, an MHC-peptide tetramer assay is used to detect or select high affinity TCRs of the instant disclosure.

Methods for Generating Enhanced Affinity TCRs

By way of background, during T cell development in the thymus, progenitor thymocytes are subjected to a number of TCR-mediated checkpoints. The first of these is termed β-selection, and occurs at double negative 3 (DN3) stage of murine T cell development. DN3 cells that produce a successful rearrangement at the Tcrb gene locus can express TCRβ protein at the cell surface paired with the invariant pre-Tα protein. This receptor is called the Pre-TCR, and it signals in a ligand-independent fashion to promote proliferation, differentiation of αβ lineage cells to the CD4CD8 double positive (DP) stage, and rearrangement at the Tcra gene locus (Boehmer et al., 1999, Curr. Opin. Immunol. 11:135-142). While the TCRα locus is inactive and closed to TCR gene rearrangements prior to β-selection, both the TCRγ and -δ loci also undergo rearrangements at the DN3 stage of development, and successful rearrangements at both these loci results in the expression of a mature γδ-TCR that can provide signals that drive differentiation towards the γδ T cell lineage-γδ T cells do not differentiate through a DP stage during development, and generally remain DN or CD8αα+. The αβ/γδ cell fate decision is determined by the strength of the TCR signal at this stage of development, as the developing T cell distinguishes between a pre-TCR signal and a γδ TCR signal by the stronger signal associated with the mature γδ TCR (Pennington, Silva-Santos, & Hayday, 2005, Curr. Opin. Immunol. 17:108-115). Interestingly, many αδ TCR transgenic mice have a large population of mature $CD24^-$ TCRαβ positive CD4/CD8 double negative (DN) cells in the thymus, which have been shown to represent "γδ wanna-be" cells that develop as a result of the stronger signal from the mature αβ transgenic TCR at the β-selection checkpoint (Egawa et al., 2000, PLOS One 3:1512).

Disclosed herein is a method for generating enhanced affinity TCRs, wherein ectopic expression of an antigen-specific TCRα chain prior to β-selection allows the development of T cells expressing a high affinity TCR for the same antigen when differentiated in the presence of the cognate antigen during in vitro T cell differentiation. Using this method, T cells expressing high affinity receptors bypass negative selection by adopting a DN $TCR\alpha\beta^+$ lineage fate in response to agonist signals at the DN3 stage of T cell development.

In certain embodiments, the present disclosure provides a method for generating an enhanced affinity TCR comprising: a) contacting hematopoietic progenitor cells with stromal cells and a peptide antigen, under conditions and for a time sufficient to induce differentiation of hematopoietic progenitor cells into DN TCRαβ+ thymocytes, wherein the hematopoietic progenitor cells comprise a non-endogenous nucleic acid sequence encoding a TCRα chain from a parent TCR specific for the peptide antigen, and wherein the stromal cells comprise a non-endogenous nucleic acid sequence encoding Delta-like-1 or Delta-like-4 and a nucleic acid sequence encoding an MHC molecule; b) isolating nucleic acid sequences encoding the various TCRβ chains from the DN TCRαβ+ thymocytes and introducing the nucleic acid sequences encoding the TCRβ chains into cells that are capable of expressing a TCR on the cell surface and comprise the nucleic acid sequence encoding the TCRα chain from step a); and identifying the enhanced affinity TCR (e.g., by detecting or selecting high affinity TCRαβ candidates by an MHC tetramer assay, and then measuring binding affinity as compared to a parent TCRαβ).

In certain embodiments, hematopoietic progenitor cells comprise thymocyte progenitor cells or embryonic stem cells. In other embodiments, hematopoietic progenitor cells are derived from fetal liver tissue. In other embodiments, hematopoietic progenitor cells comprise hematopoietic stem cells that are derived or originate from bone marrow, cord blood, or peripheral blood. In yet other embodiments, hematopoietic progenitor cells are derived from human, mouse, rat, or other mammals. In a particular embodiment, $CD24^{lo}$ $Lin^-$ $CD117^+$ thymocyte progenitor cells are used.

The hematopoietic progenitor cells have been modified to comprise a non-endogenous nucleic acid sequence encoding a TCRα chain from a parent TCR specific for the peptide antigen. In a specific embodiment, the TCRβ chain is also isolated from the parent TCR. Cloning of TCRα and β chains may be performed using standard molecular biology techniques that are known in the art. Methods for cloning TCR chains are known in the art (see, e.g., Walchli et al., 2011, PLoS ONE 6:e27930; Birkholz et al., 2009, J. Immunol. Methods 346:45-54; Kurokawa et al, 2001, Clin. Exp. Immunol. 123:340-345).

A "stromal cell" is a connective tissue cell of any organ. Stromal cells that may be used according to the invention include human and mouse stromal cells. Examples of stromal cell lines that can be engineered to express DL1 or DL4 include the mouse stromal cell line MS5 (Itoh, et al., Exp. Hematol. 1989, 17:145-153) and S17, and the human stromal cell lines HGS2.11, HGS2.52, HGS.18, HGS3.30, HGS3.65, HGS.3.66, HGS3.103, and HGS3.114 (available from Human Genome Sciences Inc., MD, see US Published Application 20020001826). In certain embodiments, stromal cells are bone marrow stromal cells. In further embodiments, OP9 cells are used.

In certain embodiments, stromal cells comprise non-endogenous nucleic acid sequences encoding DL1, such as human DL1. Exemplary Delta-like-1 sequences include Genbank Accession No. NM_005618.3 (SEQ ID NO:3) and NP_005609.3 (SEQ ID NO:4) (*Homo sapiens* transcript and protein sequences, respectively) and Genbank Accession No. NM_007865.3 (SEQ ID NO:5) and NP_031891.2 (SEQ ID NO:6) (*Mus musculus* transcript and protein sequences, respectively). In certain embodiments, stromal cells comprise non-endogenous nucleic acid sequences encoding DL4, such as human DL4. Exemplary Delta-like-4 sequences include Genbank Accession No. NM_019074.3 (SEQ ID NO:7) and NP_061947.1 (SEQ ID NO:8) (*Homo sapiens* transcript and protein sequences, respectively) and Genbank Accession No. NM_019454.3 (SEQ ID NO:9) and NP_062327.2 (SEQ ID NO:10) (*Mus musculus* transcript and protein sequences, respectively). Notch ligands are commercially available or can be produced by standard recombinant DNA techniques and purified to various degrees.

In still further embodiments, stromal cells are OP9 cells or a derivative thereof expressing DL1, such as human DL1. OP9 cells expressing DL1 and DL4 have been previously described (Schmitt et al., 2002, Immunity 17:749-756; U.S. Pat. No. 7,575,925).

In certain embodiments, stromal cells also comprise a nucleic acid sequence encoding an MHC molecule. In particular embodiments, stromal cells comprise a nucleic acid sequence encoding an MHC Class I molecule, and may optionally also comprise a nucleic acid sequence encoding a β2 microglobulin. The MHC Class I and β2 microglobulin molecules may be derived from human, mouse, rat, or other mammalian species MHC Class I molecules, whose genes and protein sequences are known in the art. In other embodiments, the stromal cells comprise a nucleic acid sequence encoding an MHC Class II molecule. The MHC Class II molecule may be derived from human, mouse, rat, or other mammalian species MHC molecules, whose genes and protein sequences are known in the art.

A given T cell will recognize a peptide antigen only when it is bound to a host cell's MHC molecule (MHC-restricted antigen recognition). A parent TCR with specificity for a known peptide antigen is selected for enhancement of the TCR affinity using the disclosed methods. Therefore, an MHC molecule that binds the particular peptide antigen is also selected and expressed in the stromal cells to allow MHC-restricted antigen recognition in the disclosed in vitro system. Methods for identifying an MHC molecule that binds a peptide antigen are known in the art (see, e.g., Akatsuka et al., 2002, Tissue Antigens 59:502-511). In certain embodiments, an MHC molecule comprises HLA-A2 and beta-2 microglobulin, preferably of human origin, which can bind to, for example, the WT1 peptide RMFPNAPYL (SEQ ID NO:2). In other embodiments, an MHC molecule comprises mouse $H\text{-}2D^b$, which can bind to, for example, the WT1 peptide RMFPNAPYL or various mesothelin peptides as disclosed in FIG. 3A of Hung et al., 2007, Gene Therapy 14:921-929, or $H\text{-}2K^b$ which can bind to, for example, various mesothelin peptides as disclosed in FIG. 3A of Hung et al. Potential $H\text{-}2D^b$ restricted mesothelin epitopes disclosed in Hung et al. include: ISKANVDVL (SEQ ID NO:42), GQKMNAQAI (SEQ ID NO:43), SAFQNVSGL (SEQ ID NO:44), and LLGPNIVDL (SEQ ID NO:45). Potential H-2 Kb restricted mesothelin epitopes disclosed in Hung et al. include: EIPFTYEQL (SEQ ID NO:46) and GIPNGYLVL (SEQ ID NO:47).

A peptide antigen used in the disclosed methods refers to a peptide sequence of an antigen, or target biological molecule (e.g., a polypeptide, protein), to which the parent TCR specifically binds. A peptide sequence may be derived from an antigen that is expressed on the cell surface, within a cell, or that is an integral membrane protein. The antigen may be a host-derived antigen (e.g., a tumor/cancer antigen, and autoimmune antigen), or an exogenous antigen (e.g., viral, bacterial, protozoan antigen). A tumor or cancer antigen may be derived from various cancers, such as those noted herein. In some embodiments, a cancer antigen comprises a leukemia antigen. In certain embodiments, a peptide antigen is derived from Wilm's tumor 1 (WT1), such as a WT1 peptide comprising the amino acid sequence RMFPNAPYL (SEQ ID NO:2). In other embodiments, a peptide antigen is derived from mesothelin, such as mesothelin peptides disclosed in FIG. 3A of Hung et al., 2007, Gene Therapy 14:921-929. In some embodiments, the mesothelin peptide comprises the amino acid sequence GQKMNAQAI (SEQ ID NO:31). In other embodiments, the mesothelin peptide comprises an amino acid sequence comprising ISKANVDVL (SEQ ID NO:42), GQKMNAQAI (SEQ ID NO:43), SAFQNVSGL (SEQ ID NO:44), and LLGPNIVDL (SEQ ID NO:45), EIPFTYEQL (SEQ ID NO:46), or GIPNGYLVL (SEQ ID NO:47). Autoimmune antigens are antigens that are recognized by autoreactive TCRs specific for self-antigens, with the ensuing immune effector functions causing autoimmune disease, exacerbating autoimmune disease, contributing to progression of autoimmune disease, causing or worsening symptoms associated with autoimmune disease. For example, autoreactive TCRs specific for a collagen peptide may be useful for suppressive gene therapy of Tregs in rheumatoid arthritis. Autoimmune antigens may also be antigens located on other immune cells that cause autoimmune disease or mediate symptoms of autoimmune disease (e.g., B cells that produce autoantibodies). For example, CD20 peptide antigens may be useful for generating enhanced affinity TCRs that target B cells involved in or associated with rheumatoid arthritis. A peptide antigen may be added to a culture system to hematopoietic progenitor cells and stromal cells as described herein. Alternatively, stromal cells comprising a nucleic acid sequence encoding a peptide antigen of interest may be used to express such antigen in the cell culture. Without wishing to be bound by theory, a peptide antigen, whether added as an exogenous peptide antigen to the culture system or expressed by stromal cells, forms a complexe with a MHC molecule expressed by the stromal cells to form an MHC-peptide antigen complex. MHC-peptide antigen complex allows for MHC-restricted peptide antigen recognition by TCRs in the culture system. In certain embodiments, OP9 cells are transduced with a nucleic acid sequence to express the WT1 antigen peptide RMFPNAPYL (SEQ ID NO:2). In other embodiments, OP9 cells are transduced with a nucleic acid sequence to express the mesothelin antigen peptide GQKMNAQAI (SEQ ID NO:31).

Peptides that bind to MHC class I molecules are generally from about 7 to about 10 amino acids in length. Peptides that bind to MHC class II molecules are variable in length, usually about 10-25 amino acids long. In certain embodiments, the parent TCR's peptide antigen specificity is known. In other embodiments, the parent TCR's peptide antigen specificity needs to be determined using methods known in the art (Borras et al., 2002, J. Immunol. Methods 267:79-97; Hiemstra et al., 2000, Cur. Opin. Immunol. 12:80-4). For example, if the target antigen of a parent TCR is known, though not the specific peptide sequence, peptide libraries derived from the target antigen polypeptide sequence may be used for screening and identifying the specific peptide antigen for the parent TCR.

A "vector" is a nucleic acid molecule that is capable of transporting another nucleic acid. Vectors may be, for example, plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include, but are not limited to, mouse stem cell virus, murine leukemia virus, feline leukemia virus, feline sarcoma virus, and avian reticuloendotheliosis viruses.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

A vector that encodes a core virus is also known as a "viral vector." There are a large number of available viral vectors that are suitable for use with the invention, including those identified for human gene therapy applications, such as those described by Pfeifer and Verma (Pfeifer, A. and I. M. Verma. 2001. Ann. Rev. Genomics Hum. Genet. 2:177-211). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and maedi/visna virus. Methods of using retroviral and lentiviral viral vectors and packaging cells for transducing mammalian target cells with viral particles containing TCRs transgenes are well known in the art and have been previous described, for example, in U.S. Pat. No. 8,119,772; Walchli et al., 2011, PLoS One 6:327930; Zhao et al., J. Immunol., 2005, 174: 4415-4423; Engels et al., 2003, Hum. Gene Ther. 14:1155-68; Frecha et al., 2010, Mol. Ther. 18:1748-57; Verhoeyen et al., 2009, Methods Mol. Biol. 506:97-114. Retroviral and lentiviral vector constructs and expression systems are also commercially available.

In a specific embodiment, a viral vector is used to introduce the non-endogenous nucleic acid sequence encoding TCRα chain specific for the peptide antigen into the hematopoietic progenitor cells. In another embodiment a viral vector is used to introduce non-endogenous nucleic acid sequence encoding DL1 or DL4 and a nucleic acid sequence encoding an MHC molecule into stromal cells. The viral vector may be a retroviral vector or a lentiviral vector. The viral vector may also include a nucleic acid sequence encoding a marker for transduction. Transduction markers for viral vectors are known in the art and include selection markers, which may confer drug resistance, or detectable markers, such as fluorescent markers or cell surface proteins that can be detected by methods such as flow cytometry. In a particular embodiment, the viral vector further comprises a gene marker for transduction comprising green fluorescent protein or the extracellular domain of human CD2. Where the viral vector genome comprises more than one nucleic acid sequence to be expressed in the host cell as separate transcripts, the viral vector may also comprise additional sequence between the two (or more) transcripts allowing bicistronic or multicistronic expression. Examples of such sequences used in viral vectors include internal ribosome entry sites (IRES), furin cleavage sites, viral 2A peptide.

Other vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., 1998, Gene Ther. 5: 1517-30).

Other vectors that have recently been developed for gene therapy uses can also be used with the methods of this disclosure. Such vectors include those derived from baculoviruses and alpha-viruses. (Jolly D J. 1999. Emerging viral vectors. pp 209-40 in Friedmann T. ed. 1999. The development of human gene therapy. New York: Cold Spring Harbor Lab).

The hematopoietic progenitor cells are cultured with stromal cells comprising a nucleic acid sequence encoding a non-endogenous DL1 or DL4 and a nucleic acid sequence encoding a MHC molecule under conditions and for a time sufficient to induce differentiation of hematopoietic progenitor cells into DN TCRαβ$^+$ thymocytes. In certain embodiments, the hematopoietic progenitor cells are cultured in a 6 cm or 10 cm tissue culture-treated dish. The concentration of hematopoietic progenitor cells in the culture can be between 1-$10^9$, or $1\times10^2$ to $1\times10^6$, or $1\times10^3$ to $1\times10^4$. In some embodiments, hematopoietic progenitor cells (about 1-5× $10^4$ cells) are cultured on a monolayer of OP9 cells expressing DL1.

One or more cytokines that promote commitment and differentiation of hematopoietic progenitor cells may also be added to the culture. The cytokines may be derived from human or other species. The concentration of a cytokine in culture can range from about 1 ng/ml to about 50 ng/ml. Representative examples of cytokines that may be used include: all members of the FGF family, including FGF-4 and FGF-2; Flt-3-ligand, stem cell factor (SCF), thrombopoietin (TPO), and IL-7. Cytokines may be used in combination with a glycosaminoglycan, such as heparin sulfate. Cytokines are commercially available or can be produced by recombinant DNA techniques and purified to various degrees. Some cytokines may be purified from culture media of cell lines by standard biochemical techniques.

The hematopoietic progenitor cells may be cultured in culture medium comprising conditioned medium, non-conditioned medium, or embryonic stem cell medium. Examples of suitable conditioned medium include IMDM, DMEM, or αMEM, conditioned with embryonic fibroblast cells (e.g., human embryonic fibroblast cells), or equivalent medium. Examples of suitable non-conditioned medium include Iscove's Modified Delbucco's Medium (IDMD), DMEM, or αMEM, or equivalent medium. The culture medium may comprise serum (e.g., bovine serum, fetal bovine serum, calf bovine serum, horse serum, human serum, or an artificial serum substitute) or it may be serum free.

Culture conditions entail culturing the hematopoietic progenitor cells for a sufficient time to induce differentiation of hematopoietic progenitor cells into DN TCRαβ$^+$ thymocytes. The cells are maintained in culture generally for about 4-5 days, preferably about 5 to 20 days. It will be appreciate that the cells may be maintained for the appropriate amount of time required to achieve a desired result, i.e., desired cellular composition. For example, to generate a cellular composition comprising primarily immature and inactivated T cells, the cells may be maintained in culture for about 5 to 20 days. Cells may be maintained in culture for 20 to 30 days to generate a cellular composition comprising primarily mature T cells. Non-adherent cells may also be collected from culture at various time points, such as from about several days to about 25 days. Culture methods for hematopoietic stem cells on stromal cells lines have been previously described (U.S. Pat. No. 7,575,925; Schmitt et al., 2004, Nat. Immunol. 5:410-417; Schmitt et al., 2002, Immunity 17:749-756).

Differentiation of hematopoietic progenitor cells into DN TCRαβ+ thymocytes may be detected and these cells isolated using standard flow cytometry methods. One or more cell sorts may be employed to isolate the DN TCRαβ+ thymocytes. For example, a first cell sort may identify hematopoietic progenitor cells expressing the transduction marker (i.e., marker for TCRα expression). In certain embodiments, a transduction marker is the extracellular domain of human CD2. In further embodiments, transduction marker positive cells may be subjected to a second cell sort to screen for cells that are CD4$^-$ and CD8$^-$. A third cell sort on the DN cells may screen for cells expressing TCRβ. It will be apparent to one skilled in the art that a subset of these sorts, or single or multiple cell sorts can be designed using different combinations of cell surface or transduction markers, in order to identify the desired subpopulation of DN TCRαβ+ thymocytes. Methods for sorting DN TCRαβ+ cells are known in the art (U.S. Pat. No. 7,575,925 and Schmitt et al., 2002, Immunity:17:749-756).

The nucleic acid sequences encoding the various TCRβ chains from the DN TCRαβ$^+$ thymocytes are isolated and introduced into T cells comprising the nucleic acid sequence encoding the TCRα chain from the parent TCR. As discussed herein, methods of cloning TCRβ chains from cells are well known in the art and have been previously described. In certain embodiments, once the nucleic acid sequences encoding the candidate TCRβ chains have been isolated from the DN TCRαβ$^+$ thymocytes, the nucleic acid sequences may be subjected to a further selection process whereby the TCRβ chains with the same $V_\beta$ gene used by the parent TCRβ chain are selected for introduction into T cells. Parent $V_\beta$ gene containing TCRβ chain may be identified within the sorted cell population using $V_\beta$ gene specific primers for PCR. One concern associated with enhancing the affinity of antigen-specific TCRs in vitro is that some modifications might increase the affinity of the receptor for MHC only, rather than peptide/MHC, thereby increasing the likelihood that the TCR will be autoreactive. Restricting the candidate TCRβ chains to those containing the parent $V_\beta$ gene increases the likelihood of retaining the TCR CDR1 and CDR2 domains that contact the MHC, and limiting variability to CDR3. As previously discussed, viral vectors, such as retroviral vectors and lentiviral vectors, are suitable for introducing the nucleic acid sequences encoding the various TCRβ chains and/or the parent TCRα into T cells. In some embodiments, the viral vector further comprises a gene marker for transduction (e.g. green fluorescent protein).

Cells that are capable of expressing a TCR on the cell surface are used for transformation or transduction with the nucleic acid sequences encoding the various TCRβ chains from the DN TCRαβ$^+$ thymocytes. Cells that are capable of expressing a TCR on the cell surface express a CD3 molecule. "CD3" is a multi-protein complex of six chains that are stably associated with a TCR on the cell surface. In mammals, the complex comprises a CD3γ chain, a CDδ chain, two CD3ϵ, and a homodimer of CD3ζ chains. The CD3γ, CD3δ, and CD3ϵ are highly related cell surface proteins of the immunoglobulin superfamily containing a single immunoglobulin domain. The transmembrane regions of CD3γ, CD3δ, and CD3ϵ are negatively charged, which is a characteristic that allows these chains to associate with the positively charged TCR chains. The cytoplasmic domains of the CD3γ, CD3δ, and CD3ϵ chains contain immunoreceptor tyrosine-based activation motifs (ITAMs) that allow them to associate with cytosolic protein tyrosine kinases following receptor stimulation and thereby signal to the cell interior. CD3 proteins are required for cell-surface expression of the TCR (see Janeway et al., *Immunobiology: The Immune System in Health and Disease,* 3$^{rd}$ Ed., Current Biology Publications, p. 4:39, 1997).

In some embodiments, cells that are capable of expressing a TCR on the cell surface are T cells, including primary cells or cell lines derived from human, mouse, rat, or other mammals. If obtained from a mammal, a T cell can be obtained from numerous sources, including blood, bone marrow, lymph node, thymus, or other tissues or fluids. A T cell may be enriched or purified. T cell lines are well known in the art, some of which are described in Sandberg et al., 2000, Leukemia 21:230-237. In certain embodiments, T cells which lack endogenous expression of TCRα and β chains are used. Such T cells may naturally lack endogenous expression of TCRα and β chains or may have been modified to block expression (e.g., T cells from a transgenic mouse that does not express TCR α and β chains or a cell line that has been manipulated to inhibit expression of TCR α and β chains). In certain embodiments, 58 $\alpha^-\beta^-$ cells, a murine T cell line that lacks endogenous TCRα and TCRβ chains, is used (Letourneur and Malissen, 1989, Eur. J. Immunol. 19:2269-74). In other embodiments, H9 T cell line is used (Catalog #HTB-176, ATCC, Manassas, Va.). In certain embodiments, cells that capable of expressing a TCR on the cell surface are not T cells or cells of a T cell lineage, but cells that have been modified to express CD3, enabling cell surface expression of a TCR (e.g., 293 cells or 3T3 cells). Cell surface expression of TCRs on cells that are not of a T cell lineage has been previously described (Szymczak et al., 2004, Nat. Biotechnol. 22:589-594).

To identify a potential enhanced affinity TCR, once cells that are capable of expressing a TCR on the cell surface that also express the parent TCRα chain have been transformed or transduced with a library of candidate TCRβ chains, antigen-specific cells are sorted or identified using MHC-peptide tetramer staining MHC-peptide tetramer staining features a tetramer of MHC molecules, each comprising an identical peptide having an amino acid sequence that is cognate (e.g., identical or related to) at least one antigen, wherein the complex is capable of binding T cells specific for the cognate antigen. Each of the MHC molecules may be tagged with a biotin molecule. Biotinylated MHC/peptides are tetramerized by the addition of streptavidin, which is typically fluorescently labeled. The tetramer may be detected by flow cytometry via the fluorescent label. MHC-peptide tetramer staining methods for detecting antigen specific T cells are well known in the art (e.g., Altman et al, 1996, Science 274:94-96; Kalergis et al., 2000, J. Immunol. Methods 234:61-70; Xu and Screaton, 2002, J. Immunol. Methods 268:21-8; James et al., J. Vis. Exp. 25:1167). In certain embodiments, the MHC-peptide tetramer comprises MHC Class I molecules. In other embodiments, the MHC-peptide tetramer comprises MHC Class II molecules. In further embodiments, the same peptide antigen used the culture step of the disclosed method is the same as the peptide incorporated into the MHC-peptide tetramer. In other embodiments, the MHC molecule expressed by the stromal cells in the culture step of the disclosed method is the same as an MHC molecule in the MHC-peptide tetramer. MHC-peptide tetramer stained cells may be sorted by flow cytometry one or more times. A first sort may select for transduced cells expressing a detectable transduction marker (e.g., green fluorescent protein). The transduction positive cells may also be sorted one or more times for cells that express the same Vβ chain as the parent TCR. It will be apparent to one skilled in the art that a subset of these sorts, or single or multiple cell sorts can be designed using different combinations of cell surface or transduction markers, in order to identify the desired subpopulation of cells.

An enhanced affinity TCR is identified by comparing the binding affinity of a candidate TCRαβ with the parent TCRαβ. Antigen-specific T cells may then be cloned and sequenced using standard molecular biology techniques. Candidate TCRβ clones may then be used to transduce T cells comprising the parent TCRα chain and MHC-peptide tetramer staining may be used to compare staining levels with the parent TCRαβ, as previously described. Increased staining observed with a candidate TCRβ may be indicative of enhanced affinity as compared with the parent TCRαβ. However, if the parent TCRαβ was codon-optimized for increased expression in the T cell, direct comparison of tetramer staining levels with the candidate TCRβ may not be possible. Candidate TCRβ chains may also be codon optimized for direct comparison with the parent TCRβ

A candidate TCRαβ has enhanced affinity compared to a parent TCRαβ if it has stronger binding to the peptide antigen than the parent TCRαβ. Enhanced affinity may be indicated by a TCR with a $K_a$ (equilibrium association constant) for the target antigen higher than that of the parent TCR, a TCR with a $K_D$ (dissociation constant) for the target antigen less than that of the parent TCR, or with an off-rate ($K_{off}$) for the target antigen less than that of the wild type (or parent) TCR. Methods of measuring TCR binding affinity have been previously described (e.g., Laugel et al., 2007, J. Biol. Chem. 282:23799-23810; Garcia et al., 2001, Proc. Natl. Acad. Sci. USA 98:6818-6823).

Enhanced Affinity TCRs and Compositions

In another aspect, enhanced affinity TCRs generated by methods disclosed herein are provided. An enhanced affinity TCR may be cell-bound (e.g., expressed on the surface of a mature T cell) or in soluble form. In certain embodiments, enhanced affinity TCRs may be codon optimized to enhance expression in T cells (Scholten et al., 2006, Clin. Immunol. 119:135-145).

In other embodiments, enhanced affinity TCRs may also be a component of a fusion protein, which may further comprise a cytotoxic component (e.g., chemotherapeutic drugs such as vindesine, antifolates; bacterial toxins, ricin, anti-virals), which is useful for specific killing or disabling of a cancer cell or infected cell or a detectable component (e.g., biotin, fluorescent moiety, radionuclide), which is useful for imaging cancer cells, infected cells, or tissues under autoimmune attack.

The present disclosure also provides pharmaceutical compositions comprising an enhanced affinity TCR generated by the methods disclosed herein and a pharmaceutically acceptable carrier, diluents, or excipient. Suitable excipients include water, saline, dextrose, glycerol, ethanol, or the like and combinations thereof.

Applications

Enhanced affinity TCRs generated by the methods of the present disclosure may be used to treat a disease (such as cancer, infectious disease, or autoimmune disease) in a subject by administering a composition comprising the enhanced affinity TCRs.

Diseases that may be treated with enhance affinity TCR therapy include cancer, infectious diseases (viral, bacterial, protozoan infections), and autoimmune diseases. TCR gene therapy is a promising treatment for various types of cancer (Morgan et al., 2006, Science 314:126-129; reviewed in Schmitt et al, 2009, Human Gene Therapy; reviewed in June, 2007, J. Clin. Invest. 117:1466-1476) and infectious disease (Kitchen et al., 2009, PLoS One 4:38208; Rossi et al., 2007, Nat. Biotechnol. 25:1444-54; Zhang et al., PLoS Pathog. 6:e1001018; Luo et al., 2011, J. Mol. Med. 89:903-913). Immunosuppressive gene therapy for autoimmune diseases using regulatory T cells comprising autoreactive TCRs is also an emerging treatment (Fujio et al., 2006, J. Immunol. 177:8140-8147; Brusko et al., 2008, Immunol. Rev. 223:371-390).

A wide variety of cancers, including solid tumors and leukemias are amenable to the compositions and methods disclosed herein. Types of cancer that may be treated include: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include: angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Exemplifying the variety of hyperproliferative disorders amenable to enhanced TCR therapy are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia and chronic myoblastic leukemia) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphomaleukemia, B-cell proliferations of uncertain malignant potential, lymphomatoid granulomatosis, and post-transplant lymphoproliferative disorder.

Autoimmune diseases include: arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitisangiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-BarréSyndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

In a particular embodiments, a method of treating a subject with the enhanced affinity TCRs generated by the methods disclosed herein include a subject with acute myelocytic leukemia, acute lymphocytic leukemia, or chronic myelocytic leukemia.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses (e.g., adenovirus, bunyavirus, herpesvirus, papovavirus, paramyxovirus, picornavirus, rhabdovirus (e.g., Rabies), orthomyxovirus (e.g., influenza), poxvirus (e.g., Vaccinia), reovirus, retroviruses, lentiviruses (e.g., HIV), flaviviruses (e.g., HCV) and the like). In certain embodiments, infection with cytosolic pathogens whose antigens are processed and displayed with MHC Class I molecules, are treated with the enhanced affinity TCRs of the invention.

The enhanced affinity TCRs may be administered to a subject in cell-bound form (i.e., gene therapy of target cell population (mature T cells (e.g., CD8$^+$ T cells) or other cells of T cell lineage)). In a particular embodiment, the cells of T cell lineage comprising enhanced affinity TCRs administered to the subject are autologous cells. In another embodiment, the enhanced affinity TCRs may be administered to a subject in soluble form. Soluble TCRs are known in the art (see, e.g., Molloy et al., 2005, Curr. Opin. Pharmacol. 5:438-443; U.S. Pat. No. 6,759,243).

"Treat" and "treatment" refer to medical management of a disease, disorder, or condition of a subject (i.e., individual who may be a human or non-human mammal (e.g., primate, mouse, rat)). In general, an appropriate dose and treatment regimen provide the herein described enhanced affinity TCRs, and optionally, an adjuvant, in an amount sufficient to provide therapeutic or prophylactic benefit. Therapeutic and prophylactic benefits include improved clinical outcome; lessening or alleviation of symptoms associated with the disease; decreased occurrence of symptoms; improved quality of life; longer disease-free status; diminishment of extent of disease, stabilization of disease state; delay of disease progression; remission; survival; or prolonging survival.

Pharmaceutical compositions including the enhanced affinity receptors may be administered in a manner appropriate to the disease or condition to be treated (or prevented) as determined by persons skilled in the medical art. An appropriate dose, suitable duration, and frequency of administration of the compositions will be determined by such factors as the condition of the patient, size, type and severity of the disease, particular form of the active ingredient, and the method of administration.

In further embodiments, enhanced affinity TCRs of the instant disclosure may be used in diagnostic methods or imaging methods, including these methods used in relation to the indications or conditions identified herein.

EXAMPLES

The following examples demonstrate that, as provided by the instant disclosure, for example, TCR transgenic thymocytes efficiently differentiate into a "γδ like" CD4$^-$CD8$^-$ CD24$^-$TCRβ$^+$ lineage when exposed to their cognate antigen in OP9-DL1 cultures. Furthermore, progenitor thymocytes expressing only the TCRα chain from a T cell clone specific for the tumor antigen WT1 can also differentiate into this mature TCRαβ+ lineage in OP9-DL1 culture. A library of TCRβ chains was generated from a population of DN TCRαβ+ cells sorted from these cultures, and screened for WT1 MHC tetramer reactivity when paired with the antigen-specific TCRα chain. Using this approach, several TCRβ chains were identified that can pair with an antigen-specific TCRα chain to generate TCRs with up to 10-fold higher affinity for WT1 peptide as compared to the original TCR.

Example 1

Engagement of Peptide Agonist During Differentiation on OP9-DL1 Cells can Drive Differentiation of Mature TCRαβ+ DN Cells from T Cell Progenitors Purified from TCR Transgenic Mice Agonist signals through an αβ TCR prior to β-selection results in the differentiation of "γδ like" double negative (DN) TCRαβ$^+$ cells during T cell development in vivo, and TCR cross-linking at the DN3 stage leads to the differentiation of a similar lineage during in vitro T cell differentiation on OP9-DL1 cells. In order to determine whether progenitor T cells from TCR transgenic mice could also differentiate into a DN TCRαβ$^+$ lineage in response to cognate peptide antigen at the DN3 stage, TCRαβ$^-$CD4$^-$CD8$^-$CD117$^+$CD44$^+$ DN1 and DN2 progenitor thymocytes were sorted from transgenic OT-1 mice (express TCR specific for ovalbumin peptide sequence SIINFEKL (SEQ ID NO:1) presented on MHC Class I H-2K$^b$; Stock #003831, Jackson Laboratory, ME; see also Hogquist et al., 1994, Cell 76:17-27) and cultured with OP9-DL1 cells (Schmitt et al., 2002, Immunity 17:749-756; U.S. Pat. No. 7,575,925) transduced to express the mouse MHC Class I molecule H-2K$^b$, either in the absence of peptide, or with increasing concentrations of ovalbumin-specific peptide (SEQ ID NO:1) for 20 days and analyzed at various time points by flow cytometry. In the absence of peptide, double positive (DP) T cells could be detected by day 16, and constituted a major fraction of the culture by day 20 (FIG. 1A). However, the development or survival of DP T cells was diminished by even very low concentrations of peptide (0.0001 μM), and DP were completely absent from cultures containing 0.01 μM or more of peptide (FIG. 1A), demonstrating that DP cells are negatively selected by strong agonist signaling in OP9-DL1 cultures.

Figure 1B:
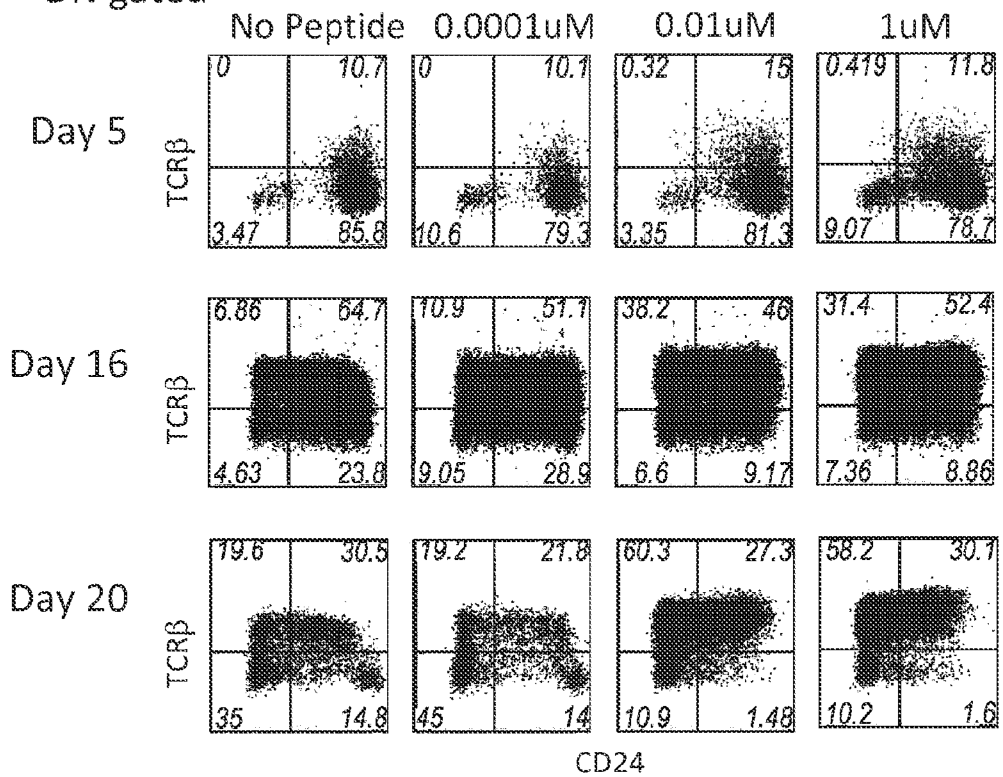
Figure 1C:
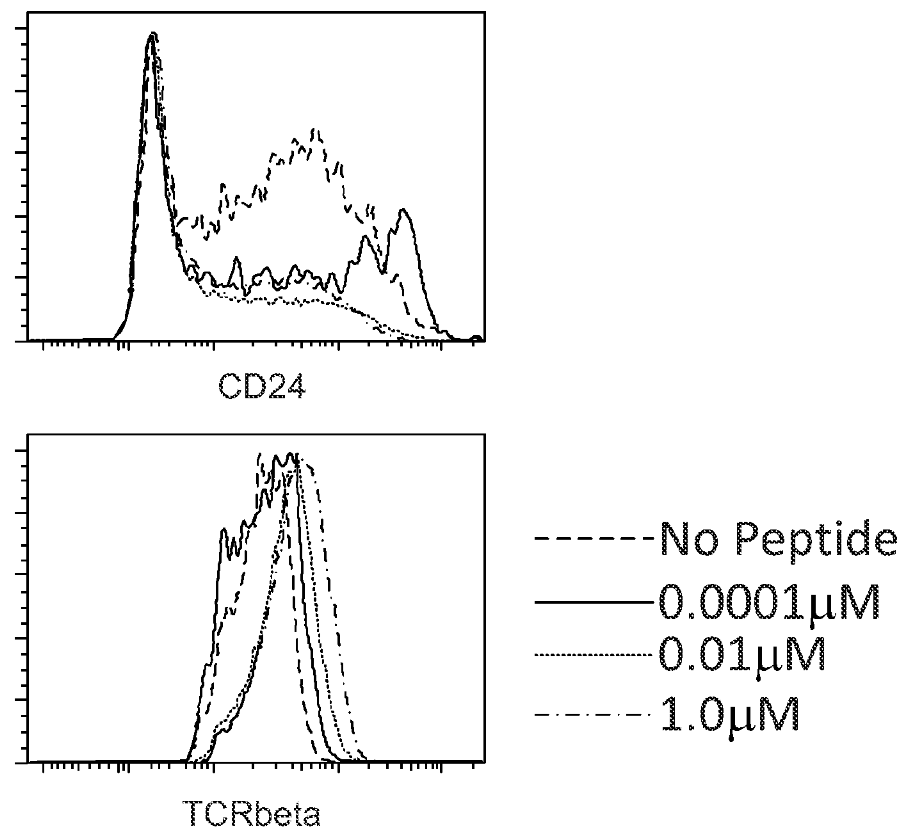
Figure 1D:
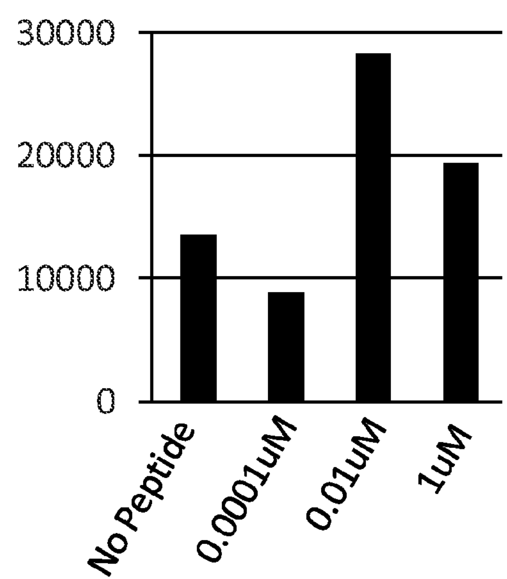
Figure 2:
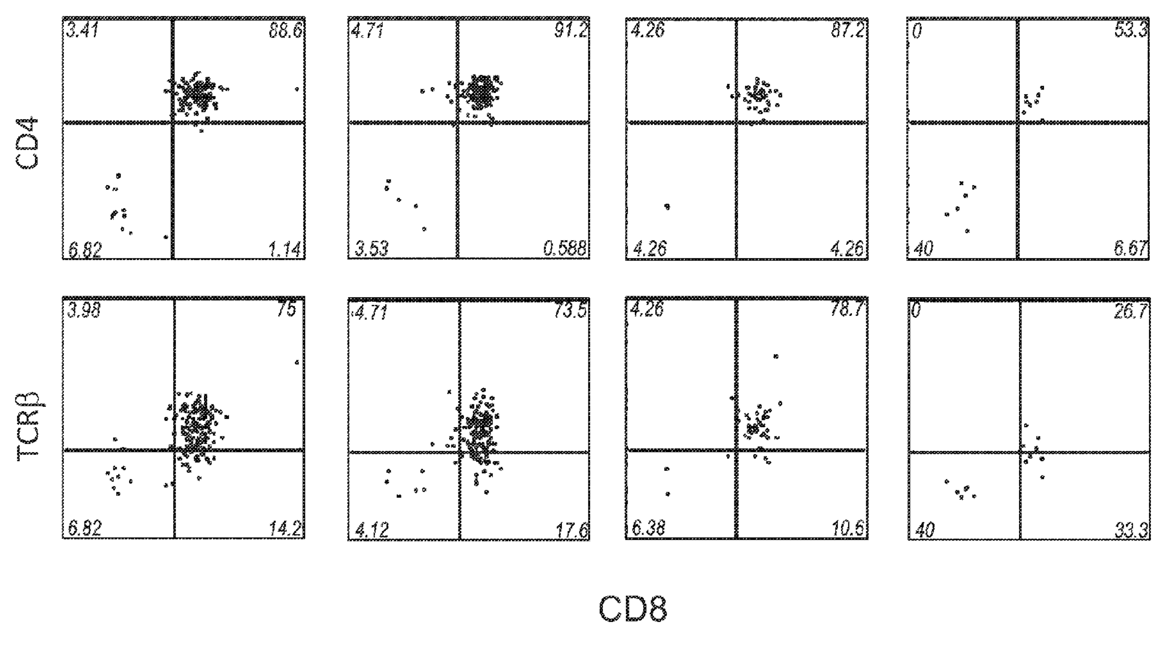
FIG. 2: $CD69^{-}$ DP thymocytes that have not yet gone through positive selection sorted from B6 or OT-1 transgenic mice were cultured on OP9-DL1 cells expressing MHC Class I H-2 Kb molecule in the presence of ovalbumin SIINFEKL peptide (SEQ ID NO:1).

In order to determine whether increasingly strong agonist signals drive the development of TCRαβ$^+$ DN cells, the DN population was analyzed for expression of CD24, a maturation marker that is expressed at high levels on all immature progenitor T cell populations, and TCRβ. The majority of cells were found to express high levels of CD24 and to lack TCRβ expression at day 5 (FIG. 1B), but by day 16, a majority of DN cells from all culture conditions expressed TCRβ, although a substantially greater number of CD24$^-$ cells were observed from cultures that contained 0.01 μM or more of peptide (38.2% and 31.4% TCR$^+$CD24$^-$ cells in cultures containing 0.01 and 1.0 μM of peptide, respectively, compared to 6.9% TCR$^+$CD24$^-$ in the no peptide culture) (FIG. 1B). By day 20, ~60% of all DN cells were TCRβ$^+$ CD24$^-$ from cultures containing 0.01 μM or 1.0 μM peptide, while in cultures that received no peptide or a low concentration (0.0001 μM) of peptide, only ~20% of DNs were TCRβ$^+$CD24$^-$, and close to 50% were TCRβ$^-$ (FIG. 1B, 1C). Furthermore, when the level of TCR surface expression is compared between the different culture conditions, the TCRβ$^+$ cells that developed in response to high levels of peptide expressed higher levels of TCRβ on the cell surface (FIG. 1C). Without wishing to be bound by theory, it is possible that the development of some TCRαβ$^+$ DN cells in cultures without added peptide is due to cross-reactivity with other peptide-MHC ligands in the OP9-DL1 culture system. To confirm that the TCRαβ$^+$ DN cells observed in these cultures did not develop through a DP stage, CD69$^-$ DP cells that have not yet been positively selected were sorted from B6 or OT-1 thymus and cultured in the presence or absence of ovalbumin SIINFEKL peptide (SEQ ID NO:1). B6 DP cells were unaffected by the presence of SIINFEKL peptide (SEQ ID NO:1), but when OT-1 DP thymocytes were cultured on OP9-DL1 cells in the presence SIINFEKL (SEQ ID NO:1), all the hallmarks of negative selection were observed, including a massive loss of cellularity and co-receptor down-modulation (FIG. 2). Importantly, the DN cells observed in these cultures were uniformly TCR negative (FIG. 2).

These data indicate that engagement of a peptide agonist during differentiation on OP9-DL1 cells can drive the differentiation of mature TCRαβ$^+$ DN cells from T cell progenitors purified from TCR transgenic mice.

Example 2

Figure 3:
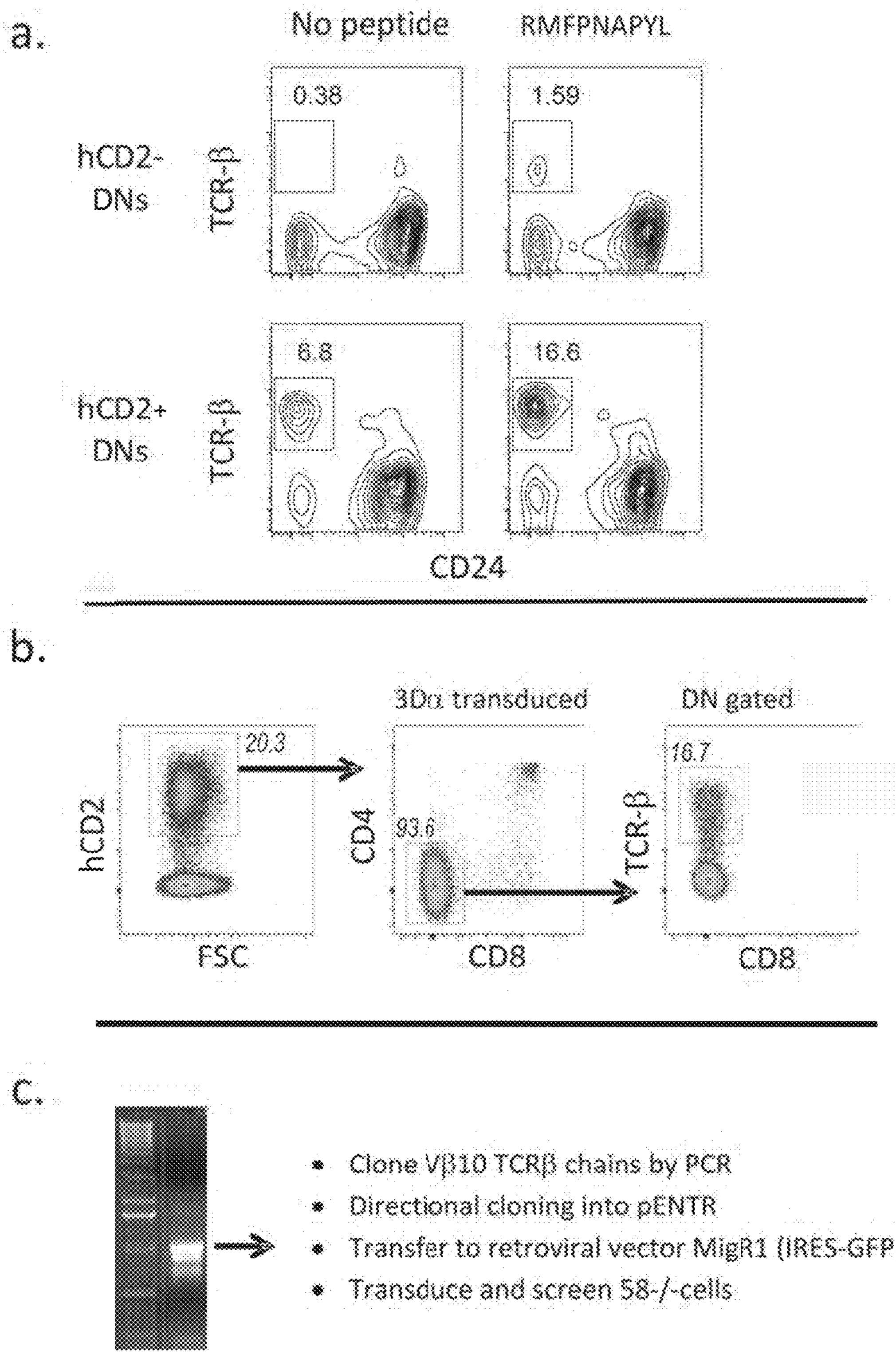
FIGS. 3A-C: B6 thymocytes were sorted for $CD4^{-}CD8^{-}CD117^{+}CD44^{+}$ DN1 and DN2 progenitor cells and transduced with the TCRα chain of the affinity enhanced WT1 specific TCR 3D clone, and cultured on OP9-DL1 cells expressing MHC Class I H-2 Db molecule in the presence or absence of 1 μM of WT1 peptide RMFPNAPYL (SEQ ID NO:2). (A) On day 16 of culture, transduced ($hCD2^{+}$) and untransduced ($hCD2^{-}$) cells were analyzed by flow cytometry. (B) On day 21 of OP9-DL1 culture in the presence of 1 μM WT1 peptide RMFPNAPYL (SEQ ID NO:2), DN $TCR\alpha\beta^{+}$ cells were sorted according to the scheme indicated. (C) Sorted cells were lysed, DNA was isolated, and PCR was performed using a Vb10-specific forward primer and a Cb2-specific reverse primer. The Vb10 PCR product was then directionally TOPO-cloned into vector pENTR/D-TOPO, transferred to the retroviral vector MigR1-attR using Gateway® technology, and retroviral supernatant was generated and used to transduce murine $58^{-/-}$ cells for library screening as described.

A Transgenic TCRα Chain Pairs with Endogenous TCRβ Chains to Drive the Development of DN CD24$^-$ TCRαβ$^+$"γδ Wanna-be" Cells in the OP9-DL1 Culture System To determine whether the expression of only a TCRα chain prior to β-selection should also result in the lineage diversion of DN3 T cell progenitors that express an endogenous TCRβ chain that pairs with the introduced TCRα chain capable of engaging a peptide-MHC ligand in the OP9-DL1 culture system above a certain affinity threshold, CD4$^-$CD8$^-$CD117$^+$CD44$^+$ DN1 and DN2 progenitor thymocytes were sorted from B6 mice and transduced with a TCRα chain from the Wilm's tumor antigen (WT1) specific T cell clone 3D that had previously been identified as an affinity enhanced variant isolated from a saturation mutagenesis library of the CDR3 region of the 3Dα. The 3Dα expression construct contains an intra-ribosomal entry sequence motif, followed by the extracellular domain of human CD2 (Genbank Accession Nos. NM_001767.3 (SEQ ID NO:48) and NP_001758.2 (SEQ ID NO:49) (transcript and protein sequences for full length CD2, respectively)) (IRES-hCD2) as a marker transduction. Transduced progenitor thymocytes were cultured in the presence or absence of 1.0 μM of the MHC Class I H-2D$^b$) restricted WT1 peptide RMFPNAPYL (SEQ ID NO:2) for 14 days, and then analyzed by flow cytometry. DN cells within the hCD2 negative fraction contained few TCRαβ$^+$ cells, regardless of the presence of peptide in the culture conditions. In contrast, the hCD2 positive fraction (which expressed the 3Dα gene) from cultures that did not receive peptide contained 6.8% TCRβ$^+$ cells, and the number of TCRαβ$^+$ cells increased to 16.6% when 1.0 μM WT1 peptide was added (FIG. 3A). These data indicate that a significant population of TCRαβ$^+$ DN cells can develop from early progenitor thymocytes that ectopically express a TCRα chain prior to β-selection. Furthermore, the fact that this population of TCRαβ$^+$ DN cells increases when cognate peptide (for the introduced TCRα chain) is present suggests that a substantial fraction of these cells developed in response to WT1 antigen-specific signals.

Taken together, these data indicate that the TCRαβ$^+$ DN population could potentially contain cells that express a TCRβ chain that can pair with the introduced 3Dα to form a TCR with a higher affinity for the MHC-WT1 peptide tetramer than the original enhanced affinity receptor, and significantly higher than could be isolated from the normal T cell repertoire.

Therefore, 3Dα-transduced CD4$^-$CD8$^-$CD117$^+$CD44$^+$ DN1 and DN2 progenitor thymocytes were differentiated on OP9-DL1 cells expressing mouse MHC Class 1 H-2D$^b$ and also transduced to express WT1. Non-adherent cells were collected at for several days up to day 21 and sorted for hCD2$^+$CD4$^-$CD8$^-$TCRβ$^+$ cells into TRIzol reagent (Invitrogen) (FIG. 3B). Cell sorts from individual days were pooled; RNA was purified, and cDNA was generated. The parent 3D TCR uses the Vb10 variable region. In order to retain the TCR CDR1 and CDR2 domains that contact MHC, the candidate TCRβ chains were restricted to those containing this variable region. Therefore, Vβ10-containing TCRβ chains within the sorted cell population were isolated by PCR using a Vβ10 specific forward primer, and a Cβ2 specific reverse primer (FIG. 3C). The Vb10-specific forward primer was designed to contain a CACC sequence allowing for directional TOPO-cloning into the pENTR™/D-TOPO® vector (Invitrogen), followed by transfer using Gateway® technology for recombination (Invitrogen) into the retroviral vector MigR1-attR (a version of the MigR1 vector (Pear et al., 1998, Blood 92:3780-3792) that has been modified to contain attR sites and the ccdB gene for Gateway® cloning). The MigR1-TCRβ library was used to transduce PlatE retroviral packaging cells (Morita et al., 2000, Gene Therapy 7:1063-1066; Cell Biolabs, Inc.) to generate retroviral supernatant, which was then used to retrovirally transduce 58 α$^-$β$^-$ cells, a murine T cell line that lacks endogenous TCRα and TCRβ chains, (58$^{-/-}$) (Letourneur and Malissen, 1989, Eur. J. Immunol. 19:2269-74).

Figure 4A:
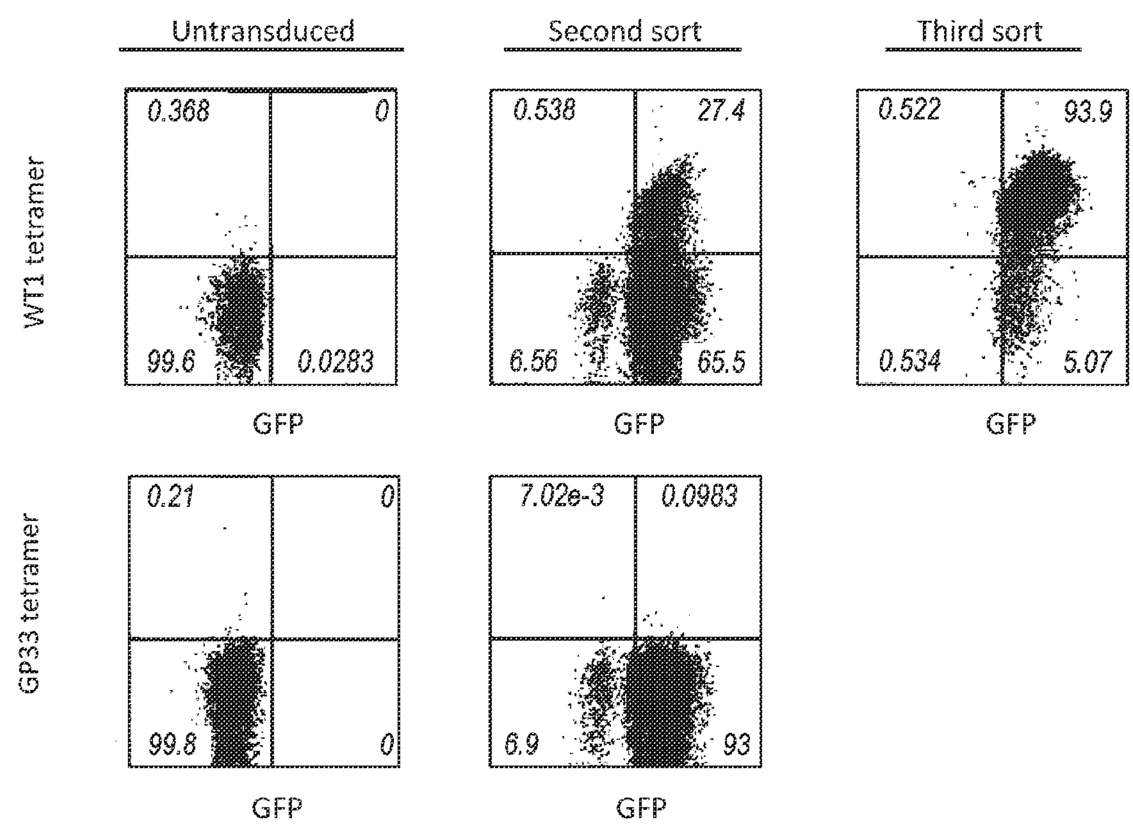

Retroviral TCRβ library supernatant was titrated, and a dilution that resulted in less than 20% transduced cells following transduction was used in order to ensure that most cells contained only one retroviral integration. Transduced cells were sorted first for GFP positive cells, and then resorted two more times on Vβ10$^+$ cells that also had high levels of MHC-WT1 peptide tetramer staining (FIG. 4A). Following the second sort, cells were analyzed for staining with an unrelated, but MHC H-2D$^b$-peptide tetramer specific for GP33, in order to assess whether MHC-WT1 peptide tetramer positive cells were binding in a peptide-independent manner to MHC residues (FIG. 4A).

Figure 4C:
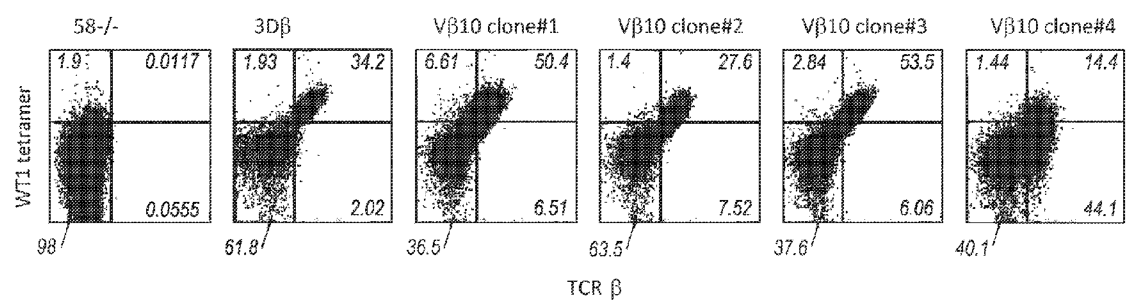

Following the third sort for MHC-WT1 peptide tetramer high, library-transduced 58$^{-/-}$ cells, the sorted cells were expanded, lysed, and the DNA was isolated. Retroviral inserts were recovered by PCR using MigR1-attR vector specific primers, designed to include AttB Gateway® cloning sites from the vector. Using a two-step approach, inserts were cloned first into the pDONR™ vector (Invitrogen) using Gateway® recombination cloning technology, and then back into MigR1-attR. Individual bacterial colonies were picked from the recombinational cloning reaction and sequenced. Following sequence analysis of >30 clones, the four most prevalent TCRβ chains were identified for further analysis. Interestingly, several of the clones had CDR3β sequences that shared multiple conserved residues with the original 3Dβ chain (FIG. 4B). One of the clones (Clone#1) was found to be almost identical to the original 3Dβ, except for a P108Q substitution and a G112S substitution (FIG. 4B). The four candidate TCRβ chains were retrovirally transduced into 3Dα$^+$58$^{-/-}$ cells and analyzed by flow cytometry (FIG. 4C). All four candidate clones bound MHC-WT1 peptide tetramer when transduced into 3Dα$^+$58$^{-/-}$ cells, although clone #4 bound MHC-WT1 peptide tetramer at significantly lower levels than the others and was not analyzed further. The parent 3Dβ chain had previously been codon-optimized, and therefore expressed higher levels of TCR at the cell surface, precluding direct comparison of tetramer staining levels between 3Dβ and the isolated clones.

Figure 5A:
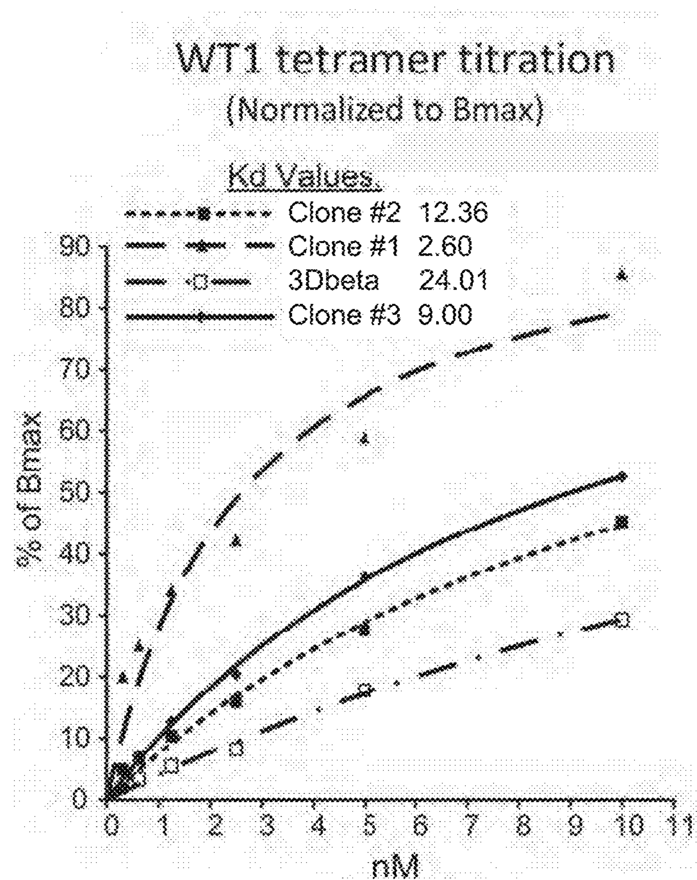
FIGS. 5A-C: (A) The relative affinity of the three highest affinity TCRs was determined by staining each transduced cell line with MHC-peptide tetramer followed by flow cytometry. $K_D$ measurements were performed using six 2-fold dilutions of PE-conjugated tetramers, and apparent $K_D$ values were determined from binding curves by non-linear regression, as the concentration of ligand that yielded half-maximal binding. (B) The highest affinity TCRβ chain (clone#1) was codon-optimized, and tetramer binding was compared to the original enhanced affinity 3Dαβ construct (C) 58−/− cells transduced with each of the candidate TCRβ chains paired with 3Dα were stained with MHC-WT1 peptide specific tetramer, as well as several non-specific MHC H-2Db-peptide tetramers in order to assess potential peptide-independent reactivity towards MHC.
Figure 5B:
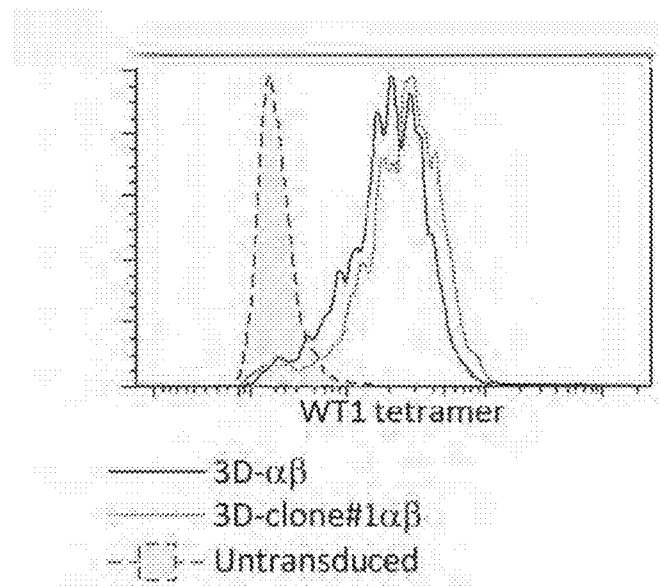

In order to more directly assess the relative affinity of each of the TCRβ chains for MHC-WT1 peptide tetramer, 3Dα+ $58^{-/-}$ cells transduced with 3Dα, and each of the candidate TCRβ chains were stained with six 2-fold serial dilutions of MHC-WT1 peptide tetramer and MFI values were fit to a saturation binding curve by non-linear regression, as the concentration of ligand that yielded half-maximal binding (FIG. 5A). The apparent affinities of all three candidate TCRβ chains, when paired with 3Dα, were found to be higher than the parent 3Dβ, and Clone#1 had ~10 fold higher affinity (FIG. 5A). Therefore, in order directly compare tetramer staining of 3Dα paired with Clone#1 versus the parent 3Dβ, Clone#1 was codon-optimized such that the only sequence differences between the original 3Dβ and Clone#1 were in the CDR3 region. Both constructs were transduced into $58^{-/-}$ cells and assessed by flow cytometry for MHC-WT1 peptide tetramer staining. When Clone#1 was codon-optimized, it was found to bind tetramer at a higher level than the original 3Dβ as expected (FIG. 5B).

Figure 5C:
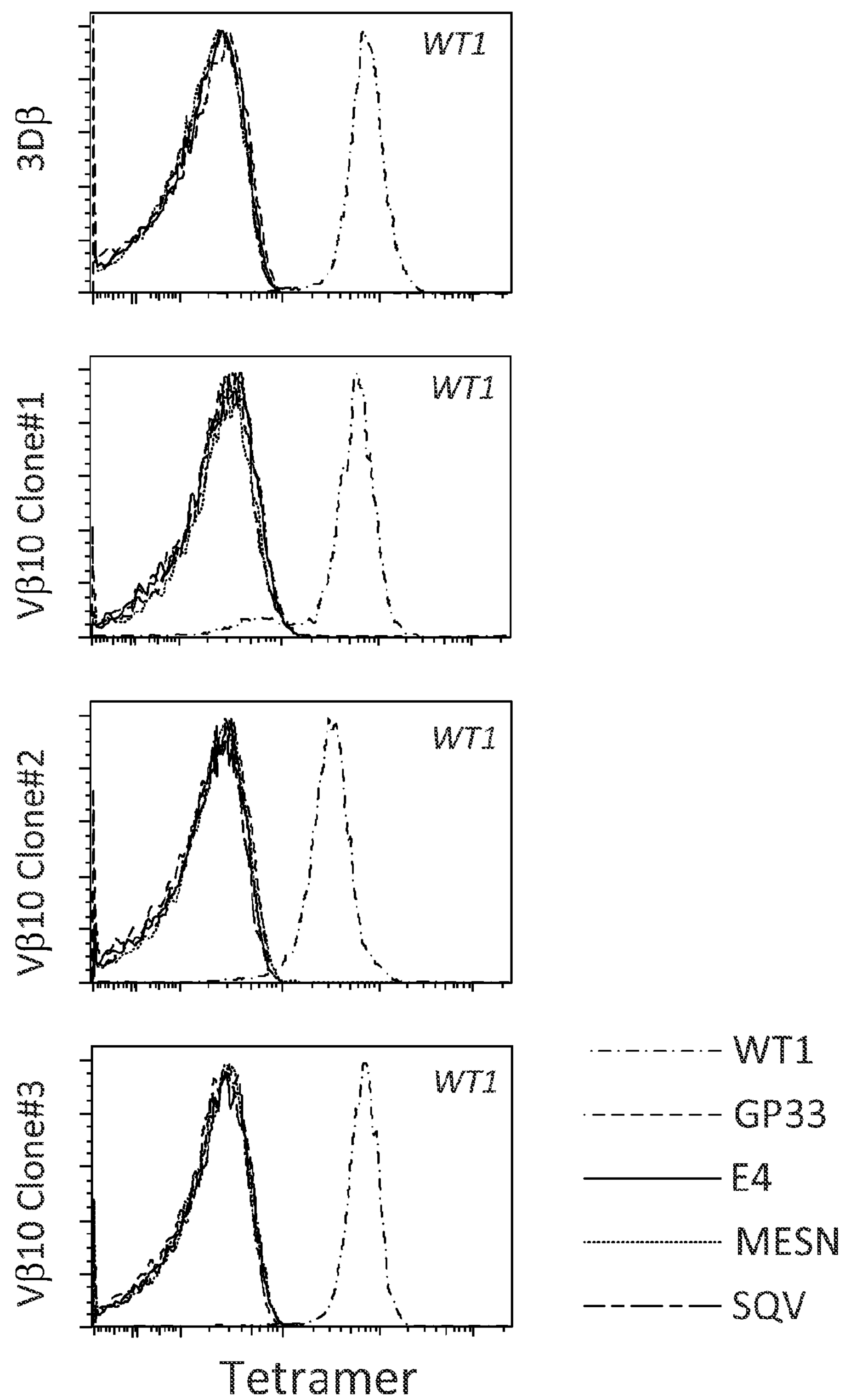

One concern associated with enhancing the affinity of antigen-specific TCRs in vitro is that some modifications might increase the affinity of the receptor for MHC only, rather than peptide/MHC, thereby increasing the likelihood that the TCR will be autoreactive. This risk was minimized by restricting the TCRβ library to TCRβ chains that share the same variable domain (Vb10) in order to restrict variablility to CDR3. In order to determine whether any of the candidate TCRβ chains conferred an increased propensity to bind MHC H-$2D^b$ molecule in a peptide-independent manner, transduced $58^{-/-}$ cells were stained with a panel of MHC H-$2D^b$ tetramers (peptides: WT1, GP33, E4, MESN, SQV). All three candidate TCRβ chains were stained by the MHC-WT1 peptide tetramer at high levels when paired with 3Dα, similar to the original 3Dβ (FIG. 5C). When stained with four other MHC H-$2D^b$-peptide tetramers, all three TCRβ chains were uniformly negative for tetramer staining, suggesting that the increase in affinity observed for these receptors is not the result of an increased affinity for MHC alone (FIG. 5C).

Example 3

Generation of High Affinity WT1-specific T Cells by Ectopic Expression of an Antigen-specific TCRα Chain During Early Human T Cell Development In Vitro The Wilm's tumor (WT1) antigen is expressed at abnormally high levels on the surface of leukemia cells. HLA A2WT1-specific T cell clones have been screened for clones with high specific activity. The TCRα and TCRβ chains from the C4 clone, which was determined to have the highest affinity for WT1, were isolated. A lentiviral vector comprising the C4 TCR and that confers high-level expression is subject of a TCR gene therapy clinical trial scheduled for 2012. In order to further enhance the affinity of the C4 TCR for the WT1 antigen, the in vitro differentiation system described in the previous examples is used with human cord blood progenitor cells expressing the C4 TCRα chain.

Generation of WT1-specific T Cells:

A variant of the OP9-DL1 cell line described in Example 1, which expressed the human Class I MHC molecule HLA-A2 (Genbank Accession Nos. U18930.1 (SEQ ID NO:50) and AAA87076.1 (SEQ ID NO:51), transcript and protein sequences, respectively) and human Class I MHC 132 microglobulin (132M) molecule (Genbank Accession Nos. NM_004048.2 (SEQ ID NO:52) and NP_004039.1 (SEQ ID NO:53), transcript and protein sequences, respectively) was generated. The TCRα chain of the C4 TCR clone is stably transduced into cord blood-derived hematopoietic progenitor cells by retroviral transduction, using a retroviral vector that also encodes green fluorescent protein (GFP) as a transduction marker. Progenitor cells expressing GFP are sorted by flow cytometry and cultured on OP9-DL1-A2/β2M stroma cells in the presence or absence of WT1 peptide RMFPNAPYL (SEQ ID NO:2). Human hematopoietic progenitor cells readily proliferate and differentiate in OP9-DL1 culture to a stage of human T cell development characterized by the phenotype CD34+CD1a+CD4+ (La Motte-Mohs et al., 2005, Blood 105:1431-1439), at which point they are undergoing TCR gene rearrangements at the β, γ, and δ loci (Spits, 2002, Nat. Rev. Immunol. 2:760-772). It is hypothesized that, like their murine counterparts, TCRα-expressing human T cell progenitors that produce an in-frame rearrangement at the TCRβ locus will adapt one of two cell fates: those expressing a TCRβ chain that does not pair well with the transgenic TCRα, or that pairs with the transgenic TCRα but does not receive a strong signal through this αβTCR, will differentiate to the DP stage in response to signaling though the pre-TCR; on the other hand, those that generate a TCRβ chain that can pair with the transgenic TCRα and receive a sufficiently strong signal through this mature αβTCR will be signaled to differentiate towards a DN TCRαβ+ γδ-like lineage. Since DP cells only survive for ~3-4 days without a positive selection signal, and since efficient positive selection does not occur in OP9-DL1 cultures, the vast majority of cells that do not receive an agonist signal through the αβ TCR will be eliminated from the culture, allowing γδ-like cells that develop due to early αβ TCR signaling to accumulate.

Isolation of Candidate TCRβ Chains:

At various points of the culture, non-adherent cells that have a DN TCRαβ+ γδ-like phenotype and are WT1 peptide/A2 MHC-tetramer positive are collected by cell sorting. It may not be possible to detect WT1 tetramer positive cells, as the continued presence of antigen in the cultures may result in TCR down-modulation that could decrease tetramer staining below detection. Furthermore, since these cells are likely not to express CD8αβ, high affinity receptors that are not CD8-independent are undetectable by tetramer staining. Therefore, it may be necessary to screen the TCRβ chains from all DN TCRαβ+ cells that emerge in the culture (see below). It may also be desirable to restrict candidate T cells to those that use the same Vβ segment utilized by the original C4 TCRβ chain (Vβ17), in order to retain the CDR1 and CDR2MHC contacts of the parent C4 TCR.

Following cell sorting, the endogenous TCRβ chains are cloned by purifying total RNA, performing full-length RACE RT-PCR with C-β1 or C-β2 primers, and cloning the PCR products into the pENTR™/D-TOPO® vector (Invitrogen), which allows directional TOPO-cloning and incorporates attL sites that allow rapid and efficient transfer to the retroviral vector Mig-attR (a variant of MigR1 (Pear et al., 1998, Blood 92:3780-3792) that contains attR sites for insertion of gene of interest) using Invitrogen's Gateway® technology recombination system. The products of the recombination reaction are electroporated into high efficiency bacteria, and colonies are scraped together and maxiprepped to generate a retroviral library of potentially WT1-reactive TCRβ chains.

Screening of High Affinity WT1-specific TCRs:

TCRβ chains that can pair with the C4 TCRα chain to form a high affinity WT1-specific TCR are identified by transducing the TCRβ library into the human T cell line H9 (Catalog #HTB-176, ATCC, Manassas, Va.) that has been transduced to express the C4 TCRα chain (H9-C4α). Transduced cells are sorted by flow cytometry for high levels of MHC-WT1 peptide tetramer staining and retroviral inserts will be amplified by PCR from the sorted population. Candidate TCRβ chains are identified by TOPO-cloning of the PCR product followed by sequence analysis. The selected TCRβ chains and the parental C4α are transduced into H9-C4α cells and the relative affinities for the MHC-WT1 peptide tetramer will be calculated by staining transduced cells with serial 2-fold dilutions of PE-conjugated tetramers (as described in Example 2). Affinity values are determined by fitting the MFI for each dilution to a binding curve by non-linear regression and KD defined as tetramer concentration yielding half-maximal binding. TCRβ chains that can pair with C4 TCRα to generate a TCR with higher affinity by MHC-peptide tetramer staining than the wildtype C4 receptor are further characterized for safety and efficacy.

Example 4

Characterization of the Efficacy and Safety of Candidate High Affinity TCRs Using an In Vivo Mouse Model of WT1-targeted TCR Gene Therapy Enhanced affinity human WT1-specific TCRs that are identified as in Example 3 are tested for safety and efficacy in an HLA-A2 transgenic mouse model of WT1 targeted gene therapy.

Assessing Enhanced TCRs for Off-target Activity:

Promiscuous activation of high affinity TCRs are assessed by measuring cytokine production by TCR-transduced T cells in response to a panel of A2 expressing target cells in the presence or absence of WT1 peptide. TCRs that exhibit off-target recognition of WT1 negative target cells compared to the parent C4 TCR are not advanced for further study.

Enhanced Affinity TCRs Activity on Normal Tissue In Vivo:

WT1 expression in normal tissue is similar in both mouse and man, and the WT1 peptide recognized by the C4 TCR is identical in mice and known to be processed and presented by mouse cells (Gaiger et al., 2000, Blood 96:1480-9). HLA-A2 transgenic mice have been used to test for recognition of normal tissues by T cells expressing human high affinity WT1-specific TCRs (Kuball et al., 2009, J. Exp. Med. 206:463-475).

In order to evaluate the safety of enhanced affinity TCRs generated in vitro as disclosed in the previous example, $CD8^+$ T cells from B6.A2/$D^b$ mice, which express a transgene encoding α1 and α2 domains of A2 fused to α3 of $D^b$ (for binding mouse CD8) (Newberg et al., 1996, J. Immunol. 156:2473-2480), are transduced to expressed candidate enhanced affinity TCRs. The TCRs are modified prior to transduction to contain mouse rather than human Cα and Cβ domains, which increases expression in mouse T cells (Pouw et al., 2007, J. Gene Med. 9:561-570). About 4-6 weeks following transfer of TCR-transduced T cells into mice, tissues known to naturally express WT1 (e.g., lungs and kidney) are analyzed by histology for evidence of T cell infiltration and tissue damage, and bone marrow is assessed by flow cytometry for depletion of WT1-expression hematopoietic progenitor cells.

Correlation of Enhanced Affinity with Improved Target Recognition and Function:

There is evidence that an affinity threshold may exist for TCRs, above which further enhancements will not increase T cell function and may actually decrease antigen sensitivity (Schmid et al., 2010, J. Immunol. 184:4936-46). Therefore, the response of high affinity TCR-transduced $CD8^+$ T cells to target cells pulsed with limiting peptide concentrations are compared with T cells expressing the parent C4 TCR. Cytokine production (IFNγ/IL-2) and proliferation, as well as lytic activity, are analyzed. TCRs exhibiting increased affinity and enhanced function are advanced for further study and for potential use in TCR gene therapy trials.

Example 5

Generation of High Affinity WT1-specific T Cells In Vivo

Figure 6:
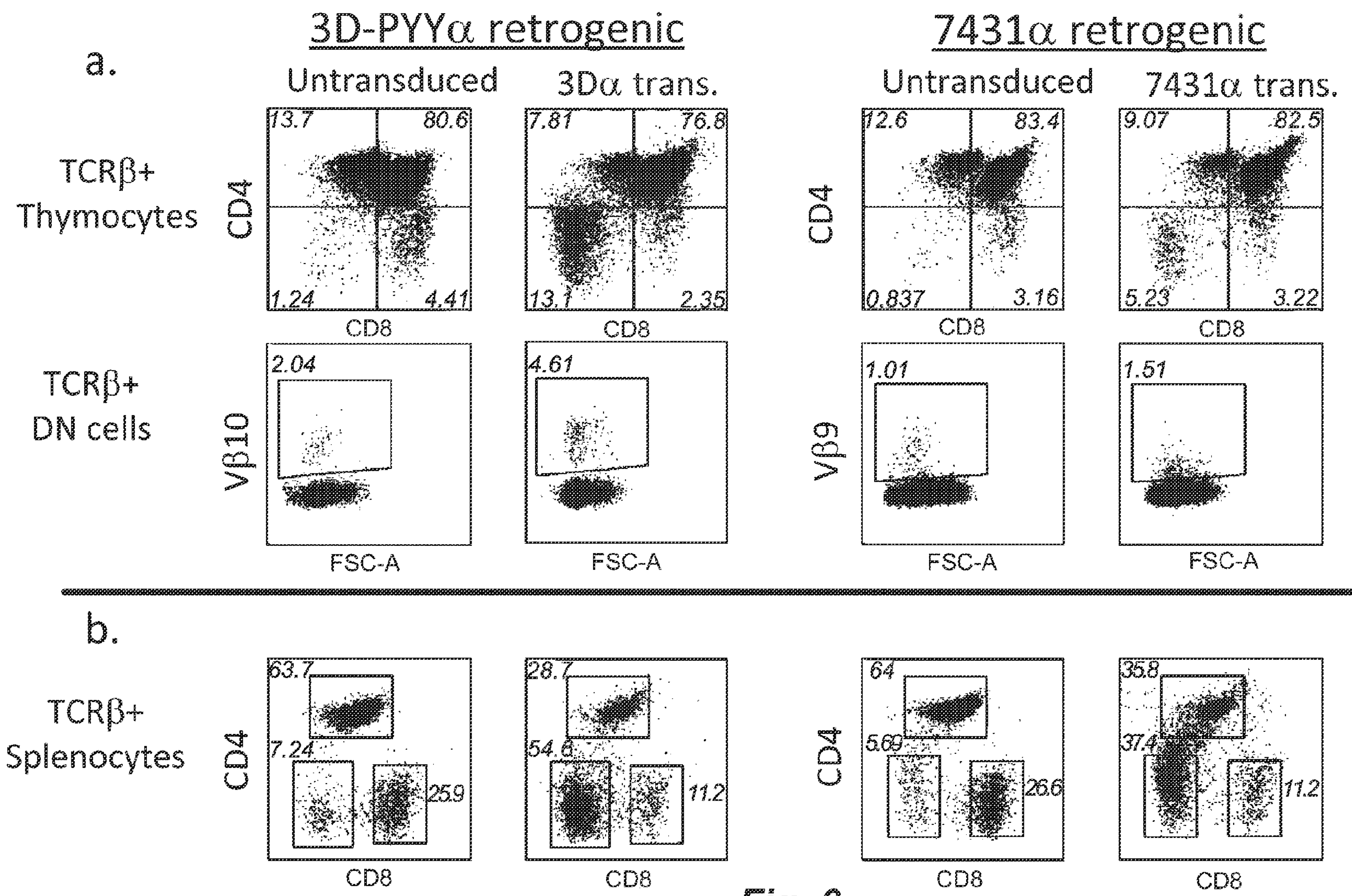
FIGS. 6A-B: Analysis of CD4 and CD8 expression of $TCR\beta^{+}$ thymocytes (A) and splenocytes (B) from 3D-PYYα-IRES-hCD2 and 7431α-IRES-hCD2 retrogenic mice. Vβ10 and Vβ9 expression of $TCR\beta^{+}$ thymocytes (A) from 3D-PYYα-IRES-hCD2 and 7431α-IRES-hCD2 retrogenic mice.

An in vivo mouse model (TCRα retrogenic mice) was used to determine whether $TCRβ^+$ double negative (DN) cells can develop in the thymus. Retrogenic (retrovirally transduced) mice allow for rapid generation, compared with transgenic methods, of mice expressing a specific TCR transgene. Methods of making retrogenic mice are known in the art (see, e.g., Holst et al., 2006, Nat. Protoc. 1:406-417; Holst et al., 2006, Nat. Methods 3:191-197; Bettini et al., 2012, Immunology 136:265-272). Briefly, hematopoietic progenitor/stem cells were purified from the bone marrow of B6 mice and transduced to express the TCRα chain from either the high affinity WT1 specific 3D-PYY TCR or the low affinity mesothelin specific TCR 7431. The 3D-PYY TCR is a higher affinity TCR engineered from the 3D TCR, identified using a T cell display system and selection with WT1/$D^b$ Ig DimerX (BD Biosciences) (Stone et al., 2011, J. Immunol. 186:5193-5200; Chervin et al., 2008, J. Immunol. Methods 339:175-184). The retroviral constructs comprising the 3D-PYY TCRα or 7431α transgenes also include the extracellular domain of human CD2 as a transduction marker, with an IRES between the two transgenes. Transduced bone-marrow derived progenitors were transferred into lethally irradiated B6 host mice to generate bone marrow chimeras expressing the introduced TCRα chains. Six weeks after in vivo transfer of the TCRα-transduced bone marrow cells, mice were sacrificed. Cells from the thymus and spleen were analyzed for CD4 and CD8 expression by flow cytometry (FIGS. 6A, 6B). Analysis of CD4 and CD8 expression by $TCRβ^+$ cells in the thymus (FIG. 6A) shows that a large population of double negative $TCRβ^+$ cells can be detected in vivo in the transduced thymocytes that ectopically express a TCRα chain early in development, and that this population is more pronounced in mice expressing a TCRα from a high affinity TCR (e.g., 3D-PYYα). DN $TCRβ^+$ thymocytes from 3D-PYYα and 7431α retrogenic mice were also analyzed for expression of Vβ10 and Vβ9, respectively (FIG. 6A). These data show that the DN $TCRβ^+$ population is enriched for cells that utilize the same Vβ gene segment as the original antigen specific TCR. Taken together, these data support the hypothesis that the DN TCRβ+ cells develop in response to relatively strong TCR signaling resulting from cognate interactions with the target antigen (i.e., WT1 or Mesothelin) expressed in the thymus. Analysis of CD4 and CD8 expression of TCRβ+ retrogenic splenocytes shows that these DN TCRβ+ cells are also present in the periphery of retrogenic mice (FIG. 6B).

Figure 7:
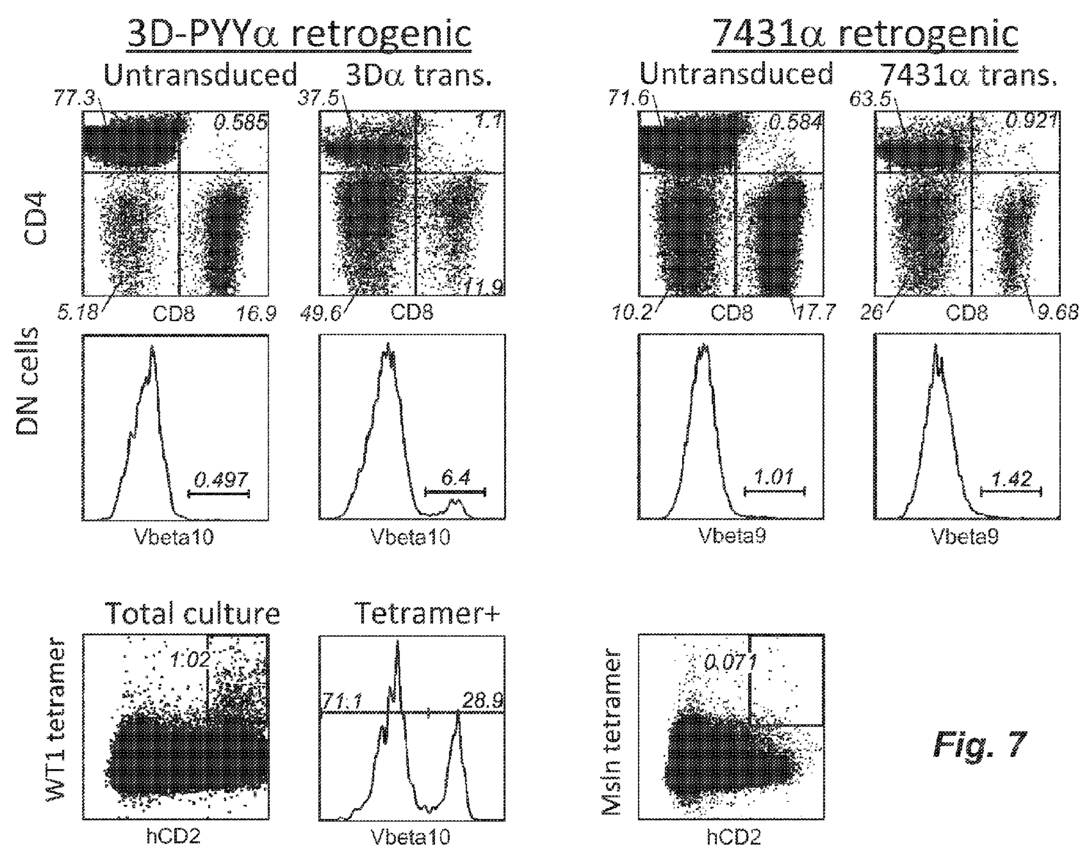
FIG. 7: Analysis of splenocytes from retrogenic mice after 6 days of WT1 of mesothelin peptide stimulation +IL2 in vitro.

Splenocytes from 3D-PYYα and 7431α retrogenic mice were stimulated with WT1 peptide and Mesothelin peptide, receptively, and cultured in vitro in the presence of IL-2 for 6 days. IL-2 was added to the culture in order to potentially expand antigen specific cells so they could be detected by tetramer staining. Cultures were analyzed for CD4 and CD8 expression by flow cytometry within the TCRβ+ gate, as well as for expression of the parental TCR Vβ gene (FIG. 7). Again, enrichment for the parental Vβ gene family is observed, especially for the high affinity 3D-PYY. Cultured T cells were also analyzed for the presence of antigen-specific T cells by staining with WT1 or Mesothelin peptide/MHC tetramers (FIG. 7). These data show that, especially for the high affinity 3D-PYYα retrogenic mice, a significant number of antigen specific T cells are present in these cultures. The fact that the tetramer positive cells are found within the TCRα-transduced ($hCD2^+$) population indicates that these cells developed as a result of the early expression of the TCRα chain. This demonstrates that the DN TCRβ+ cells that develop in these mice actually do contain high affinity antigen specific T cells. Since these are DN cells, they don't have the contribution of CD8 to help with tetramer binding—these TCRs are then "$CD8^-$ independent"—CD8-independent tetramer binding requires a high affinity TCR.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for generating an enhanced affinity T cell receptor (TCR), comprising:

a. contacting one or more hematopoietic progenitor cells with one or more stromal cells and a peptide antigen, under conditions and for a time sufficient to induce differentiation of at least one of the hematopoietic progenitor cells into a double negative (DN) $TCR\alpha\beta^{30}$ thymocyte, wherein the one or more hematopoietic progenitor cells comprise a non-endogenous polynucleotide encoding a TCRα chain from a parent TCR specific for the peptide antigen, and wherein the one or more stromal cells comprise a non-endogenous polynucleotide encoding Delta-like-1 or Delta-like-4 and a polynucleotide encoding an MHC molecule;

b. introducing at least one polynucleotide encoding a TCRβ chain isolated from the DN $TCR\alpha\beta^{+}$thymocyte generated in step (a) into one or more cells that are capable of expressing a TCR on the cell surface and comprise the non-endogenous polynucleotide encoding the TCRα chain from step (a), thereby generating one or more cells expressing a candidate TCR; and c. identifying an enhanced affinity TCR expressed by at least one of the one or more cells generated in step (b), wherein identifying the enhanced affinity TCR comprises comparing the binding affinity of the candidate TCR to the binding affinity of the parent TCR.

2. The method of claim 1, wherein the hematopoietic progenitor cells comprise thymocyte progenitor cells, or the hematopoietic progenitor cells are derived from hematopoietic stem cells.

3. The method of claim 1, wherein the hematopoietic progenitor cells comprise hematopoietic stem cells derived from bone marrow or cord blood.

4. The method of claim 1, wherein a viral vector is used to introduce the non-endogenous polynucleotide encoding the TCRα chain specific for the peptide antigen into the hematopoeitic progenitor cells.

5. The method of claim 4, wherein the viral vector is a retroviral vector or a lentiviral vector.

6. The method of claim 1, wherein the stromal cell expresses Delta-like-1.

7. The method of claim 1, wherein the stromal cell is derived from OP9.

8. The method of claim 1, wherein the method further comprises selecting the cells that are capable of expressing a TCR on the cell surface resulting from step (b) with MHC-peptide tetramer staining one or more times.

9. The method of claim 1, wherein a viral vector is used to introduce the polynucleotides encoding the TCRβ chains from step (b) into the cells that are capable of expressing TCR on the cell surface.

10. The method of claim 9, wherein the viral vector is a retroviral vector or a lentiviral vector.

11. The method of claim 1, wherein the cells that are capable of expressing a TCR on the cell surface are derived from $TCR\alpha^{-}/\beta^{-}58$ T cell hybridoma.

12. The method of claim 1, wherein the enhanced affinity TCR is a human TCR.

13. The method of claim 1, wherein the MHC molecule comprises HLA-A2 and human beta-2-microglobulin (β2M).

14. The method of claim 1, wherein the peptide antigen is selected from the group consisting of: a viral antigen, a bacterial antigen, a cancer antigen, and an autoimmune antigen.

15. The method of claim 14, wherein the peptide antigen is WT1 peptide antigen or mesothelin peptide antigen.

16. The method of claim 15, wherein the WT1 peptide antigen comprises an amino acid sequence RMFPNAPYL (SEQ ID NO:2).

17. The method of claim 15, wherein the mesothelin peptide antigen comprises an amino acid sequence GQKM-NAQAI (SEQ ID NO:31).

18. The method of claim 1, wherein the peptide antigen is added to the hematopoietic progenitor cell and stromal cell in culture.

19. The method of claim 1, wherein the stromal cell comprises a polynucleotide encoding a peptide antigen.

20. The method of claim 1, further comprising prior to the introducing of step (b), isolating the one or more polynucleotides encoding one or more TCRβ chains from the DN TCRαβ+ thymocytes, wherein the isolating comprises selecting one or more TCRβ chains comprising the same $V_\beta$ gene as the β chain of the parent TCR and wherein the introducing comprises introducing at least one of the one or more polynucleotides encoding a selected TCRβ chain into the cell.

* * * * *

UNITED STATES PATENT AND TRADEMARK OFFICE

CERTIFICATE OF CORRECTION

PATENT NO. : 9,751,928 B2
APPLICATION NO. : 14/398206
DATED : September 5, 2017
INVENTOR(S) : Thomas M. Schmitt et al.

It is certified that error appears in the above-identified patent and that said Letters Patent is hereby corrected as shown below:

On the Title Page

Item (56):
"Jun, "Adoptive T cell therapy for cancer in the clinic," *The Journal of Clinical Investigation 117*(6): 1466-1476, 2007." should read, --June, "Adoptive T cell therapy for cancer in the clinic," *The Journal of Clinical Investigation 117*(6):1466-1476, 2007.--.

In the Claims

Column 119, Line 35:
"progenitor cells into a double negative (DN) TCRα$\beta^{30}$" should read, --progenitor cells into a double negative (DN) TCRα$\beta^{+}$--.

Signed and Sealed this
Twentieth Day of February, 2018

Andrei Iancu
*Director of the United States Patent and Trademark Office*

SEQUENCE LISTING

```
<160> NUMBER OF SEQ ID NOS: 53

<210> SEQ ID NO 1
<211> LENGTH: 8
<212> TYPE: PRT
<213> ORGANISM: Artificial Sequence
<220> FEATURE:
<223> OTHER INFORMATION: synthetic ovalbumin peptide

<400> SEQUENCE: 1

Ser Ile Ile Asn Phe Glu Lys Leu
 1              5


<210> SEQ ID NO 2
<211> LENGTH: 9
<212> TYPE: PRT
<213> ORGANISM: Artificial Sequence
<220> FEATURE:
<223> OTHER INFORMATION: Synthetic WT1 peptide

<400> SEQUENCE: 2

Arg Met Phe Pro Asn Ala Pro Tyr Leu
 1              5


<210> SEQ ID NO 3
<211> LENGTH: 3366
<212> TYPE: DNA
<213> ORGANISM: Homo sapiens

<400> SEQUENCE: 3

cgtgggattt ccagaccgcg gctttctaat cggctcggga ggaagctctg cagctctctt     60

gggaattaag ctcaatctct ggactctctc tctttctctt tctcccccte cctctcctgc    120

gaagaagctc aagacaaaac caggaagccg gcgaccctca cctcctcggg ggctgggagg    180

aaggaggaaa acgaaagtcg ccgccgccgc gctgtccccc gagagctgcc tttcctcggg    240

catccctggg gctgccgcgg gacctcgcag ggcggatata aagaaccgcg gccttgggaa    300

gaggcggaga ccggctttta aagaaagaag tcctgggtcc tgcggtctgg ggcgaggcaa    360

gggcgctttt ctgcccacgc tccccgtggc ccatcgatcc cccgcgcgtc cgccgctgtt    420

ctaaggagag aagtgggggc cccccaggct cgcgcgtgga gcgaagcagc atgggcagtc    480
```

```
ggtgcgcgct ggccctggcg gtgctctcgg ccttgctgtg tcaggtctgg agctctgggg    540
tgttcgaact gaagctgcag gagttcgtca acaagaaggg gctgctgggg aaccgcaact    600
gctgccgcgg gggcgcgggg ccaccgccgt gcgcctgccg gaccttcttc cgcgtgtgcc    660
tcaagcacta ccaggccagc gtgtccccg agccgccctg cacctacggc agcgccgtca    720
cccccgtgct gggcgtcgac tccttcagtc tgcccgacgg cgggggcgcc gactccgcgt    780
tcagcaaccc catccgcttc cccttcggct tcacctggcc gggcaccttc tctctgatta    840
ttgaagctct ccacacagat tctcctgatg acctcgcaac agaaaaccca gaaagactca    900
tcagccgcct ggccacccag aggcacctga cggtgggcga ggagtggtcc caggacctgc    960
acagcagcgg ccgcacggac ctcaagtact cctaccgctt cgtgtgtgac gaacactact   1020
acggagaggg ctgctccgtt ttctgccgtc cccgggacga tgccttcggc cacttcacct   1080
gtggggagcg tggggagaaa gtgtgcaacc ctggctggaa agggccctac tgcacagagc   1140
cgatctgcct gcctggatgt gatgagcagc atggattttg tgacaaacca ggggaatgca   1200
agtgcagagt gggctggcag ggccggtact gtgacgagtg tatccgctat ccaggctgtc   1260
tccatggcac ctgccagcag ccctggcagt gcaactgcca ggaaggctgg gggggccttt   1320
tctgcaacca ggacctgaac tactgcacac accataagcc ctgcaagaat ggagccacct   1380
gcaccaacac gggccagggg agctacactt gctcttgccg gcctgggtac acaggtgcca   1440
cctgcgagct ggggattgac gagtgtgacc ccagcccttg taagaacgga gggagctgca   1500
cggatctcga gaacagctac tcctgtacct gcccacccgg cttctacggc aaaatctgtg   1560
aattgagtgc catgacctgt gcggacggcc cttgctttaa cgggggtcgg tgctcagaca   1620
gccccgatgg agggtacagc tgccgctgcc ccgtgggcta ctccggcttc aactgtgaga   1680
agaaaattga ctactgcagc tcttcaccct gttctaatgg tgccaagtgt gtggacctcg   1740
gtgatgccta cctgtgccgc tgccaggccg gcttctcggg gaggcactgt gacgacaacg   1800
tggacgactg cgcctcctcc ccgtgcgcca acgggggcac ctgccgggat ggcgtgaacg   1860
acttctcctg cacctgcccg cctggctaca cgggcaggaa ctgcagtgcc cccgtcagca   1920
ggtgcgagca cgcaccctgc cacaatgggg ccacctgcca cgagaggggc caccgctatg   1980
tgtgcgagtg tgcccgaggc tacgggggtc ccaactgcca gttcctgctc cccgagctgc   2040
ccccgggccc agcggtggtg gacctcactg agaagctaga gggccagggc gggccattcc   2100
cctgggtggc cgtgtgcgcc ggggtcatcc ttgtcctcat gctgctgctg ggctgtgccg   2160
ctgtggtggt ctgcgtccgg ctgaggctgc agaagcaccg gcccccagcc gacccctgcc   2220
ggggggagac ggagaccatg aacaacctgg ccaactgcca gcgtgagaag gacatctcag   2280
tcagcatcat cggggccacg cagatcaaga acaccaacaa gaaggcggac ttccacgggg   2340
accacagcgc cgacaagaat ggcttcaagg cccgctaccc agcggtggac tataacctcg   2400
tgcaggacct caagggtgac gacaccgccg tcagggacgc gcacagcaag cgtgacacca   2460
agtgccagcc ccagggctcc tcaggggagg agaaggggac cccgaccaca ctcaggggtg   2520
gagaagcatc tgaaagaaaa aggccggact cgggctgttc aacttcaaaa gacaccaagt   2580
accagtcggt gtacgtcata tccgaggaga aggatgagtg cgtcatagca actgaggtgt   2640
aaaatggaag tgagatggca agactcccgt ttctcttaaa ataagtaaaa ttccaaggat   2700
atatgcccca acgaatgctg ctgaagagga gggaggcctc gtggactgct gctgagaaac   2760
cgagttcaga ccgagcaggt tctcctcctg aggtcctcga cgcctgccga cagcctgtcg   2820
```

```
cggcccggcc gcctgcggca ctgccttccg tgacgtcgcc gttgcactat ggacagttgc   2880

tcttaagaga atatatattt aaatgggtga actgaattac gcataagaag catgcactgc   2940

ctgagtgtat attttggatt cttatgagcc agtcttttct tgaattagaa acacaaacac   3000

tgcctttatt gtcctttttg atacgaagat gtgctttttc tagatggaaa agatgtgtgt   3060

tatttttgg atttgtaaaa atatttttca tgatatctgt aaagcttgag tattttgtga   3120

tgttcgtttt ttataattta aattttggta aatatgtaca aaggcacttc gggtctatgt   3180

gactatattt ttttgtatat aaatgtattt atggaatatt gtgcaaatgt tatttgagtt   3240

ttttactgtt ttgttaatga agaaattcct ttttaaaata tttttccaaa ataaatttta   3300

tgaatgacaa aaaaaaaaaa aaaaaaaaaa aaaaaaaaaa aaaaaaaaaa aaaaaaaaaa   3360

aaaaaa                                                              3366


<210> SEQ ID NO 4
<211> LENGTH: 723
<212> TYPE: PRT
<213> ORGANISM: Homo sapiens

<400> SEQUENCE: 4

Met Gly Ser Arg Cys Ala Leu Ala Leu Ala Val Leu Ser Ala Leu Leu
 1               5                  10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270
```

```
Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
    370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
                405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
    450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
                485                 490                 495

His Glu Arg Gly His Arg Tyr Val Cys Glu Cys Ala Arg Gly Tyr Gly
            500                 505                 510

Gly Pro Asn Cys Gln Phe Leu Leu Pro Glu Leu Pro Pro Gly Pro Ala
        515                 520                 525

Val Val Asp Leu Thr Glu Lys Leu Glu Gly Gln Gly Gly Pro Phe Pro
    530                 535                 540

Trp Val Ala Val Cys Ala Gly Val Ile Leu Val Leu Met Leu Leu Leu
545                 550                 555                 560

Gly Cys Ala Ala Val Val Val Cys Val Arg Leu Arg Leu Gln Lys His
                565                 570                 575

Arg Pro Pro Ala Asp Pro Cys Arg Gly Glu Thr Glu Thr Met Asn Asn
            580                 585                 590

Leu Ala Asn Cys Gln Arg Glu Lys Asp Ile Ser Val Ser Ile Ile Gly
        595                 600                 605

Ala Thr Gln Ile Lys Asn Thr Asn Lys Lys Ala Asp Phe His Gly Asp
    610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
        675                 680                 685

Arg Lys Arg Pro Asp Ser Gly Cys Ser Thr Ser Lys Asp Thr Lys Tyr
```

-continued 690 695 700

Gln Ser Val Tyr Val Ile Ser Glu Glu Lys Asp Glu Cys Val Ile Ala
705 710 715 720

Thr Glu Val

<210> SEQ ID NO 5
<211> LENGTH: 3444
<212> TYPE: DNA
<213> ORGANISM: Mus musculus

<400> SEQUENCE: 5
cttggcgata gtgcaagaga taccggtcta gaacactctg ggagcggcag cggctgccga 60
gtgacgccgg gccgggaaac cagggcgcgc gccgcagtcc ttgccaccac cgttcccacc 120
gcgcccctcg ggccccgga ttatcgcctc accggtggga tttccagacc gccgcttcct 180
aataggcctg cgaaggaagc cactgcaagc tctcttggga attaagctga acatctgggc 240
tctcttccct ctgtgtctta tctcctttct cctctttccc tccgcgaaga agcttaagac 300
aaaaccagaa agcaggagac actcacctct ccgtggactg aaagccagac gaagaggaaa 360
ccgaaagttg tcctttctca gtgcctcgta gagctcttgc cggggaccta gctgaaggca 420
ccgcaccctc ctgaagcgac ctggccctga tagcacacct ggagccgaga gacgcctttc 480
cgccagtact cctcgggtca tatagacttt cctggcatcc ctgggtcttt gaagaagaaa 540
gaaaagagga tactctagga gagcaagggc gtccagcggt accatgggcc gtcggagcgc 600
gctagccctt gccgtggtct ctgccctgct gtgccaggtc tggagctccg gcgtatttga 660
gctgaagctg caggagttcg tcaacaagaa ggggctgctg gggaaccgca actgctgccg 720
cgggggctct ggcccgcctt gcgcctgcag gaccttcttt cgcgtatgcc tcaagcacta 780
ccaggccagc gtgtcaccgg agccaccctg cacctacggc agtgctgtca cgccagtgct 840
gggtgtcgac tccttcagcc tgcctgatgg cgcaggcatc gaccccgcct tcagcaaccc 900
catccgattc cccttcggct tcacctggcc aggtaccttc tctctgatca ttgaagccct 960
ccatacagac tctcccgatg acctcgcaac agaaaaccca gaaagactca tcagccgcct 1020
gaccacacag aggcacctca ctgtgggaga agaatggtct caggaccttc acagtagcgg 1080
ccgcacagac ctccggtact cttaccggtt tgtgtgtgac gagcactact acggagaagg 1140
ttgctctgtg ttctgccgac ctcgggatga cgcctttggc cacttcacct gcggggacag 1200
aggggagaag atgtgcgacc ctggctggaa aggccagtac tgcactgacc caatctgtct 1260
gccagggtgt gatgaccaac atggatactg tgacaaacca ggggagtgca agtgcagagt 1320
tggctggcag ggccgctact gcgatgagtg catccgatac ccaggttgtc tccatggcac 1380
ctgccagcaa ccctggcagt gtaactgcca ggaaggctgg gggggccttt tctgcaacca 1440
agacctgaac tactgtactc accataagcc gtgcaggaat ggagccacct gcaccaacac 1500
gggccagggg agctacacat gttcctgccg acctgggtat acaggtgcca actgtgagct 1560
ggaagtagat gagtgtgctc ctagcccctg caagaacgga gcgagctgca cggaccttga 1620
ggacagcttc tcttgcacct gccctcccgg cttctatggc aaggtctgtg agctgagcgc 1680
catgacctgt gcagatggcc cttgcttcaa tggaggacga tgttcagata accctgacgg 1740
aggctacacc tgccattgcc ccttgggctt ctctggcttc aactgtgaga agaagatgga 1800
tctctgcggc tcttcccctt gttctaacgg tgccaagtgt gtggacctcg gcaactctta 1860
cctgtgccgg tgccaggctg gcttctccgg gaggtactgc gaggacaatg tggatgactg 1920

-continued

```
tgcctcctcc ccgtgtgcaa atgggggcac ctgccgggac agtgtgaacg acttctcctg   1980

tacctgccca cctggctaca cgggcaagaa ctgcagcgcc cctgtcagca ggtgtgagca   2040

tgcaccctgc cataatgggg ccacctgcca ccagaggggc cagcgctaca tgtgtgagtg   2100

cgcccagggc tatggcggcc ccaactgcca gtttctgctc cctgagccac caccagggcc   2160

catggtggtg gacctcagtg agaggcatat ggagagccag ggcgggccct tcccctgggt   2220

ggccgtgtgt gccggggtgg tgcttgtcct cctgctgctg ctgggctgtg ctgctgtggt   2280

ggtctgcgtc cggctgaagc tacagaaaca ccagcctcca cctgaaccct gtgggggaga   2340

gacagaaacc atgaacaacc tagccaattg ccagcgcgag aaggacgttt ctgttagcat   2400

cattggggct acccagatca agaacaccaa caagaaggcg gactttcacg gggaccatgg   2460

agccgagaag agcagcttta aggtccgata ccccactgtg gactataacc tcgttcgaga   2520

cctcaaggga gatgaagcca cggtcaggga tacacacagc aaacgtgaca ccaagtgcca   2580

gtcacagagc tctgcaggag aagagaagat cgccccaaca cttaggggtg ggagattcc    2640

tgacagaaaa aggccagagt ctgtctactc tacttcaaag gacaccaagt accagtcggt   2700

gtatgttctg tctgcagaaa aggatgagtg tgttatagcg actgaggtgt aagatggaag   2760

cgatgtggca aaattcccat ttctcttaaa taaaattcca aggatatagc cccgatgaat   2820

gctgctgaga gaggaaggga gaggaaaccc agggactgct gctgagaacc aggttcaggc   2880

gaagctggtt ctctcagagt tagcagaggc gcccgacact gccagcctag gctttggctg   2940

ccgctggact gcctgctggt tgttcccatt gcactatgga cagttgcttt gaagagtata   3000

tatttaaatg gacgagtgac ttgattcata taggaagcac gcactgccca cacgtctatc   3060

ttggattact atgagccagt ctttccttga actagaaaca caactgcctt tattgtcctt   3120

tttgatactg agatgtgttt tttttttcc tagacgggaa aaagaaaacg tgtgttattt    3180

ttttgggatt tgtaaaaata tttttcatga tatctgtaaa gcttgagtat tttgtgacgt   3240

tcattttttt ataatttaaa ttttggtaaa tatgtacaaa ggcacttcgg gtctatgtga   3300

ctatattttt ttgtatataa atgtatttat ggaatattgt gcaaatgtta tttgagtttt   3360

ttactgtttt gttaatgaag aaattcattt taaaaatatt tttccaaaat aaatataatg   3420

aactacaaaa aaaaaaaaaa aaaa                                          3444


<210> SEQ ID NO 6
<211> LENGTH: 722
<212> TYPE: PRT
<213> ORGANISM: Mus musculus

<400> SEQUENCE: 6

Met Gly Arg Arg Ser Ala Leu Ala Leu Ala Val Val Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ser Gly Pro Pro Cys Ala Cys Arg Thr Phe Phe Arg Val Cys Leu Lys
    50                  55                  60

His Tyr Gln Ala Ser Val Ser Pro Glu Pro Pro Cys Thr Tyr Gly Ser
65                  70                  75                  80

Ala Val Thr Pro Val Leu Gly Val Asp Ser Phe Ser Leu Pro Asp Gly
                85                  90                  95

Ala Gly Ile Asp Pro Ala Phe Ser Asn Pro Ile Arg Phe Pro Phe Gly
```

-continued

```
            100                 105                 110

Phe Thr Trp Pro Gly Thr Phe Ser Leu Ile Ile Glu Ala Leu His Thr
        115                 120                 125

Asp Ser Pro Asp Asp Leu Ala Thr Glu Asn Pro Glu Arg Leu Ile Ser
    130                 135                 140

Arg Leu Thr Thr Gln Arg His Leu Thr Val Gly Glu Glu Trp Ser Gln
145                 150                 155                 160

Asp Leu His Ser Ser Gly Arg Thr Asp Leu Arg Tyr Ser Tyr Arg Phe
                165                 170                 175

Val Cys Asp Glu His Tyr Tyr Gly Glu Gly Cys Ser Val Phe Cys Arg
            180                 185                 190

Pro Arg Asp Asp Ala Phe Gly His Phe Thr Cys Gly Asp Arg Gly Glu
        195                 200                 205

Lys Met Cys Asp Pro Gly Trp Lys Gly Gln Tyr Cys Thr Asp Pro Ile
    210                 215                 220

Cys Leu Pro Gly Cys Asp Asp Gln His Gly Tyr Cys Asp Lys Pro Gly
225                 230                 235                 240

Glu Cys Lys Cys Arg Val Gly Trp Gln Gly Arg Tyr Cys Asp Glu Cys
                245                 250                 255

Ile Arg Tyr Pro Gly Cys Leu His Gly Thr Cys Gln Gln Pro Trp Gln
            260                 265                 270

Cys Asn Cys Gln Glu Gly Trp Gly Gly Leu Phe Cys Asn Gln Asp Leu
        275                 280                 285

Asn Tyr Cys Thr His His Lys Pro Cys Arg Asn Gly Ala Thr Cys Thr
    290                 295                 300

Asn Thr Gly Gln Gly Ser Tyr Thr Cys Ser Cys Arg Pro Gly Tyr Thr
305                 310                 315                 320

Gly Ala Asn Cys Glu Leu Glu Val Asp Glu Cys Ala Pro Ser Pro Cys
                325                 330                 335

Lys Asn Gly Ala Ser Cys Thr Asp Leu Glu Asp Ser Phe Ser Cys Thr
            340                 345                 350

Cys Pro Pro Gly Phe Tyr Gly Lys Val Cys Glu Leu Ser Ala Met Thr
        355                 360                 365

Cys Ala Asp Gly Pro Cys Phe Asn Gly Gly Arg Cys Ser Asp Asn Pro
    370                 375                 380

Asp Gly Gly Tyr Thr Cys His Cys Pro Leu Gly Phe Ser Gly Phe Asn
385                 390                 395                 400

Cys Glu Lys Lys Met Asp Leu Cys Gly Ser Ser Pro Cys Ser Asn Gly
                405                 410                 415

Ala Lys Cys Val Asp Leu Gly Asn Ser Tyr Leu Cys Arg Cys Gln Ala
            420                 425                 430

Gly Phe Ser Gly Arg Tyr Cys Glu Asp Asn Val Asp Asp Cys Ala Ser
        435                 440                 445

Ser Pro Cys Ala Asn Gly Gly Thr Cys Arg Asp Ser Val Asn Asp Phe
    450                 455                 460

Ser Cys Thr Cys Pro Pro Gly Tyr Thr Gly Lys Asn Cys Ser Ala Pro
465                 470                 475                 480

Val Ser Arg Cys Glu His Ala Pro Cys His Asn Gly Ala Thr Cys His
                485                 490                 495

Gln Arg Gly Gln Arg Tyr Met Cys Glu Cys Ala Gln Gly Tyr Gly Gly
            500                 505                 510

Pro Asn Cys Gln Phe Leu Leu Pro Glu Pro Pro Pro Gly Pro Met Val
        515                 520                 525
```

```
Val Asp Leu Ser Glu Arg His Met Glu Ser Gln Gly Gly Pro Phe Pro
    530                 535                 540

Trp Val Ala Val Cys Ala Gly Val Val Leu Val Leu Leu Leu Leu Leu
545                 550                 555                 560

Gly Cys Ala Ala Val Val Val Cys Val Arg Leu Lys Leu Gln Lys His
                565                 570                 575

Gln Pro Pro Pro Glu Pro Cys Gly Gly Glu Thr Glu Thr Met Asn Asn
            580                 585                 590

Leu Ala Asn Cys Gln Arg Glu Lys Asp Val Ser Val Ser Ile Ile Gly
        595                 600                 605

Ala Thr Gln Ile Lys Asn Thr Asn Lys Lys Ala Asp Phe His Gly Asp
    610                 615                 620

His Gly Ala Glu Lys Ser Ser Phe Lys Val Arg Tyr Pro Thr Val Asp
625                 630                 635                 640

Tyr Asn Leu Val Arg Asp Leu Lys Gly Asp Glu Ala Thr Val Arg Asp
                645                 650                 655

Thr His Ser Lys Arg Asp Thr Lys Cys Gln Ser Gln Ser Ser Ala Gly
            660                 665                 670

Glu Glu Lys Ile Ala Pro Thr Leu Arg Gly Gly Glu Ile Pro Asp Arg
        675                 680                 685

Lys Arg Pro Glu Ser Val Tyr Ser Thr Ser Lys Asp Thr Lys Tyr Gln
    690                 695                 700

Ser Val Tyr Val Leu Ser Ala Glu Lys Asp Glu Cys Val Ile Ala Thr
705                 710                 715                 720

Glu Val


<210> SEQ ID NO 7
<211> LENGTH: 3420
<212> TYPE: DNA
<213> ORGANISM: Homo sapiens

<400> SEQUENCE: 7

aggtttcagt agcggcgctg cgcgcaggcc gggaacacga ggccaagagc cgcagcccca      60

gccgccttgg tgcagcgtac accggcacta gcccgcttgc agccccagga ttagacagaa     120

gacgcgtcct cggcgcggtc gccgcccagc cgtagtcacc tggattacct acagcggcag     180

ctgcagcgga gccagcgaga aggccaaagg ggagcagcgt cccgagagga gcgcctcttt     240

tcagggaccc cgccggctgg cggacgcgcg ggaaagcggc gtcgcgaaca gagccagatt     300

gagggcccgc gggtggagag agcgacgccc gaggggatgg cggcagcgtc ccggagcgcc     360

tctggctggg cgctactgct gctggtggca ctttggcagc agcgcgcggc cggctccggc     420

gtcttccagc tgcagctgca ggagttcatc aacgagcgcg gcgtactggc cagtgggcgg     480

ccttgcgagc ccggctgccg gactttcttc cgcgtctgcc ttaagcactt ccaggcggtc     540

gtctcgcccg gaccctgcac cttcgggacc gtctccacgc cggtattggg caccaactcc     600

ttcgctgtcc gggacgacag tagcggcggg gggcgcaacc ctctccaact gcccttcaat     660

ttcacctggc cgggtacctt ctcgctcatc atcgaagctt ggcacgcgcc aggagacgac     720

ctgcggccag aggccttgcc accagatgca ctcatcagca agatcgccat ccagggctcc     780

ctagctgtgg gtcagaactg gttattggat gagcaaacca gcaccctcac aaggctgcgc     840

tactcttacc gggtcatctg cagtgacaac tactatggag acaactgctc ccgcctgtgc     900

aagaagcgca atgaccactt cggccactat gtgtgccagc cagatggcaa cttgtcctgc     960
```

-continued

```
ctgcccggtt ggactgggga atattgccaa cagcctatct gtctttcggg ctgtcatgaa   1020
cagaatggct actgcagcaa gccagcagag tgcctctgcc gcccaggctg gcagggccgg   1080
ctgtgtaacg aatgcatccc ccacaatggc tgtcgccacg gcacctgcag cactccctgg   1140
caatgtactt gtgatgaggg ctggggaggc ctgttttgtg accaagatct caactactgc   1200
acccaccact ccccatgcaa gaatggggca acgtgctcca acagtgggca gcgaagctac   1260
acctgcacct gtcgcccagg ctacactggt gtggactgtg agctggagct cagcgagtgt   1320
gacagcaacc cctgtcgcaa tggaggcagc tgtaaggacc aggaggatgg ctaccactgc   1380
ctgtgtcctc cgggctacta tggcctgcat tgtgaacaca gcaccttgag ctgcgccgac   1440
tcccccctgct tcaatggggg ctcctgccgg gagcgcaacc agggggccaa ctatgcttgt   1500
gaatgtcccc ccaacttcac cggctccaac tgcgagaaga aagtggacag gtgcaccagc   1560
aacccctgtg ccaacggggg acagtgcctg aaccgaggtc caagccgcat gtgccgctgc   1620
cgtcctggat tcacgggcac ctactgtgaa ctccacgtca gcgactgtgc ccgtaaccct   1680
tgcgcccacg gtggcacttg ccatgacctg gagaatggcc tcatgtgcac ctgccctgcc   1740
ggcttctctg gccgacgctg tgaggtgcgg acatccatcg atgcctgtgc ctcgagtccc   1800
tgcttcaaca gggccacctg ctacaccgac ctctccacag acacctttgt gtgcaactgc   1860
ccttatggct ttgtgggcag ccgctgcgag ttccccgtgg gcttgccgcc cagcttcccc   1920
tgggtggccg tctcgctggg tgtggggctg gcagtgctgc tggtactgct gggcatggtg   1980
gcagtggctg tgcggcagct gcggcttcga cggccggacg acggcagcag ggaagccatg   2040
aacaacttgt cggacttcca gaaggacaac ctgattcctg ccgcccagct taaaaacaca   2100
aaccagaaga aggagctgga agtggactgt ggcctggaca agtccaactg tggcaaacag   2160
caaaaccaca cattggacta taatctggcc ccagggcccc tggggcgggg gaccatgcca   2220
ggaaagtttc cccacagtga caagagctta ggagagaagg cgccactgcg gttacacagt   2280
gaaaagccag agtgtcggat atcagcgata tgctccccca gggactccat gtaccagtct   2340
gtgtgtttga tatcagagga gaggaatgaa tgtgtcattg ccacggaggt ataaggcagg   2400
agcctacctg gacatccctg ctcagccccg cggctggacc ttccttctgc attgtttaca   2460
ttgcatcctg gatgggacgt tttcatatg caacgtgctg ctctcaggag gaggagggaa   2520
tggcaggaac cggacagact gtgaacttgc caagagatgc aataccctttc cacacctttg   2580
ggtgtctgtc tggcatcaga ttggcagctg caccaaccag aggaacagaa gagaagagag   2640
atgccactgg gcactgccct gccagtagtg gccttcaggg ggctccttcc ggggctccgg   2700
cctgttttcc agagagagtg gcagtagccc catggggccc ggagctgctg tggcctccac   2760
tggcatccgt gtttccaaaa gtgcctttgg cccaggctcc acggcgacag ttgggcccaa   2820
atcagaaagg agagaggggg ccaatgaggg cagggcctcc tgtgggctgg aaaaccactg   2880
ggtgcgtctc ttgctggggt ttgccctgga ggtgaggtga gtgctcgagg gaggggagtg   2940
ctttctgccc catgcctcca actactgtat gcaggcctgg ctctctggtc taggcccttt   3000
gggcaagaat gtccgtctac ccggcttcca ccaccctctg gccctgggct tctgtaagca   3060
gacaggcaga gggcctgccc ctcccaccag ccaagggtgc caggcctaac tggggcactc   3120
agggcagtgt gttggaaatt ccactgaggg ggaaatcagg tgctgcggcc gcctgggccc   3180
tttcctccct caagcccatc tccacaacct cgagcctggg ctctggtcca ctactgcccc   3240
agaccaccct caaagctggt cttcagaaat caataatatg agtttttatt ttgttttttt   3300
ttttttttt gtagtttatt ttggagtcta gtatttcaat aatttaagaa tcagaagcac   3360
```

```
tgacctttct acattttata acattatttt gtatataatg tgtatttata atatgaaaca   3420


<210> SEQ ID NO 8
<211> LENGTH: 685
<212> TYPE: PRT
<213> ORGANISM: Homo sapiens

<400> SEQUENCE: 8

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365
```

```
Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685
```

<210> SEQ ID NO 9
<211> LENGTH: 3451
<212> TYPE: DNA
<213> ORGANISM: Mus musculus

<400> SEQUENCE: 9

```
atataagaaa ggctctggag caagcaggtt tcagtagcgg cgctgctcgc aggctaggaa      60

cccgaggcca agagctgcag ccaaagtcac ttgggtgcag tgtactccct cactagcccg     120

ctcgagaccc taggatttgc tccaggacac gtacttagag cagccaccgc ccagtcgccc     180

tcacctggat tacctaccga ggcatcgagc agcggagttt ttgagaaggc gacaagggag     240

cagcgtcccg aggggaatca gcttttcagg aactcggctg gcagacggga cttgcgggag     300
```

-continued

```
agcgacatcc ctaacaagca gattcggagt cccggagtgg agaggacacc ccaagggatg    360
acgcctgcgt cccggagcgc ctgtcgctgg gcgctactgc tgctggcggt actgtggccg    420
cagcagcgcg ctgcgggctc cggcatcttc cagctgcggc tgcaggagtt cgtcaaccag    480
cgcggtatgc tggccaatgg gcagtcctgc gaaccgggct gccggacttt cttccgcatc    540
tgccttaagc acttccaggc aaccttctcc gagggaccct gcacctttgg caatgtctcc    600
acgccggtat tgggcaccaa ctccttcgtc gtcagggaca agaatagcgg cagtggtcgc    660
aaccctctgc agttgccctt caatttcacc tggccgggaa ccttctcact caacatccaa    720
gcttggcaca caccgggaga cgacctgcgg ccagagactt cgccaggaaa ctctctcatc    780
agccaaatca tcatccaagg ctctcttgct gtgggtaaga tttggcgaac agacgagcaa    840
aatgacaccc tcaccagact gagctactct taccgggtca tctgcagtga caactactat    900
ggagagagct gttctcgcct atgcaagaag cgcgatgacc acttcggaca ttatgagtgc    960
cagccagatg gcagcctgtc ctgcctgccg ggctggactg ggaagtactg tgaccagcct   1020
atatgtcttt ctggctgtca tgagcagaat ggttactgca gcaagccaga tgagtgcatc   1080
tgccgtccag gttggcaggg tcgcctgtgc aatgaatgta tcccccacaa tggctgtcgt   1140
catggcacct gcagcatccc ctggcagtgt gcctgcgatg agggatgggg aggtctgttt   1200
tgtgaccaag atctcaacta ctgtactcac cactctccgt gcaagaatgg atcaacgtgt   1260
tccaacagtg ggccaaaggg ttatacctgc acctgtctcc caggctacac tggtgagcac   1320
tgtgagctgg gactcagcaa gtgtgccagc aacccctgtc gaaatggtgg cagctgtaag   1380
gaccaggaga atagctacca ctgcctgtgt cccccaggct actatggcca gcactgtgag   1440
catagtacct tgacctgcgc ggactcaccc tgcttcaatg gggctcttg ccgggagcgc    1500
aaccaggggt ccagttatgc ctgcgaatgc ccccccaact ttaccggctc taactgtgag   1560
aagaaagtag acaggtgtac cagcaacccg tgtgccaatg gaggccagtg ccagaacaga   1620
ggtccaagcc gaacctgccg ctgccggcct ggattcacag gcacccactg tgaactgcac   1680
atcagcgatt gtgcccgaag tccctgtgcc cacgggggca cttgccacga tctggagaat   1740
gggcctgtgt gcacctgccc cgctggcttc tctggaaggc gctgcgaggt gcggataacc   1800
cacgatgcct gtgcctccgg accctgcttc aatggggcca cctgctacac tggcctctcc   1860
ccaaacaact tcgtctgcaa ctgtccttat ggctttgtgg gcagccgctg cgagtttccc   1920
gtgggcttgc cacccagctt cccctgggta gctgtctcgc tgggcgtggg gctagtggta   1980
ctgctggtgc tcctggtcat ggtggtagtg gctgtgcggc agctgcggct tcggaggccc   2040
gatgacgaga gcagggaagc catgaacaat ctgtcagact tccagaagga caacctaatc   2100
cctgccgccc agctcaaaaa cacaaaccag aagaaggagc tggaagtgga ctgtggtctg   2160
gacaagtcca attgtggcaa actgcagaac cacacattgg actacaatct agccccggga   2220
ctcctaggac ggggcggcat gcctgggaag tatcctcaca gtgacaagag cttaggagag   2280
aaggtgccac ttcggttaca cagtgagaag ccagagtgtc gaatatcagc catttgctct   2340
cccagggact ctatgtacca atcagtgtgt ttgatatcag aagagaggaa cgagtgtgtg   2400
attgccacag aggtataagg caggagccta ctcagacacc cagctccggc ccagcagctg   2460
ggccttcctt ctgcattgtt tacattgcat cctgtatggg acatctttag tatgcacagt   2520
gctgctctgc ggaggaggag gaaatggcat gaactgaaca gactgtgaac ccgccaagag   2580
tcgcaccggc tctgcacacc tccaggagtc tgcctggctt cagatgggca gccccgccaa   2640
gggaacagag ttgaggagtt agaggagcat cagttgagct gatatctaag gtgcctctcg   2700
```

```
aacttggact tgctctgcca acagtggtca tcatggagct cttgactgtt ctccagagag   2760

tggcagtggc cctagtgggt cttggcgctg ctgtagctcc tgtgggcatc tgtatttcca   2820

aagtgccttt gcccagactc catcctcaca gctgggccca aatgagaaag cagagaggag   2880

gcttgcaaag gataggcctc ccgcaggcag aacagccttg gagtttggca ttaagcagga   2940

gctactctgc aggtgaggaa agcccgagga ggggacacgt gtgactcctg cctccaaccc   3000

cagtaggtgg agtgccacct gtagcctcta ggcaagagtt ggtccttccc ctggtcctgg   3060

tgcctctggg ctcatgtgaa cagatgggct tagggcacgc ccttttgcc agccaggggt    3120

acaggcctca ctggggagct cagggccttc atgctaaact cccaataagg gagatggggg   3180

gaagggggct gtggcctagg cccttccctc cctcacaccc atttctgggc ccttgagcct   3240

gggctccacc agtgcccact gctgccccga gaccaacctt gaagccgatc ttcaaaaatc   3300

aataatatga ggttttgttt tgtagtttat tttggaatct agtattttga taatttaaga   3360

atcagaagca ctggcctttc tacattttat aacattattt tgtatataat gtgtatttat   3420

aatatgaaac agatgtgtac aggaatttat t                                  3451
```

<210> SEQ ID NO 10
<211> LENGTH: 686
<212> TYPE: PRT
<213> ORGANISM: Mus musculus

<400> SEQUENCE: 10

```
Met Thr Pro Ala Ser Arg Ser Ala Cys Arg Trp Ala Leu Leu Leu Leu
 1               5                  10                  15

Ala Val Leu Trp Pro Gln Gln Arg Ala Ala Gly Ser Gly Ile Phe Gln
            20                  25                  30

Leu Arg Leu Gln Glu Phe Val Asn Gln Arg Gly Met Leu Ala Asn Gly
        35                  40                  45

Gln Ser Cys Glu Pro Gly Cys Arg Thr Phe Phe Arg Ile Cys Leu Lys
    50                  55                  60

His Phe Gln Ala Thr Phe Ser Glu Gly Pro Cys Thr Phe Gly Asn Val
65                  70                  75                  80

Ser Thr Pro Val Leu Gly Thr Asn Ser Phe Val Val Arg Asp Lys Asn
                85                  90                  95

Ser Gly Ser Gly Arg Asn Pro Leu Gln Leu Pro Phe Asn Phe Thr Trp
            100                 105                 110

Pro Gly Thr Phe Ser Leu Asn Ile Gln Ala Trp His Thr Pro Gly Asp
        115                 120                 125

Asp Leu Arg Pro Glu Thr Ser Pro Gly Asn Ser Leu Ile Ser Gln Ile
    130                 135                 140

Ile Ile Gln Gly Ser Leu Ala Val Gly Lys Ile Trp Arg Thr Asp Glu
145                 150                 155                 160

Gln Asn Asp Thr Leu Thr Arg Leu Ser Tyr Ser Tyr Arg Val Ile Cys
                165                 170                 175

Ser Asp Asn Tyr Tyr Gly Glu Ser Cys Ser Arg Leu Cys Lys Lys Arg
            180                 185                 190

Asp Asp His Phe Gly His Tyr Glu Cys Gln Pro Asp Gly Ser Leu Ser
        195                 200                 205

Cys Leu Pro Gly Trp Thr Gly Lys Tyr Cys Asp Gln Pro Ile Cys Leu
    210                 215                 220

Ser Gly Cys His Glu Gln Asn Gly Tyr Cys Ser Lys Pro Asp Glu Cys
225                 230                 235                 240
```

```
Ile Cys Arg Pro Gly Trp Gln Gly Arg Leu Cys Asn Glu Cys Ile Pro
                245                 250                 255

His Asn Gly Cys Arg His Gly Thr Cys Ser Ile Pro Trp Gln Cys Ala
            260                 265                 270

Cys Asp Glu Gly Trp Gly Gly Leu Phe Cys Asp Gln Asp Leu Asn Tyr
        275                 280                 285

Cys Thr His His Ser Pro Cys Lys Asn Gly Ser Thr Cys Ser Asn Ser
    290                 295                 300

Gly Pro Lys Gly Tyr Thr Cys Thr Cys Leu Pro Gly Tyr Thr Gly Glu
305                 310                 315                 320

His Cys Glu Leu Gly Leu Ser Lys Cys Ala Ser Asn Pro Cys Arg Asn
                325                 330                 335

Gly Gly Ser Cys Lys Asp Gln Glu Asn Ser Tyr His Cys Leu Cys Pro
            340                 345                 350

Pro Gly Tyr Tyr Gly Gln His Cys Glu His Ser Thr Leu Thr Cys Ala
        355                 360                 365

Asp Ser Pro Cys Phe Asn Gly Gly Ser Cys Arg Glu Arg Asn Gln Gly
    370                 375                 380

Ser Ser Tyr Ala Cys Glu Cys Pro Pro Asn Phe Thr Gly Ser Asn Cys
385                 390                 395                 400

Glu Lys Lys Val Asp Arg Cys Thr Ser Asn Pro Cys Ala Asn Gly Gly
                405                 410                 415

Gln Cys Gln Asn Arg Gly Pro Ser Arg Thr Cys Arg Cys Arg Pro Gly
            420                 425                 430

Phe Thr Gly Thr His Cys Glu Leu His Ile Ser Asp Cys Ala Arg Ser
        435                 440                 445

Pro Cys Ala His Gly Gly Thr Cys His Asp Leu Glu Asn Gly Pro Val
    450                 455                 460

Cys Thr Cys Pro Ala Gly Phe Ser Gly Arg Arg Cys Glu Val Arg Ile
465                 470                 475                 480

Thr His Asp Ala Cys Ala Ser Gly Pro Cys Phe Asn Gly Ala Thr Cys
                485                 490                 495

Tyr Thr Gly Leu Ser Pro Asn Asn Phe Val Cys Asn Cys Pro Tyr Gly
            500                 505                 510

Phe Val Gly Ser Arg Cys Glu Phe Pro Val Gly Leu Pro Pro Ser Phe
        515                 520                 525

Pro Trp Val Ala Val Ser Leu Gly Val Gly Leu Val Val Leu Leu Val
    530                 535                 540

Leu Leu Val Met Val Val Val Ala Val Arg Gln Leu Arg Leu Arg Arg
545                 550                 555                 560

Pro Asp Asp Glu Ser Arg Glu Ala Met Asn Asn Leu Ser Asp Phe Gln
                565                 570                 575

Lys Asp Asn Leu Ile Pro Ala Ala Gln Leu Lys Asn Thr Asn Gln Lys
            580                 585                 590

Lys Glu Leu Glu Val Asp Cys Gly Leu Asp Lys Ser Asn Cys Gly Lys
        595                 600                 605

Leu Gln Asn His Thr Leu Asp Tyr Asn Leu Ala Pro Gly Leu Leu Gly
    610                 615                 620

Arg Gly Gly Met Pro Gly Lys Tyr Pro His Ser Asp Lys Ser Leu Gly
625                 630                 635                 640

Glu Lys Val Pro Leu Arg Leu His Ser Glu Lys Pro Glu Cys Arg Ile
                645                 650                 655
```

```
Ser Ala Ile Cys Ser Pro Arg Asp Ser Met Tyr Gln Ser Val Cys Leu
            660                 665                 670

Ile Ser Glu Glu Arg Asn Glu Cys Val Ile Ala Thr Glu Val
        675                 680                 685


<210> SEQ ID NO 11
<211> LENGTH: 2977
<212> TYPE: DNA
<213> ORGANISM: Homo sapiens

<400> SEQUENCE: 11

agctggggta aggagttcaa ggcagcgccc acacccgggg gctctccgca acccgaccgc      60

ctgtccgctc ccccacttcc cgccctccct cccacctact cattcaccca cccacccacc     120

cagagccggg acggcagccc aggcgcccgg gccccgccgt ctcctcgccg cgatcctgga     180

cttcctcttg ctgcaggacc cggcttccac gtgtgtcccg gagccggcgt ctcagcacac     240

gctccgctcc gggcctgggt gcctacagca gccagagcag cagggagtcc gggacccggg     300

cggcatctgg gccaagttag gcgccgccga ggccagcgct gaacgtctcc agggccggag     360

gagccgcggg gcgtccgggt ctgagccgca gcaaatgggc tccgacgtgc gggacctgaa     420

cgcgctgctg cccgccgtcc cctccctggg tggcggcggc ggctgtgccc tgcctgtgag     480

cggcgcggcg cagtgggcgc cggtgctgga ctttgcgccc ccgggcgctt cggcttacgg     540

gtcgttgggc ggcccccgcgc cgccaccggc tccgccgcca cccccgccgc cgccgcctca     600

ctccttcatc aaacaggagc cgagctgggg cggcgcggag ccgcacgagg agcagtgcct     660

gagcgccttc actgtccact ttttccggcca gttcactggc acagccggag cctgtcgcta     720

cgggcccttc ggtcctcctc cgcccagcca ggcgtcatcc ggccaggcca ggatgtttcc     780

taacgcgccc tacctgccca gctgcctcga gagccagccc gctattcgca atcagggtta     840

cagcacggtc accttcgacg ggacgcccag ctacggtcac acgccctcgc accatgcggc     900

gcagttcccc aaccactcat tcaagcatga ggatcccatg ggccagcagg gctcgctggg     960

tgagcagcag tactcggtgc cgcccccggt ctatggctgc cacaccccca ccgacagctg    1020

caccggcagc caggctttgc tgctgaggac gccctacagc agtgacaatt tataccaaat    1080

gacatcccag cttgaatgca tgacctggaa tcagatgaac ttaggagcca ccttaaaggg    1140

ccacagcaca gggtacgaga gcgataacca cacaacgccc atcctctgcg gagcccaata    1200

cagaatacac acgcacggtg tcttcagagg cattcaggat gtgcgacgtg tgcctggagt    1260

agccccgact cttgtacggt cggcatctga gaccagtgag aaacgcccct tcatgtgtgc    1320

ttacccaggc tgcaataaga gatattttaa gctgtcccac ttacagatgc acagcaggaa    1380

gcacactggt gagaaaccat accagtgtga cttcaaggac tgtgaacgaa ggttttctcg    1440

ttcagaccag ctcaaaagac accaaaggag acatacaggt gtgaaaccat tccagtgtaa    1500

aacttgtcag cgaaagttct cccggtccga ccacctgaag acccacacca ggactcatac    1560

aggtgaaaag cccttcagct gtcggtggcc aagttgtcag aaaaagtttg cccggtcaga    1620

tgaattagtc cgccatcaca acatgcatca gagaaacatg accaaactcc agctggcgct    1680

ttgaggggtc tccctcgggg accgttcagt gtcccaggca gcacagtgtg tgaactgctt    1740

tcaagtctga ctctccactc ctcctcacta aaaaggaaac ttcagttgat cttcttcatc    1800

caacttccaa gacaagatac cggtgcttct ggaaactacc aggtgtgcct ggaagagttg    1860

gtctctgccc tgcctacttt tagttgactc acaggccctg gagaagcagc taacaatgtc    1920

tggttagtta aaagcccatt gccatttggt gtggattttc tactgtaaga agagccatag    1980
```

```
ctgatcatgt ccccctgacc cttcccttct ttttttatgc tcgttttcgc tggggatgga   2040

attattgtac cattttctat catggaatat ttataggcca gggcatgtgt atgtgtctgc   2100

taatgtaaac tttgtcatgg tttccattta ctaacagcaa cagcaagaaa taaatcagag   2160

agcaaggcat cgggggtgaa tcttgtctaa cattcccgag gtcagccagg ctgctaacct   2220

ggaaagcagg atgtagttct gccaggcaac ttttaaagct catgcatttc aagcagctga   2280

agaaaaaatc agaactaacc agtacctctg tatagaaatc taaaagaatt ttaccattca   2340

gttaattcaa tgtgaacact ggcacactgc tcttaagaaa ctatgaagat ctgagatttt   2400

tttgtgtatg tttttgactc ttttgagtgg taatcatatg tgtctttata gatgtacata   2460

cctccttgca caaatggagg ggaattcatt ttcatcactg ggagtgtcct tagtgtataa   2520

aaaccatgct ggtatatggc ttcaagttgt aaaaatgaaa gtgactttaa aagaaaatag   2580

gggatggtcc aggatctcca ctgataagac tgtttttaag taacttaagg acctttgggt   2640

ctacaagtat atgtgaaaaa aatgagactt actgggtgag gaaatccatt gtttaaagat   2700

ggtcgtgtgt gtgtgtgtgt gtgtgtgtgt gtgtgtgttg tgttgtgttt tgtttttttaa   2760

gggagggaat ttattattta ccgttgcttg aaattactgt gtaaatatat gtctgataat   2820

gatttgctct ttgacaacta aaattaggac tgtataagta ctagatgcat cactgggtgt   2880

tgatcttaca agatattgat gataacactt aaaattgtaa cctgcatttt tcactttgct   2940

ctcaattaaa gtctattcaa aaggaaaaaa aaaaaaa                            2977


<210> SEQ ID NO 12
<211> LENGTH: 497
<212> TYPE: PRT
<213> ORGANISM: Homo sapiens

<400> SEQUENCE: 12

Met Gln Asp Pro Ala Ser Thr Cys Val Pro Glu Pro Ala Ser Gln His
 1               5                  10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Pro Ser Gln Ala Ser Ser Gly Gln
            180                 185                 190
```

```
Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly His Ser Thr
305                 310                 315                 320

Gly Tyr Glu Ser Asp Asn His Thr Thr Pro Ile Leu Cys Gly Ala Gln
                325                 330                 335

Tyr Arg Ile His Thr His Gly Val Phe Arg Gly Ile Gln Asp Val Arg
            340                 345                 350

Arg Val Pro Gly Val Ala Pro Thr Leu Val Arg Ser Ala Ser Glu Thr
        355                 360                 365

Ser Glu Lys Arg Pro Phe Met Cys Ala Tyr Pro Gly Cys Asn Lys Arg
    370                 375                 380

Tyr Phe Lys Leu Ser His Leu Gln Met His Ser Arg Lys His Thr Gly
385                 390                 395                 400

Glu Lys Pro Tyr Gln Cys Asp Phe Lys Asp Cys Glu Arg Arg Phe Ser
                405                 410                 415

Arg Ser Asp Gln Leu Lys Arg His Gln Arg Arg His Thr Gly Val Lys
            420                 425                 430

Pro Phe Gln Cys Lys Thr Cys Gln Arg Lys Phe Ser Arg Ser Asp His
        435                 440                 445

Leu Lys Thr His Thr Arg Thr His Thr Gly Glu Lys Pro Phe Ser Cys
    450                 455                 460

Arg Trp Pro Ser Cys Gln Lys Lys Phe Ala Arg Ser Asp Glu Leu Val
465                 470                 475                 480

Arg His His Asn Met His Gln Arg Asn Met Thr Lys Leu Gln Leu Ala
                485                 490                 495

Leu
```

<210> SEQ ID NO 13
<211> LENGTH: 3028
<212> TYPE: DNA
<213> ORGANISM: Homo sapiens

<400> SEQUENCE: 13

```
agctggggta aggagttcaa ggcagcgccc acacccgggg gctctccgca acccgaccgc      60

ctgtccgctc ccccacttcc cgccctccct cccacctact cattcaccca cccacccacc     120

cagagccggg acggcagccc aggcgcccgg gccccgccgt ctcctcgccg cgatcctgga     180

cttcctcttg ctgcaggacc cggcttccac gtgtgtcccg gagccggcgt ctcagcacac     240

gctccgctcc gggcctgggt gcctacagca gccagagcag cagggagtcc gggacccggg     300

cggcatctgg gccaagttag gcgccgccga ggccagcgct gaacgtctcc agggccggag     360
```

```
gagccgcggg gcgtccgggt ctgagccgca gcaaatgggc tccgacgtgc gggacctgaa    420
cgcgctgctg cccgccgtcc cctccctggg tggcggcggc ggctgtgccc tgcctgtgag    480
cggcgcggcg cagtgggcgc cggtgctgga ctttgcgccc ccgggcgctt cggcttacgg    540
gtcgttgggc ggccccgcgc cgccaccggc tccgccgcca cccccgccgc cgccgcctca    600
ctccttcatc aaacaggagc cgagctgggg cggcgcggag ccgcacgagg agcagtgcct    660
gagcgccttc actgtccact ttttccggcca gttcactggc acagccggag cctgtcgcta    720
cgggcccttc ggtcctcctc cgcccagcca ggcgtcatcc ggccaggcca ggatgtttcc    780
taacgcgccc tacctgccca gctgcctcga gagccagccc gctattcgca atcagggtta    840
cagcacggtc accttcgacg ggacgcccag ctacggtcac acgccctcgc accatgcggc    900
gcagttcccc aaccactcat tcaagcatga ggatcccatg ggccagcagg gctcgctggg    960
tgagcagcag tactcggtgc cgcccccggt ctatggctgc cacaccccca ccgacagctg   1020
caccggcagc caggctttgc tgctgaggac gccctacagc agtgacaatt tataccaaat   1080
gacatcccag cttgaatgca tgacctggaa tcagatgaac ttaggagcca ccttaaaggg   1140
agttgctgct gggagctcca gctcagtgaa atggacagaa gggcagagca accacagcac   1200
agggtacgag agcgataacc acacaacgcc catcctctgc ggagcccaat acagaataca   1260
cacgcacggt gtcttcagag gcattcagga tgtgcgacgt gtgcctggag tagccccgac   1320
tcttgtacgg tcggcatctg agaccagtga gaaacgcccc ttcatgtgtg cttacccagg   1380
ctgcaataag agatatttta agctgtccca cttacagatg cacagcagga agcacactgg   1440
tgagaaacca taccagtgtg acttcaagga ctgtgaacga aggttttctc gttcagacca   1500
gctcaaaaga caccaaagga gacatacagg tgtgaaacca ttccagtgta aaacttgtca   1560
gcgaaagttc tcccggtccg accacctgaa gacccacacc aggactcata caggtgaaaa   1620
gcccttcagc tgtcggtggc caagttgtca gaaaaagttt gcccggtcag atgaattagt   1680
ccgccatcac aacatgcatc agagaaacat gaccaaactc cagctggcgc tttgaggggt   1740
ctccctcggg gaccgttcag tgtcccaggc agcacagtgt gtgaactgct ttcaagtctg   1800
actctccact cctcctcact aaaaaggaaa cttcagttga tcttcttcat ccaacttcca   1860
agacaagata ccggtgcttc tggaaactac caggtgtgcc tggaagagtt ggtctctgcc   1920
ctgcctactt ttagttgact cacaggccct ggagaagcag ctaacaatgt ctggttagtt   1980
aaaagcccat tgccatttgg tgtggatttt ctactgtaag aagagccata gctgatcatg   2040
tcccccctgac ccttcccttc ttttttttatg ctcgttttcg ctggggatgg aattattgta   2100
ccattttcta tcatggaata tttataggcc agggcatgtg tatgtgtctg ctaatgtaaa   2160
ctttgtcatg gtttccattt actaacagca acagcaagaa ataaatcaga gagcaaggca   2220
tcgggggtga atcttgtcta acattcccga ggtcagccag gctgctaacc tggaaagcag   2280
gatgtagttc tgccaggcaa cttttaaagc tcatgcattt caagcagctg aagaaaaaat   2340
cagaactaac cagtacctct gtatagaaat ctaaaagaat tttaccattc agttaattca   2400
atgtgaacac tggcacactg ctcttaagaa actatgaaga tctgagattt ttttgtgtat   2460
gtttttgact cttttgagtg gtaatcatat gtgtctttat agatgtacat acctccttgc   2520
acaaatggag gggaattcat tttcatcact gggagtgtcc ttagtgtata aaaaccatgc   2580
tggtatatgg cttcaagttg taaaaatgaa agtgacttta aaagaaaata ggggatggtc   2640
caggatctcc actgataaga ctgtttttaa gtaacttaag gacctttggg tctacaagta   2700
tatgtgaaaa aaatgagact tactgggtga ggaaatccat tgtttaaaga tggtcgtgtg   2760
```

```
tgtgtgtgtg tgtgtgtgtg tgtgtgtgtt gtgttgtgtt ttgtttttta agggagggaa   2820

tttattattt accgttgctt gaaattactg tgtaaatata tgtctgataa tgatttgctc   2880

tttgacaact aaaattagga ctgtataagt actagatgca tcactgggtg ttgatcttac   2940

aagatattga tgataacact taaaattgta acctgcattt ttcactttgc tctcaattaa   3000

agtctattca aaaggaaaaa aaaaaaaa                                      3028


<210> SEQ ID NO 14
<211> LENGTH: 514
<212> TYPE: PRT
<213> ORGANISM: Homo sapiens

<400> SEQUENCE: 14

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly Val Ala Ala
305                 310                 315                 320
```

```
Gly Ser Ser Ser Ser Val Lys Trp Thr Glu Gly Gln Ser Asn His Ser
                325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
        355                 360                 365

Arg Arg Val Pro Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
            420                 425                 430

Ser Arg Ser Asp Gln Leu Lys Arg His Gln Arg Arg His Thr Gly Val
        435                 440                 445

Lys Pro Phe Gln Cys Lys Thr Cys Gln Arg Lys Phe Ser Arg Ser Asp
    450                 455                 460

His Leu Lys Thr His Thr Arg Thr His Thr Gly Glu Lys Pro Phe Ser
465                 470                 475                 480

Cys Arg Trp Pro Ser Cys Gln Lys Lys Phe Ala Arg Ser Asp Glu Leu
                485                 490                 495

Val Arg His His Asn Met His Gln Arg Asn Met Thr Lys Leu Gln Leu
            500                 505                 510

Ala Leu
```

<210> SEQ ID NO 15
<211> LENGTH: 3037
<212> TYPE: DNA
<213> ORGANISM: Homo sapiens

<400> SEQUENCE: 15

```
agctggggta aggagttcaa ggcagcgccc acacccgggg gctctccgca acccgaccgc      60

ctgtccgctc ccccacttcc cgccctccct cccacctact cattcaccca cccacccacc     120

cagagccggg acggcagccc aggcgcccgg gccccgccgt ctcctcgccg cgatcctgga     180

cttcctcttg ctgcaggacc cggcttccac gtgtgtcccg gagccggcgt ctcagcacac     240

gctccgctcc gggcctgggt gcctacagca gccagagcag cagggagtcc gggacccggg     300

cggcatctgg gccaagttag gcgccgccga ggccagcgct gaacgtctcc agggccggag     360

gagccgcggg gcgtccgggt ctgagccgca gcaaatgggc tccgacgtgc gggacctgaa     420

cgcgctgctg cccgccgtcc cctccctggg tggcggcggc ggctgtgccc tgcctgtgag     480

cggcgcggcg cagtgggcgc cggtgctgga ctttgcgccc ccgggcgctt cggcttacgg     540

gtcgttgggc ggccccgcgc cgccaccggc tccgccgcca cccccgccgc cgccgcctca     600

ctccttcatc aaacaggagc cgagctgggg cggcgcggag ccgcacgagg agcagtgcct     660

gagcgccttc actgtccact ttccggccca gttcactggc acagccggag cctgtcgcta     720

cgggcccttc ggtcctcctc cgcccagcca ggcgtcatcc ggccaggcca ggatgtttcc     780

taacgcgccc tacctgccca gctgcctcga gagccagccc gctattcgca atcagggtta     840

cagcacggtc accttcgacg ggacgcccag ctacggtcac acgccctcgc accatgcggc     900

gcagttcccc aaccactcat tcaagcatga ggatcccatg ggccagcagg gctcgctggg     960

tgagcagcag tactcggtgc cgcccccggt ctatggctgc cacacccccca ccgacagctg    1020
```

```
caccggcagc caggctttgc tgctgaggac gccctacagc agtgacaatt tataccaaat   1080
gacatcccag cttgaatgca tgacctggaa tcagatgaac ttaggagcca ccttaaaggg   1140
agttgctgct gggagctcca gctcagtgaa atggacagaa gggcagagca accacagcac   1200
agggtacgag agcgataacc acacaacgcc catcctctgc ggagcccaat acagaataca   1260
cacgcacggt gtcttcagag gcattcagga tgtgcgacgt gtgcctggag tagccccgac   1320
tcttgtacgg tcggcatctg agaccagtga gaaacgcccc ttcatgtgtg cttacccagg   1380
ctgcaataag agatatttta agctgtccca cttacagatg cacagcagga agcacactgg   1440
tgagaaacca taccagtgtg acttcaagga ctgtgaacga aggttttctc gttcagacca   1500
gctcaaaaga caccaaagga gacatacagg tgtgaaacca ttccagtgta aaacttgtca   1560
gcgaaagttc tcccggtccg accacctgaa gacccacacc aggactcata caggtaaaac   1620
aagtgaaaag cccttcagct gtcggtggcc aagttgtcag aaaaagtttg cccggtcaga   1680
tgaattagtc cgccatcaca acatgcatca gagaaacatg accaaactcc agctggcgct   1740
ttgaggggtc tccctcgggg accgttcagt gtcccaggca gcacagtgtg tgaactgctt   1800
tcaagtctga ctctccactc ctcctcacta aaaaggaaac ttcagttgat cttcttcatc   1860
caacttccaa gacaagatac cggtgcttct ggaaactacc aggtgtgcct ggaagagttg   1920
gtctctgccc tgcctacttt tagttgactc acaggccctg gagaagcagc taacaatgtc   1980
tggttagtta aaagcccatt gccatttggt gtggattttc tactgtaaga agagccatag   2040
ctgatcatgt ccccctgacc cttcccttct ttttttatgc tcgttttcgc tggggatgga   2100
attattgtac cattttctat catggaatat ttataggcca gggcatgtgt atgtgtctgc   2160
taatgtaaac tttgtcatgg tttccattta ctaacagcaa cagcaagaaa taaatcagag   2220
agcaaggcat cgggggtgaa tcttgtctaa cattcccgag gtcagccagg ctgctaacct   2280
ggaaagcagg atgtagttct gccaggcaac ttttaaagct catgcatttc aagcagctga   2340
agaaaaaatc agaactaacc agtacctctg tatagaaatc taaaagaatt ttaccattca   2400
gttaattcaa tgtgaacact ggcacactgc tcttaagaaa ctatgaagat ctgagatttt   2460
tttgtgtatg tttttgactc ttttgagtgg taatcatatg tgtctttata gatgtacata   2520
cctccttgca caaatggagg ggaattcatt ttcatcactg ggagtgtcct tagtgtataa   2580
aaaccatgct ggtatatggc ttcaagttgt aaaaatgaaa gtgactttaa aagaaaatag   2640
gggatggtcc aggatctcca ctgataagac tgtttttaag taacttaagg acctttgggt   2700
ctacaagtat atgtgaaaaa aatgagactt actgggtgag gaaatccatt gtttaaagat   2760
ggtcgtgtgt gtgtgtgtgt gtgtgtgtgt gtgtgtgttg tgttgtgttt tgttttttaa   2820
gggagggaat ttattattta ccgttgcttg aaattactgt gtaaatatat gtctgataat   2880
gatttgctct ttgacaacta aaattaggac tgtataagta ctagatgcat cactgggtgt   2940
tgatcttaca agatattgat gataacactt aaaattgtaa cctgcatttt tcactttgct   3000
ctcaattaaa gtctattcaa aaggaaaaaa aaaaaaa                            3037
```

<210> SEQ ID NO 16
<211> LENGTH: 517
<212> TYPE: PRT
<213> ORGANISM: Homo sapiens

<400> SEQUENCE: 16

```
Met Gln Asp Pro Ala Ser Thr Cys Val Pro Glu Pro Ala Ser Gln His
 1               5                  10                  15
```

```
Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly Val Ala Ala
305                 310                 315                 320

Gly Ser Ser Ser Ser Val Lys Trp Thr Glu Gly Gln Ser Asn His Ser
                325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
        355                 360                 365

Arg Arg Val Pro Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
            420                 425                 430
```

```
Ser Arg Ser Asp Gln Leu Lys Arg His Gln Arg Arg His Thr Gly Val
        435                 440                 445

Lys Pro Phe Gln Cys Lys Thr Cys Gln Arg Lys Phe Ser Arg Ser Asp
    450                 455                 460

His Leu Lys Thr His Thr Arg Thr His Thr Gly Lys Thr Ser Glu Lys
465                 470                 475                 480

Pro Phe Ser Cys Arg Trp Pro Ser Cys Gln Lys Lys Phe Ala Arg Ser
                485                 490                 495

Asp Glu Leu Val Arg His His Asn Met His Gln Arg Asn Met Thr Lys
            500                 505                 510

Leu Gln Leu Ala Leu
        515


<210> SEQ ID NO 17
<211> LENGTH: 2438
<212> TYPE: DNA
<213> ORGANISM: Homo sapiens

<400> SEQUENCE: 17

aggcgctttc accactgccc ctcccggggg gacctgaagg agagggtttg aggccggtct     60

ttgcccgccg aggtctgcgt gtccggtctg ggaggaggcc taggagggct cgcgggccac    120

gggcatcctt gggcccgagt tctggggtgc ggacggacgt ctcgagagtg ggtgccgcga    180

ctcgggaccc acggccctcg ccgggcacgg acagttgcgg agcagggctc tgaggattgt    240

gcagtgccct gggtccctgc ctactcctgg gctcaggaat ggagaagggt tacagcacgg    300

tcaccttcga cgggacgccc agctacggtc acacgccctc gcaccatgcg gcgcagttcc    360

ccaaccactc attcaagcat gaggatccca tgggccagca gggctcgctg ggtgagcagc    420

agtactcggt gccgcccccg gtctatggct gccacacccc caccgacagc tgcaccggca    480

gccaggcttt gctgctgagg acgccctaca gcagtgacaa tttataccaa atgacatccc    540

agcttgaatg catgacctgg aatcagatga acttaggagc caccttaaag ggccacagca    600

cagggtacga gagcgataac cacacaacgc ccatcctctg cggagcccaa tacagaatac    660

acacgcacgg tgtcttcaga ggcattcagg atgtgcgacg tgtgcctgga gtagccccga    720

ctcttgtacg gtcggcatct gagaccagtg agaaacgccc cttcatgtgt gcttacccag    780

gctgcaataa gagatatttt aagctgtccc acttacagat gcacagcagg aagcacactg    840

gtgagaaacc ataccagtgt gacttcaagg actgtgaacg aaggttttct cgttcagacc    900

agctcaaaag acaccaaagg agacatacag gtgtgaaacc attccagtgt aaaacttgtc    960

agcgaaagtt ctcccggtcc gaccacctga agacccacac caggactcat acaggtaaaa   1020

caagtgaaaa gcccttcagc tgtcggtggc caagttgtca gaaaaagttt gcccggtcag   1080

atgaattagt ccgccatcac aacatgcatc agagaaacat gaccaaactc cagctggcgc   1140

tttgaggggt ctccctcggg gaccgttcag tgtcccaggc agcacagtgt gtgaactgct   1200

ttcaagtctg actctccact cctcctcact aaaaaggaaa cttcagttga tcttcttcat   1260

ccaacttcca agacaagata ccggtgcttc tggaaactac caggtgtgcc tggaagagtt   1320

ggtctctgcc ctgcctactt ttagttgact cacaggccct ggagaagcag ctaacaatgt   1380

ctggttagtt aaaagcccat tgccatttgg tgtggatttt ctactgtaag aagagccata   1440

gctgatcatg tccccctgac ccttcccttc ttttttttatg ctcgttttcg ctggggatgg   1500

aattattgta ccattttcta tcatggaata tttataggcc agggcatgtg tatgtgtctg   1560

ctaatgtaaa ctttgtcatg gtttccattt actaacagca acagcaagaa ataaatcaga   1620
```

```
gagcaaggca tcgggggtga atcttgtcta acattcccga ggtcagccag gctgctaacc   1680

tggaaagcag gatgtagttc tgccaggcaa cttttaaagc tcatgcattt caagcagctg   1740

aagaaaaaat cagaactaac cagtacctct gtatagaaat ctaaaagaat tttaccattc   1800

agttaattca atgtgaacac tggcacactg ctcttaagaa actatgaaga tctgagattt   1860

ttttgtgtat gtttttgact cttttgagtg gtaatcatat gtgtctttat agatgtacat   1920

acctccttgc acaaatggag gggaattcat tttcatcact gggagtgtcc ttagtgtata   1980

aaaaccatgc tggtatatgg cttcaagttg taaaaatgaa agtgacttta aaagaaaata   2040

ggggatggtc caggatctcc actgataaga ctgtttttaa gtaacttaag gacctttggg   2100

tctacaagta tatgtgaaaa aaatgagact tactgggtga ggaaatccat tgtttaaaga   2160

tggtcgtgtg tgtgtgtgtg tgtgtgtgtg tgtgtgtgtt gtgttgtgtt ttgtttttta   2220

agggagggaa tttattattt accgttgctt gaaattactg tgtaaatata tgtctgataa   2280

tgatttgctc tttgacaact aaaattagga ctgtataagt actagatgca tcactgggtg   2340

ttgatcttac aagatattga tgataacact taaaattgta acctgcattt ttcactttgc   2400

tctcaattaa agtctattca aaaggaaaaa aaaaaaaa                           2438
```

```
<210> SEQ ID NO 18
<211> LENGTH: 288
<212> TYPE: PRT
<213> ORGANISM: Homo sapiens

<400> SEQUENCE: 18

Met Glu Lys Gly Tyr Ser Thr Val Thr Phe Asp Gly Thr Pro Ser Tyr
1               5                   10                  15

Gly His Thr Pro Ser His His Ala Ala Gln Phe Pro Asn His Ser Phe
            20                  25                  30

Lys His Glu Asp Pro Met Gly Gln Gln Gly Ser Leu Gly Glu Gln Gln
        35                  40                  45

Tyr Ser Val Pro Pro Pro Val Tyr Gly Cys His Thr Pro Thr Asp Ser
    50                  55                  60

Cys Thr Gly Ser Gln Ala Leu Leu Leu Arg Thr Pro Tyr Ser Ser Asp
65                  70                  75                  80

Asn Leu Tyr Gln Met Thr Ser Gln Leu Glu Cys Met Thr Trp Asn Gln
                85                  90                  95

Met Asn Leu Gly Ala Thr Leu Lys Gly His Ser Thr Gly Tyr Glu Ser
            100                 105                 110

Asp Asn His Thr Thr Pro Ile Leu Cys Gly Ala Gln Tyr Arg Ile His
        115                 120                 125

Thr His Gly Val Phe Arg Gly Ile Gln Asp Val Arg Arg Val Pro Gly
    130                 135                 140

Val Ala Pro Thr Leu Val Arg Ser Ala Ser Glu Thr Ser Glu Lys Arg
145                 150                 155                 160

Pro Phe Met Cys Ala Tyr Pro Gly Cys Asn Lys Arg Tyr Phe Lys Leu
                165                 170                 175

Ser His Leu Gln Met His Ser Arg Lys His Thr Gly Glu Lys Pro Tyr
            180                 185                 190

Gln Cys Asp Phe Lys Asp Cys Glu Arg Arg Phe Ser Arg Ser Asp Gln
        195                 200                 205

Leu Lys Arg His Gln Arg Arg His Thr Gly Val Lys Pro Phe Gln Cys
    210                 215                 220
```

-continued

```
Lys Thr Cys Gln Arg Lys Phe Ser Arg Ser Asp His Leu Lys Thr His
225                 230                 235                 240

Thr Arg Thr His Thr Gly Lys Thr Ser Glu Lys Pro Phe Ser Cys Arg
                245                 250                 255

Trp Pro Ser Cys Gln Lys Lys Phe Ala Arg Ser Asp Glu Leu Val Arg
            260                 265                 270

His His Asn Met His Gln Arg Asn Met Thr Lys Leu Gln Leu Ala Leu
        275                 280                 285


<210> SEQ ID NO 19
<211> LENGTH: 2480
<212> TYPE: DNA
<213> ORGANISM: Homo sapiens

<400> SEQUENCE: 19

aggcgctttc accactgccc ctcccggggg gacctgaagg agagggtttg aggccggtct      60

ttgcccgccg aggtctgcgt gtccggtctg ggaggaggcc taggagggct cgcgggccac     120

gggcatcctt gggcccgagt tctggggtgc ggacggacgt ctcgagagtg ggtgccgcga     180

ctcgggaccc acggccctcg ccgggcacgg acagttgcgg agcagggctc tgaggattgt     240

gcagtgccct gggtccctgc ctactcctgg gctcaggaat ggagaagggt tacagcacgg     300

tcaccttcga cgggacgccc agctacggtc acacgccctc gcaccatgcg gcgcagttcc     360

ccaaccactc attcaagcat gaggatccca tgggccagca gggctcgctg ggtgagcagc     420

agtactcggt gccgcccccg gtctatggct gccacacccc caccgacagc tgcaccggca     480

gccaggcttt gctgctgagg acgccctaca gcagtgacaa tttataccaa atgacatccc     540

agcttgaatg catgacctgg aatcagatga acttaggagc caccttaaag ggagttgctg     600

ctgggagctc cagctcagtg aaatggacag aagggcagag caaccacagc acagggtacg     660

agagcgataa ccacacaacg cccatcctct gcggagccca atacagaata cacacgcacg     720

gtgtcttcag aggcattcag gatgtgcgac gtgtgcctgg agtagccccg actcttgtac     780

ggtcggcatc tgagaccagt gagaaacgcc ccttcatgtg tgcttaccca ggctgcaata     840

agagatattt taagctgtcc cacttacaga tgcacagcag gaagcacact ggtgagaaac     900

cataccagtg tgacttcaag gactgtgaac gaaggttttc tcgttcagac cagctcaaaa     960

gacaccaaag gagacataca ggtgtgaaac cattccagtg taaaacttgt cagcgaaagt    1020

tctcccggtc cgaccacctg aagacccaca ccaggactca tacaggtgaa aagcccttca    1080

gctgtcggtg gccaagttgt cagaaaaagt ttgcccggtc agatgaatta gtccgccatc    1140

acaacatgca tcagagaaac atgaccaaac tccagctggc gctttgaggg gtctccctcg    1200

gggaccgttc agtgtcccag gcagcacagt gtgtgaactg ctttcaagtc tgactctcca    1260

ctcctcctca ctaaaaagga aacttcagtt gatcttcttc atccaacttc caagacaaga    1320

taccggtgct tctggaaact accaggtgtg cctggaagag ttggtctctg ccctgcctac    1380

ttttagttga ctcacaggcc ctggagaagc agctaacaat gtctggttag ttaaaagccc    1440

attgccattt ggtgtggatt ttctactgta agaagagcca tagctgatca tgtccccctg    1500

acccttccct tcttttttta tgctcgtttt cgctggggat ggaattattg taccattttc    1560

tatcatggaa tatttatagg ccagggcatg tgtatgtgtc tgctaatgta aactttgtca    1620

tggtttccat ttactaacag caacagcaag aaataaatca gagagcaagg catcgggggt    1680

gaatcttgtc taacattccc gaggtcagcc aggctgctaa cctggaaagc aggatgtagt    1740

tctgccaggc aacttttaaa gctcatgcat ttcaagcagc tgaagaaaaa atcagaacta    1800
```

```
accagtacct ctgtatagaa atctaaaaga attttaccat tcagttaatt caatgtgaac   1860

actggcacac tgctcttaag aaactatgaa gatctgagat ttttttgtgt atgtttttga   1920

ctcttttgag tggtaatcat atgtgtcttt atagatgtac atacctcctt gcacaaatgg   1980

aggggaattc attttcatca ctgggagtgt ccttagtgta taaaaaccat gctggtatat   2040

ggcttcaagt tgtaaaaatg aaagtgactt taaaagaaaa taggggatgg tccaggatct   2100

ccactgataa gactgttttt aagtaactta aggacctttg ggtctacaag tatatgtgaa   2160

aaaaatgaga cttactgggt gaggaaatcc attgtttaaa gatggtcgtg tgtgtgtgtg   2220

tgtgtgtgtg tgtgtgtgtg ttgtgttgtg ttttgttttt taagggaggg aatttattat   2280

ttaccgttgc ttgaaattac tgtgtaaata tatgtctgat aatgatttgc tctttgacaa   2340

ctaaaattag gactgtataa gtactagatg catcactggg tgttgatctt acaagatatt   2400

gatgataaca cttaaaattg taacctgcat tttcacttt gctctcaatt aaagtctatt    2460

caaaaggaaa aaaaaaaaaa                                               2480


<210> SEQ ID NO 20
<211> LENGTH: 302
<212> TYPE: PRT
<213> ORGANISM: Homo sapiens

<400> SEQUENCE: 20

Met Glu Lys Gly Tyr Ser Thr Val Thr Phe Asp Gly Thr Pro Ser Tyr
 1               5                  10                  15

Gly His Thr Pro Ser His His Ala Ala Gln Phe Pro Asn His Ser Phe
            20                  25                  30

Lys His Glu Asp Pro Met Gly Gln Gln Gly Ser Leu Gly Glu Gln Gln
        35                  40                  45

Tyr Ser Val Pro Pro Pro Val Tyr Gly Cys His Thr Pro Thr Asp Ser
    50                  55                  60

Cys Thr Gly Ser Gln Ala Leu Leu Leu Arg Thr Pro Tyr Ser Ser Asp
65                  70                  75                  80

Asn Leu Tyr Gln Met Thr Ser Gln Leu Glu Cys Met Thr Trp Asn Gln
                85                  90                  95

Met Asn Leu Gly Ala Thr Leu Lys Gly Val Ala Ala Gly Ser Ser Ser
            100                 105                 110

Ser Val Lys Trp Thr Glu Gly Gln Ser Asn His Ser Thr Gly Tyr Glu
        115                 120                 125

Ser Asp Asn His Thr Thr Pro Ile Leu Cys Gly Ala Gln Tyr Arg Ile
    130                 135                 140

His Thr His Gly Val Phe Arg Gly Ile Gln Asp Val Arg Arg Val Pro
145                 150                 155                 160

Gly Val Ala Pro Thr Leu Val Arg Ser Ala Ser Glu Thr Ser Glu Lys
                165                 170                 175

Arg Pro Phe Met Cys Ala Tyr Pro Gly Cys Asn Lys Arg Tyr Phe Lys
            180                 185                 190

Leu Ser His Leu Gln Met His Ser Arg Lys His Thr Gly Glu Lys Pro
        195                 200                 205

Tyr Gln Cys Asp Phe Lys Asp Cys Glu Arg Arg Phe Ser Arg Ser Asp
    210                 215                 220

Gln Leu Lys Arg His Gln Arg Arg His Thr Gly Val Lys Pro Phe Gln
225                 230                 235                 240

Cys Lys Thr Cys Gln Arg Lys Phe Ser Arg Ser Asp His Leu Lys Thr
```

```
                245                 250                 255

His Thr Arg Thr His Thr Gly Glu Lys Pro Phe Ser Cys Arg Trp Pro
            260                 265                 270

Ser Cys Gln Lys Lys Phe Ala Arg Ser Asp Glu Leu Val Arg His His
        275                 280                 285

Asn Met His Gln Arg Asn Met Thr Lys Leu Gln Leu Ala Leu
    290                 295                 300


<210> SEQ ID NO 21
<211> LENGTH: 3092
<212> TYPE: DNA
<213> ORGANISM: Mus musculus

<400> SEQUENCE: 21

tgtgtgaatg gagcggccga gcatcctggc tcctcctcct tccctgctgc cggcccctct      60

tatttgagct ttgggaagct gggggcagcc aggcagctgg ggtaaggagt tcaaggcagc     120

gcccacaccc ggggctctcc gcaacccgac cgcctgcctg ctccccctttt ccttttcccg     180

ccctccctcc cacccactca ttcacccacc cacccagaga gaggacggca gcccaggaac     240

ccgggcccgc cgcctcctcg ccgcgatcct ggacttcctc ctgtcgcagg agccggcttc     300

cacgtgtgtc ccggagccgg cgtctcagca cacgctccgc cgggagcccg ggtgcgtcca     360

gcagccggag caacctgggg accgaggccc ccggagcgcc tgggccaagt ccagcgccga     420

gaatccgcag gatcgcagga gcggagaacc gtccgcatcc gagccgcacc tcatgggttc     480

cgacgtgcgg gacctgaacg cgctgctgcc cgctgtgtct tcgctgggcg gcggcggcgg     540

cggctgcggg ctccctgtga gcggcgcagc gcagtgggcg cccgtgttgg acttcgcgcc     600

tccgggcgcc tcggcttacg ggtcgctggg cggtcccgcg cctcctcccg ctccgccgcc     660

gcctccgccg ccaccccact ccttcatcaa acaggagccc agctggggcg gcgccgagcc     720

acacgaggag cagtgcctga gcgccttcac cttgcacttc tcgggccagt tcaccggtac     780

agccggggcc tgtcgctacg gacccttcgg tcctcccccg cccagccagg cgtcctcggg     840

ccaggccagg atgttcccca atgcgcccta cctgcccagc tgcctggaga gccagcctac     900

catccgcaac caaggataca gcacggtcac tttcgacggg gcgcccagct atggccacac     960

gccctcgcat cacgcggcgc agttccccaa ccattccttc aaacacgagg accccatggg    1020

ccagcagggc tcgctgggcg agcagcagta ctccgtgcca cctccggtgt atggctgcca    1080

cacccctact gacagttgca caggcagcca ggccctgctc ctgaggacgc cctacagcag    1140

tgacaattta taccaaatga cctcccagct tgaatgcatg acctggaatc agatgaacct    1200

aggagctacc ttaaagggaa tggctgctgg gagctccagc tcagtgaaat ggacagaagg    1260

gcagagcaac cacggcacag ggtatgagag tgagaaccac acggccccca tcctctgtgg    1320

tgcccagtac agaatacaca cccacggggt cttccgaggc attcaggatg tgcggcgtgt    1380

atctggagtg gccccaactc ttgtccggtc agcatctgaa accagtgaga aacgtccttt    1440

catgtgtgca tacccaggct gcaataagag atattttaag ctgtcccact tacagatgca    1500

tagccggaag cacactggtg agaaaccata ccagtgtgac ttcaaggact gcgagagaag    1560

gttttctcgc tcagaccagc tcaaaagaca ccaaaggaga cacacaggtg tgaaaccatt    1620

ccagtgtaaa acttgtcagc gaaagttttc ccggtccgac catctgaaga cccacaccag    1680

gactcataca ggtaaaacaa gtgaaaagcc cttcagctgt cggtggcaca gttgtcagaa    1740

aaagtttgcg cgctcagacg aattggtccg ccatcacaac atgcatcaga gaaacatgac    1800
```

```
caaactccag ctggcgcttt gaggggtccg acacggagac agtccagcat cccaggcagg   1860
aaagtgtgca aactgcttcc aaatctgatt ttgaaattcc tcccactcac ctttcaaagg   1920
acacgactgt ggatctacat ccgacttcca agacagcaca cctgattgac tgcatcctat   1980
caggtttgcc ggaaggagtc ggtgctccgc ccacttttga ttaactcaca ggcctgaaaa   2040
aagtggttca cggtgtctag aaagtccatt gctattgtct gaattttcta ctgttagaag   2100
aaccattgtt gataatgccc cccgcccccc cccccgggtt tcctcttctc ctttgtgatc   2160
atttccccag gattagagag actgttacat tttctttcat gggatattta taggccaggg   2220
catgtgtatg tgcctgctaa tgtaaactct gtcatagttc ccatttacta actgccctag   2280
aaagaaataa atcagagagc aaggcaccag gggcaagaat cgtgcagaat ttcagaggtc   2340
tggctgcaaa cctggaaacc tggaaggcca gatgtaattc tacaggcgat tgttaaagct   2400
cataggtttt gagtaactgc atagtaggtt ggtattaact agaactcctg tatagttagg   2460
acagagagga gccttcctgc tcagctattc actctgaaca ctagcactgg gctcttaaga   2520
aatgatgttt taagagcaga gatctttttt taatgtcttt gatttatttt ttagttgtaa   2580
ttaggtacat cctcagagat gtactttcct cctcttgtgc aggatgtgga ggactcagtt   2640
ccatcatctg ggcatcttt agagtgtata gaccacactg gttatgtggc ttcaagttgt   2700
aaaaattaaa atgactttaa aagaaactag gggctggtcc aggatcttca ctggtaagac   2760
tgttcttaag taacttaagt atctttgaat ctgcaagtat gtagggaaaa aaaaaagata   2820
tattattgtg aggaaatcca ttgtttaaag gtgtgcgtgt gttgttgttg ttttttaaag   2880
ggagggagtt tattatttac tgtagcttga aatactgtgt aaatatatat gtatatatat   2940
gatgtgctct ttgtcaacta aaattaggag gtgtatggta ttagctgcat cactgtgtgg   3000
atgtcaatct tacagtgtat tgatgataat actaaaaatg taacctgcat ctttttccac   3060
ttggctgtca attaaagtct attcaaaagg aa                                 3092
```

<210> SEQ ID NO 22
<211> LENGTH: 517
<212> TYPE: PRT
<213> ORGANISM: Mus musculus

<400> SEQUENCE: 22

```
Met Asp Phe Leu Leu Ser Gln Glu Pro Ala Ser Thr Cys Val Pro Glu
 1               5                  10                  15

Pro Ala Ser Gln His Thr Leu Arg Arg Glu Pro Gly Cys Val Gln Gln
            20                  25                  30

Pro Glu Gln Pro Gly Asp Arg Gly Pro Arg Ser Ala Trp Ala Lys Ser
        35                  40                  45

Ser Ala Glu Asn Pro Gln Asp Arg Arg Ser Gly Glu Pro Ser Ala Ser
    50                  55                  60

Glu Pro His Leu Met Gly Ser Asp Val Arg Asp Leu Asn Ala Leu Leu
65                  70                  75                  80

Pro Ala Val Ser Ser Leu Gly Gly Gly Gly Gly Gly Cys Gly Leu Pro
                85                  90                  95

Val Ser Gly Ala Ala Gln Trp Ala Pro Val Leu Asp Phe Ala Pro Pro
            100                 105                 110

Gly Ala Ser Ala Tyr Gly Ser Leu Gly Gly Pro Ala Pro Pro Pro Ala
        115                 120                 125

Pro Pro Pro Pro Pro Pro Pro Pro His Ser Phe Ile Lys Gln Glu Pro
    130                 135                 140
```

```
Ser Trp Gly Gly Ala Glu Pro His Glu Glu Gln Cys Leu Ser Ala Phe
145                 150                 155                 160

Thr Leu His Phe Ser Gly Gln Phe Thr Gly Thr Ala Gly Ala Cys Arg
                165                 170                 175

Tyr Gly Pro Phe Gly Pro Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Thr Ile Arg Asn Gln Gly Tyr Ser Thr Val Thr Phe Asp Gly
    210                 215                 220

Ala Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly Met Ala Ala
305                 310                 315                 320

Gly Ser Ser Ser Ser Val Lys Trp Thr Glu Gly Gln Ser Asn His Gly
                325                 330                 335

Thr Gly Tyr Glu Ser Glu Asn His Thr Ala Pro Ile Leu Cys Gly Ala
            340                 345                 350

Gln Tyr Arg Ile His Thr His Gly Val Phe Arg Gly Ile Gln Asp Val
        355                 360                 365

Arg Arg Val Ser Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
            420                 425                 430

Ser Arg Ser Asp Gln Leu Lys Arg His Gln Arg Arg His Thr Gly Val
        435                 440                 445

Lys Pro Phe Gln Cys Lys Thr Cys Gln Arg Lys Phe Ser Arg Ser Asp
    450                 455                 460

His Leu Lys Thr His Thr Arg Thr His Thr Gly Lys Thr Ser Glu Lys
465                 470                 475                 480

Pro Phe Ser Cys Arg Trp His Ser Cys Gln Lys Lys Phe Ala Arg Ser
                485                 490                 495

Asp Glu Leu Val Arg His His Asn Met His Gln Arg Asn Met Thr Lys
            500                 505                 510

Leu Gln Leu Ala Leu
        515
```

```
<210> SEQ ID NO 23
<211> LENGTH: 2126
<212> TYPE: DNA
<213> ORGANISM: Homo sapiens

<400> SEQUENCE: 23
```

```
gccaggctct ccaccccac ttcccaattg aggaaaccga ggcagaggag gctcagagag      60
ctaccggtgg acccacggtg cctccctccc tgggatctac acagaccatg gccttgccaa     120
cggctcgacc cctgttgggg tcctgtggga cccccgccct cggcagcctc ctgttcctgc     180
tcttcagcct cggatgggtg cagccctcga ggaccctggc tggagagaca gggcaggagg     240
ctgcgcccct ggacggagtc ctggccaacc cacctaacat ttccagcctc tcccctcgcc     300
aactccttgg cttcccgtgt gcggaggtgt ccggcctgag cacggagcgt gtccgggagc     360
tggctgtggc cttggcacag aagaatgtca agctctcaac agagcagctg cgctgtctgg     420
ctcaccggct ctctgagccc cccgaggacc tggacgccct cccattggac ctgctgctat     480
tcctcaaccc agatgcgttc tcggggcccc aggcctgcac ccgtttcttc tcccgcatca     540
cgaaggccaa tgtggacctg ctcccgaggg gggctcccga gcgacagcgg ctgctgcctg     600
cggctctggc ctgctggggt gtgcgggggt ctctgctgag cgaggctgat gtgcgggctc     660
tgggaggcct ggcttgcgac ctgcctgggc gctttgtggc cgagtcggcc gaagtgctgc     720
taccccggct ggtgagctgc ccgggacccc tggaccagga ccagcaggag gcagccaggg     780
cggctctgca gggcggggga cccccctacg gccccccgtc gacatggtct gtctccacga     840
tggacgctct gcggggcctg ctgcccgtgc tgggccagcc catcatccgc agcatcccgc     900
agggcatcgt ggccgcgtgg cggcaacgct cctctcggga cccatcctgg cggcagcctg     960
aacggaccat cctccggccg cggttccggc gggaagtgga gaagacagcc tgtccttcag    1020
gcaagaaggc ccgcgagata gacgagagcc tcatcttcta caagaagtgg gagctggaag    1080
cctgcgtgga tgcggccctg ctggccaccc agatggaccg cgtgaacgcc atccccttca    1140
cctacgagca gctggacgtc ctaaagcata aactggatga gctctaccca caaggttacc    1200
ccgagtctgt gatccagcac ctgggctacc tcttcctcaa gatgagccct gaggacattc    1260
gcaagtggaa tgtgacgtcc ctggagaccc tgaaggcttt gcttgaagtc aacaaagggc    1320
acgaaatgag tcctcaggtg gccaccctga tcgaccgctt tgtgaaggga aggggccagc    1380
tagacaaaga caccctagac accctgaccg ccttctaccc tgggtacctg tgctccctca    1440
gccccgagga gctgagctcc gtgcccccca gcagcatctg ggcggtcagg ccccaggacc    1500
tggacacgtg tgacccaagg cagctggacg tcctctatcc caaggcccgc cttgctttcc    1560
agaacatgaa cgggtccgaa tacttcgtga agatccagtc cttcctgggt ggggccccca    1620
cggaggattt gaaggcgctc agtcagcaga atgtgagcat ggacttggcc acgttcatga    1680
agctgcggac ggatgcggtg ctgccgttga ctgtggctga ggtgcagaaa cttctgggac    1740
cccacgtgga gggcctgaag gcggaggagc ggcaccgccc ggtgcgggac tggatcctac    1800
ggcagcggca ggacgacctg gacacgctgg ggctggggct acagggcggc atccccaacg    1860
gctacctggt cctagacctc agcatgcaag aggccctctc ggggacgccc tgcctcctag    1920
gacctggacc tgttctcacc gtcctggcac tgctcctagc ctccaccctg gcctgagggc    1980
cccactccct tgctggcccc agccctgctg gggatccccg cctggccagg agcaggcacg    2040
ggtggtcccc gttccacccc aagagaactc gcgctcagta aacgggaaca tgccccctgc    2100
agacacgtaa aaaaaaaaaa aaaaaa                                         2126
```

<210> SEQ ID NO 24
<211> LENGTH: 622
<212> TYPE: PRT
<213> ORGANISM: Homo sapiens

```
<400> SEQUENCE: 24

Met Ala Leu Pro Thr Ala Arg Pro Leu Leu Gly Ser Cys Gly Thr Pro
 1               5                  10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415
```

```
Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620


<210> SEQ ID NO 25
<211> LENGTH: 2187
<212> TYPE: DNA
<213> ORGANISM: Homo sapiens

<400> SEQUENCE: 25

tgccaggctc tccaccccca cttcccaatt gaggaaaccg aggcagagga ggctcagcgc      60

cacgcactcc tctttctgcc tggccggcca ctcccgtctg ctgtgacgcg cggacagaga     120

gctaccggtg gacccacggt gcctccctcc ctgggatcta cacagaccat ggccttgcca     180

acggctcgac ccctgttggg gtcctgtggg acccccgccc tcggcagcct cctgttcctg     240

ctcttcagcc tcggatgggt gcagccctcg aggaccctgg ctggagagac agggcaggag     300

gctgcgcccc tggacggagt cctggccaac ccacctaaca tttccagcct ctcccctcgc     360

caactccttg gcttcccgtg tgcggaggtg tccggcctga gcacggagcg tgtccgggag     420

ctggctgtgg ccttggcaca gaagaatgtc aagctctcaa cagagcagct gcgctgtctg     480

gctcaccggc tctctgagcc ccccgaggac ctggacgccc tcccattgga cctgctgcta     540

ttcctcaacc cagatgcgtt ctcggggccc caggcctgca cccgtttctt ctcccgcatc     600

acgaaggcca atgtggacct gctcccgagg ggggctcccg agcgacagcg gctgctgcct     660

gcggctctgg cctgctgggg tgtgcggggg tctctgctga gcgaggctga tgtgcgggct     720

ctgggaggcc tggcttgcga cctgcctggg cgctttgtgg ccgagtcggc cgaagtgctg     780

ctaccccggc tggtgagctg cccgggaccc ctggaccagg accagcagga ggcagccagg     840

gcggctctgc agggcggggg acccccctac ggcccccggt cgacatggtc tgtctccacg     900

atggacgctc tgcggggcct gctgcccgtg ctgggccagc ccatcatccg cagcatcccg     960
```

```
cagggcatcg tggccgcgtg gcggcaacgc tcctctcggg acccatcctg gcggcagcct   1020

gaacggacca tcctccggcc gcggttccgg cgggaagtgg agaagacagc ctgtccttca   1080

ggcaagaagg cccgcgagat agacgagagc ctcatcttct acaagaagtg ggagctggaa   1140

gcctgcgtgg atgcggccct gctggccacc cagatggacc gcgtgaacgc catccccttc   1200

acctacgagc agctggacgt cctaaagcat aaactggatg agctctaccc acaaggttac   1260

cccgagtctg tgatccagca cctgggctac ctcttcctca agatgagccc tgaggacatt   1320

cgcaagtgga atgtgacgtc cctggagacc ctgaaggctt tgcttgaagt caacaaaggg   1380

cacgaaatga gtcctcaggt ggccaccctg atcgaccgct ttgtgaaggg aaggggccag   1440

ctagacaaag acaccctaga caccctgacc gccttctacc ctgggtacct gtgctccctc   1500

agccccgagg agctgagctc cgtgcccccc agcagcatct gggcggtcag gccccaggac   1560

ctggacacgt gtgacccaag gcagctggac gtcctctatc ccaaggcccg ccttgctttc   1620

cagaacatga acgggtccga atacttcgtg aagatccagt ccttcctggg tggggccccc   1680

acggaggatt tgaaggcgct cagtcagcag aatgtgagca tggacttggc cacgttcatg   1740

aagctgcgga cggatgcggt gctgccgttg actgtggctg aggtgcagaa acttctggga   1800

ccccacgtgg agggcctgaa ggcggaggag cggcaccgcc cggtgcggga ctggatccta   1860

cggcagcggc aggacgacct ggacacgctg gggctggggc tacagggcgg catccccaac   1920

ggctacctgg tcctagacct cagcatgcaa gaggccctct cggggacgcc ctgcctccta   1980

ggacctggac ctgttctcac cgtcctggca ctgctcctag cctccaccct ggcctgaggg   2040

ccccactccc ttgctggccc cagccctgct ggggatcccc gcctggccag gagcaggcac   2100

gggtggtccc cgttccaccc caagagaact cgcgctcagt aaacgggaac atgccccctg   2160

cagacacgta aaaaaaaaaa aaaaaaa                                       2187
```

<210> SEQ ID NO 26
<211> LENGTH: 622
<212> TYPE: PRT
<213> ORGANISM: Homo sapiens

<400> SEQUENCE: 26

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
```

```
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575
```

```
Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620


<210> SEQ ID NO 27
<211> LENGTH: 2154
<212> TYPE: DNA
<213> ORGANISM: Homo sapiens

<400> SEQUENCE: 27

cgccacgcac tcctctttct gcctggccgg ccactcccgt ctgctgtgac gcgcggacag      60

agagctaccg gtggacccac ggtgcctccc tccctgggat ctacacagac catggccttg     120

ccaacggctc gacccctgtt ggggtcctgt gggacccccg ccctcggcag cctcctgttc     180

ctgctcttca gcctcggatg ggtgcagccc tcgaggaccc tggctggaga gacagggcag     240

gaggctgcgc ccctggacgg agtcctggcc aacccaccta acatttccag cctctcccct     300

cgccaactcc ttggcttccc gtgtgcggag gtgtccggcc tgagcacgga gcgtgtccgg     360

gagctggctg tggccttggc acagaagaat gtcaagctct caacagagca gctgcgctgt     420

ctggctcacc ggctctctga gcccccgag gacctggacg ccctcccatt ggacctgctg      480

ctattcctca acccagatgc gttctcgggg ccccaggcct gcacccgttt cttctcccgc     540

atcacgaagg ccaatgtgga cctgctcccg aggggggctc ccgagcgaca gcggctgctg     600

cctgcggctc tggcctgctg gggtgtgcgg gggtctctgc tgagcgaggc tgatgtgcgg     660

gctctgggag gcctggcttg cgacctgcct gggcgctttg tggccgagtc ggccgaagtg     720

ctgctacccc ggctggtgag ctgcccggga cccctggacc aggaccagca ggaggcagcc     780

agggcggctc tgcagggcgg gggacccccc tacggccccc cgtcgacatg gtctgtctcc     840

acgatggacg ctctgcgggg cctgctgccc gtgctgggcc agcccatcat ccgcagcatc     900

ccgcagggca tcgtggccgc gtggcggcaa cgctcctctc gggacccatc ctggcggcag     960

cctgaacgga ccatcctccg gccgcggttc cggcgggaag tggagaagac agcctgtcct    1020

tcaggcaaga aggcccgcga gatagacgag agcctcatct tctacaagaa gtgggagctg    1080

gaagcctgcg tggatgcggc cctgctggcc acccagatgg accgcgtgaa cgccatcccc    1140

ttcacctacg agcagctgga cgtcctaaag cataaactgg atgagctcta cccacaaggt    1200

taccccgagt ctgtgatcca gcacctgggc tacctcttcc tcaagatgag ccctgaggac    1260

attcgcaagt ggaatgtgac gtccctggag accctgaagg ctttgcttga agtcaacaaa    1320

gggcacgaaa tgagtcctca ggctcctcgg cggcccctcc cacaggtggc caccctgatc    1380

gaccgctttg tgaagggaag gggccagcta gacaaagaca ccctagacac cctgaccgcc    1440

ttctaccctg ggtacctgtg ctccctcagc cccgaggagc tgagctccgt gccccccagc    1500

agcatctggg cggtcaggcc ccaggacctg gacacgtgtg acccaaggca gctggacgtc    1560

ctctatccca aggcccgcct tgctttccag aacatgaacg ggtccgaata cttcgtgaag    1620

atccagtcct tcctgggtgg ggcccccacg gaggatttga aggcgctcag tcagcagaat    1680

gtgagcatgg acttggccac gttcatgaag ctgcggacgg atgcggtgct gccgttgact    1740

gtggctgagg tgcagaaact tctgggaccc cacgtggagg gcctgaaggc ggaggagcgg    1800

caccgcccgg tgcgggactg gatcctacgg cagcggcagg acgacctgga cacgctgggg    1860
```

```
ctggggctac agggcggcat ccccaacggc tacctggtcc tagacctcag catgcaagag   1920

gccctctcgg ggacgccctg cctcctagga cctggacctg ttctcaccgt cctggcactg   1980

ctcctagcct ccaccctggc ctgagggccc cactcccttg ctggccccag ccctgctggg   2040

gatccccgcc tggccaggag caggcacggg tggtccccgt tccaccccaa gagaactcgc   2100

gctcagtaaa cgggaacatg ccccctgcag acacgtaaaa aaaaaaaaaa aaaa         2154


<210> SEQ ID NO 28
<211> LENGTH: 630
<212> TYPE: PRT
<213> ORGANISM: Homo sapiens

<400> SEQUENCE: 28

Met Ala Leu Pro Thr Ala Arg Pro Leu Leu Gly Ser Cys Gly Thr Pro
 1               5                  10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320
```

```
Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630
```

<210> SEQ ID NO 29
<211> LENGTH: 2135
<212> TYPE: DNA
<213> ORGANISM: Mus musculus

<400> SEQUENCE: 29

```
ggacagctgc tttcccaggc ccaaaagccc cttcgttgtc tccaaacagt ggtgtgggtt      60

gaggggtggg acaagtgggg acctcagagt cattgttatc cacagaccat ggccttgcca     120

acagctcgac ccctgctggg gtcctgtgga agtcccatct gcagccgaag cttcctactg     180

cttctcctta gtcttgggtg gataccacgt ctgcagaccc agactacaaa gacaagccag     240

gaggccacac tcctccatgc tgtgaacggt gccgctgact ttgccagtct ccccacaggc     300

ctctttcttg gcctcacatg tgaggaggta tctgacctga gcatggaaca agccaagggg     360
```

```
ctggctatgg ctgtaagaca gaagaacatt acactccggg gacatcagct gcgttgtctg    420

gcacgtcgcc ttcctaggca cctcaccgac gaggaactga atgctcttcc actggacctg    480

ctgctcttcc tcaacccagc catgtttcca gggcaacagg cttgtgccca cttcttctcc    540

ctcatctcta aagccaatgt ggatgtactc ccacggaggt ctctggagcg ccagaggctg    600

ctgatggagg ctctgaagtg ccagggcgtg tatggatttc aagtgagtga ggcagatgtg    660

cgggctctcg gaggcctggc ctgtgacctg cctgggaaat ttgtggccag atcttccgaa    720

gttctcctcc cctggctggc aggatgccaa ggacccctgg accagagcca ggaaaaggca    780

gtcagggagg ttctgaggag tggaagaacc caatatggcc ccccatcgaa gtggtcagtc    840

tccaccctgg atgccctgca gagcttggta gcagtgttgg atgagtccat cgtccagagc    900

atccccaagg atgtcaaagc tgaatggctg caacacatct ccagagaccc ctccaggctg    960

gggtctaagc tgaccgtcat acacccaagg ttccgacggg atgcagaaca gaaagcctgc   1020

cctccaggga aggagcccta caaggtggat gaagacctca tcttctacca gaattgggag   1080

ctggaggctt gtgtagatgg caccatgctg gccagacaaa tggaccttgt gaacgagatt   1140

cccttcacct atgagcagct cagtatcttt aagcacaaac tggacaagac ctacccacaa   1200

ggctatcctg agtccctgat ccagcagctg ggtcacttct tcagatatgt tagccctgaa   1260

gacatccacc agtggaatgt gacctcacca gacacagtga aaactctgct caaagtcagc   1320

aaaggacaaa agatgaatgc tcaggcgatt gccttggtcg cctgctatct tcggggagga   1380

ggccagctgg acgaggatat ggtaaaagcc ctgggcgaca tcccgttaag ctatctatgt   1440

gacttcagcc cccaggatct gcactcggta ccctccagtg tcatgtggct ggttgggccc   1500

caagacctgg acaagtgcag ccagaggcat ctgggtctcc tctaccagaa ggcctgctca   1560

gccttccaga atgtgagcgg cctagaatac tttgagaaaa tcaagacatt cctgggtggg   1620

gcctccgtga aggacctgcg ggccctcagc cagcacaatg tgagcatgga catagccact   1680

ttcaagaggc tgcaggtgga ttccctggtg gggctgagtg tggctgaggt acagaaactt   1740

ctggggccaa acattgtgga cctgaagacc gaggaggata aaagccctgt ccgtgactgg   1800

ctgttccggc agcatcagaa agacctagac aggctgggtt tgggacttca gggtggcatc   1860

cccaatggct acctggtcct ggacttcaat gtccgagagg ccttctccag cagagcctca   1920

ctccttgggc caggatttgt attaatatgg attccagctc tgctcccagc tttaaggctg   1980

agctgagacc accaccctgc aaggctcctg gtcccagctc tactggggcc ctcttgacca   2040

ggagtgggta ccaggggtca ttgccaaagt ttgaggactc ttgaactcaa taaacagtgg   2100

catatgctcc cttgaaaaaa aaaaaaaaaa aaaaa                              2135
```

<210> SEQ ID NO 30
<211> LENGTH: 625
<212> TYPE: PRT
<213> ORGANISM: Mus musculus

<400> SEQUENCE: 30

```
Met Ala Leu Pro Thr Ala Arg Pro Leu Leu Gly Ser Cys Gly Ser Pro
 1               5                  10                  15

Ile Cys Ser Arg Ser Phe Leu Leu Leu Leu Leu Ser Leu Gly Trp Ile
            20                  25                  30

Pro Arg Leu Gln Thr Gln Thr Thr Lys Thr Ser Gln Glu Ala Thr Leu
        35                  40                  45

Leu His Ala Val Asn Gly Ala Ala Asp Phe Ala Ser Leu Pro Thr Gly
```

```
    50                  55                  60

Leu Phe Leu Gly Leu Thr Cys Glu Glu Val Ser Asp Leu Ser Met Glu
65                  70                  75                  80

Gln Ala Lys Gly Leu Ala Met Ala Val Arg Gln Lys Asn Ile Thr Leu
                85                  90                  95

Arg Gly His Gln Leu Arg Cys Leu Ala Arg Arg Leu Pro Arg His Leu
            100                 105                 110

Thr Asp Glu Glu Leu Asn Ala Leu Pro Leu Asp Leu Leu Leu Phe Leu
        115                 120                 125

Asn Pro Ala Met Phe Pro Gly Gln Gln Ala Cys Ala His Phe Phe Ser
    130                 135                 140

Leu Ile Ser Lys Ala Asn Val Asp Val Leu Pro Arg Arg Ser Leu Glu
145                 150                 155                 160

Arg Gln Arg Leu Leu Met Glu Ala Leu Lys Cys Gln Gly Val Tyr Gly
                165                 170                 175

Phe Gln Val Ser Glu Ala Asp Val Arg Ala Leu Gly Gly Leu Ala Cys
            180                 185                 190

Asp Leu Pro Gly Lys Phe Val Ala Arg Ser Ser Glu Val Leu Leu Pro
        195                 200                 205

Trp Leu Ala Gly Cys Gln Gly Pro Leu Asp Gln Ser Gln Glu Lys Ala
    210                 215                 220

Val Arg Glu Val Leu Arg Ser Gly Arg Thr Gln Tyr Gly Pro Pro Ser
225                 230                 235                 240

Lys Trp Ser Val Ser Thr Leu Asp Ala Leu Gln Ser Leu Val Ala Val
                245                 250                 255

Leu Asp Glu Ser Ile Val Gln Ser Ile Pro Lys Asp Val Lys Ala Glu
            260                 265                 270

Trp Leu Gln His Ile Ser Arg Asp Pro Ser Arg Leu Gly Ser Lys Leu
        275                 280                 285

Thr Val Ile His Pro Arg Phe Arg Arg Asp Ala Glu Gln Lys Ala Cys
    290                 295                 300

Pro Pro Gly Lys Glu Pro Tyr Lys Val Asp Glu Asp Leu Ile Phe Tyr
305                 310                 315                 320

Gln Asn Trp Glu Leu Glu Ala Cys Val Asp Gly Thr Met Leu Ala Arg
                325                 330                 335

Gln Met Asp Leu Val Asn Glu Ile Pro Phe Thr Tyr Glu Gln Leu Ser
            340                 345                 350

Ile Phe Lys His Lys Leu Asp Lys Thr Tyr Pro Gln Gly Tyr Pro Glu
        355                 360                 365

Ser Leu Ile Gln Gln Leu Gly His Phe Phe Arg Tyr Val Ser Pro Glu
    370                 375                 380

Asp Ile His Gln Trp Asn Val Thr Ser Pro Asp Thr Val Lys Thr Leu
385                 390                 395                 400

Leu Lys Val Ser Lys Gly Gln Lys Met Asn Ala Gln Ala Ile Ala Leu
                405                 410                 415

Val Ala Cys Tyr Leu Arg Gly Gly Gly Gln Leu Asp Glu Asp Met Val
            420                 425                 430

Lys Ala Leu Gly Asp Ile Pro Leu Ser Tyr Leu Cys Asp Phe Ser Pro
        435                 440                 445

Gln Asp Leu His Ser Val Pro Ser Ser Val Met Trp Leu Val Gly Pro
    450                 455                 460

Gln Asp Leu Asp Lys Cys Ser Gln Arg His Leu Gly Leu Leu Tyr Gln
465                 470                 475                 480
```

```
Lys Ala Cys Ser Ala Phe Gln Asn Val Ser Gly Leu Glu Tyr Phe Glu
                485                 490                 495

Lys Ile Lys Thr Phe Leu Gly Gly Ala Ser Val Lys Asp Leu Arg Ala
            500                 505                 510

Leu Ser Gln His Asn Val Ser Met Asp Ile Ala Thr Phe Lys Arg Leu
        515                 520                 525

Gln Val Asp Ser Leu Val Gly Leu Ser Val Ala Glu Val Gln Lys Leu
    530                 535                 540

Leu Gly Pro Asn Ile Val Asp Leu Lys Thr Glu Glu Asp Lys Ser Pro
545                 550                 555                 560

Val Arg Asp Trp Leu Phe Arg Gln His Gln Lys Asp Leu Asp Arg Leu
                565                 570                 575

Gly Leu Gly Leu Gln Gly Gly Ile Pro Asn Gly Tyr Leu Val Leu Asp
            580                 585                 590

Phe Asn Val Arg Glu Ala Phe Ser Ser Arg Ala Ser Leu Leu Gly Pro
        595                 600                 605

Gly Phe Val Leu Ile Trp Ile Pro Ala Leu Leu Pro Ala Leu Arg Leu
    610                 615                 620

Ser
625


<210> SEQ ID NO 31
<211> LENGTH: 9
<212> TYPE: PRT
<213> ORGANISM: Artificial Sequence
<220> FEATURE:
<223> OTHER INFORMATION: Synthetic mesothelin peptide

<400> SEQUENCE: 31

Gly Gln Lys Met Asn Ala Gln Ala Ile
 1               5


<210> SEQ ID NO 32
<211> LENGTH: 15
<212> TYPE: PRT
<213> ORGANISM: Artificial Sequence
<220> FEATURE:
<223> OTHER INFORMATION: 3D beta peptide clone from Mus musculus

<400> SEQUENCE: 32

Cys Ala Ser Ser Pro Gly Leu Gly Gly Ser Tyr Glu Gln Tyr Phe
 1               5                  10                  15


<210> SEQ ID NO 33
<211> LENGTH: 45
<212> TYPE: DNA
<213> ORGANISM: Artificial Sequence
<220> FEATURE:
<223> OTHER INFORMATION: 3D beta nucleotide clone from Mus musculus

<400> SEQUENCE: 33

tgtgccagca gccctggact ggggggatcc tatgaacagt acttc                    45


<210> SEQ ID NO 34
<211> LENGTH: 15
<212> TYPE: PRT
<213> ORGANISM: Artificial Sequence
<220> FEATURE:
<223> OTHER INFORMATION: V beta 10 clone #1 peptide clone from Mus
      musculus

<400> SEQUENCE: 34
```

```
Cys Ala Ser Ser Gln Gly Leu Gly Ser Ser Tyr Glu Gln Tyr Phe
 1              5                   10                  15


<210> SEQ ID NO 35
<211> LENGTH: 45
<212> TYPE: DNA
<213> ORGANISM: Artificial Sequence
<220> FEATURE:
<223> OTHER INFORMATION: V beta 10 clone #1 nucleotide clone from Mus
      musculus

<400> SEQUENCE: 35

tgtgccagca gccagggact ggggagctcc tatgaacagt acttc                    45


<210> SEQ ID NO 36
<211> LENGTH: 14
<212> TYPE: PRT
<213> ORGANISM: Artificial Sequence
<220> FEATURE:
<223> OTHER INFORMATION: V beta 10 clone #2 peptide from Mus musculus

<400> SEQUENCE: 36

Cys Ala Ser Ser Tyr Ile Leu Gly Ala Tyr Glu Gln Tyr Phe
 1              5                   10


<210> SEQ ID NO 37
<211> LENGTH: 42
<212> TYPE: DNA
<213> ORGANISM: Artificial Sequence
<220> FEATURE:
<223> OTHER INFORMATION: V beta 10 clone #2 nucleotide from Mus musculus

<400> SEQUENCE: 37

tgtgccagca gctatatact gggggcctat gaacagtact tc                       42


<210> SEQ ID NO 38
<211> LENGTH: 13
<212> TYPE: PRT
<213> ORGANISM: Artificial Sequence
<220> FEATURE:
<223> OTHER INFORMATION: V beta 10 clone #3 peptide from Mus musculus

<400> SEQUENCE: 38

Cys Ala Ser Ser Ser Trp Thr Val Tyr Glu Gln Tyr Phe
 1              5                   10


<210> SEQ ID NO 39
<211> LENGTH: 39
<212> TYPE: DNA
<213> ORGANISM: Artificial Sequence
<220> FEATURE:
<223> OTHER INFORMATION: V beta 10 clone #3 nucleotide from Mus musculus

<400> SEQUENCE: 39

tgtgccagca gctcctggac agtctatgaa cagtacttc                           39


<210> SEQ ID NO 40
<211> LENGTH: 15
<212> TYPE: PRT
<213> ORGANISM: Artificial Sequence
<220> FEATURE:
<223> OTHER INFORMATION: V beta 10 clone #4 peptide from Mus musculus

<400> SEQUENCE: 40

Cys Ala Ser Ser Trp Thr Gly Ala Asn Thr Gly Gln Leu Tyr Phe
 1              5                   10                  15
```

<210> SEQ ID NO 41
<211> LENGTH: 45
<212> TYPE: DNA
<213> ORGANISM: Artificial Sequence
<220> FEATURE:
<223> OTHER INFORMATION: V beta 10 clone #4 nucleotide from Mus musculus

<400> SEQUENCE: 41
tgtgccagca gctggacagg ggcaaacacc gggcagctct acttt 45

<210> SEQ ID NO 42
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 42

Ile Ser Lys Ala Asn Val Asp Val Leu
1 5

<210> SEQ ID NO 43
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 43

Gly Gln Lys Met Asn Ala Gln Ala Ile
1 5

<210> SEQ ID NO 44
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 44

Ser Ala Phe Gln Asn Val Ser Gly Leu
1 5

<210> SEQ ID NO 45
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 45

Leu Leu Gly Pro Asn Ile Val Asp Leu
1 5

<210> SEQ ID NO 46
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 46

Glu Ile Pro Phe Thr Tyr Glu Gln Leu
1 5

<210> SEQ ID NO 47
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 47

Gly Ile Pro Asn Gly Tyr Leu Val Leu
1 5

<210> SEQ ID NO 48
<211> LENGTH: 1595
<212> TYPE: DNA
<213> ORGANISM: Homo sapiens

<400> SEQUENCE: 48

```
agaatcaaaa gaggaaacca acccctaaga tgagctttcc atgtaaattt gtagccagct     60

tccttctgat tttcaatgtt tcttccaaag gtgcagtctc caaagagatt acgaatgcct    120

tggaaacctg ggtgccttg ggtcaggaca tcaacttgga cattcctagt tttcaaatga    180

gtgatgatat tgacgatata aaatgggaaa aaacttcaga caagaaaaag attgcacaat    240

tcagaaaaga gaaagagact ttcaaggaaa aagatacata taagctattt aaaaatggaa    300

ctctgaaaat taagcatctg aagaccgatg atcaggatat ctacaaggta tcaatatatg    360

atacaaaagg aaaaaatgtg ttggaaaaaa tatttgattt gaagattcaa gagagggtct    420

caaaaccaaa gatctcctgg acttgtatca acacaaccct gacctgtgag gtaatgaatg    480

gaactgaccc cgaattaaac ctgtatcaag atgggaaaca tctaaaactt tctcagaggg    540

tcatcacaca caagtggacc accagcctga gtgcaaaatt caagtgcaca gcagggaaca    600

aagtcagcaa ggaatccagt gtcgagcctg tcagctgtcc agagaaaggt ctggacatct    660

atctcatcat tggcatatgt ggaggaggca gcctcttgat ggtctttgtg gcactgctcg    720

ttttctatat caccaaaagg aaaaaacaga ggagtcggag aaatgatgag gagctggaga    780

caagagccca cagagtagct actgaagaaa ggggccggaa gccccaccaa attccagctt    840

caacccctca gaatccagca acttcccaac atcctcctcc accacctggt catcgttccc    900

aggcacctag tcatcgtccc ccgcctcctg gacaccgtgt tcagcaccag cctcagaaga    960

ggcctcctgc tccgtcgggc acacaagttc accagcagaa aggcccgccc ctccccagac   1020

ctcgagttca gccaaaacct ccccatgggg cagcagaaaa ctcattgtcc ccttcctcta   1080

attaaaaaag atagaaactg tctttttcaa taaaaagcac tgtggatttc tgccctcctg   1140

atgtgcatat ccgtacttcc atgaggtgtt ttctgtgtgc agaacattgt cacctcctga   1200

ggctgtgggc cacagccacc tctgcatctt cgaactcagc catgtggtca acatctggag   1260

tttttggtct cctcagagag ctccatcaca ccagtaagga gaagcaatat aagtgtgatt   1320

gcaagaatgg tagaggaccg agcacagaaa tcttagagat ttcttgtccc ctctcaggtc   1380

atgtgtagat gcgataaatc aagtgattgg tgtgcctggg tctcactaca agcagcctat   1440

ctgcttaaga gactctggag tttcttatgt gccctggtgg acacttgccc accatcctgt   1500

gagtaaaagt gaaataaaag ctttgactag aaaaaaaaaa aaaaaaaaaa aaaaaaaaaa   1560

aaaaaaaaaa aaaaaaaaaa aaaaaaaaaa aaaaa                             1595
```

<210> SEQ ID NO 49
<211> LENGTH: 351
<212> TYPE: PRT
<213> ORGANISM: Homo sapiens

<400> SEQUENCE: 49

```
Met Ser Phe Pro Cys Lys Phe Val Ala Ser Phe Leu Leu Ile Phe Asn
 1               5                  10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp Ile Tyr Leu Ile Ile Gly Ile Cys Gly Gly Gly Ser Leu Leu Met
    210                 215                 220

Val Phe Val Ala Leu Leu Val Phe Tyr Ile Thr Lys Arg Lys Lys Gln
225                 230                 235                 240

Arg Ser Arg Arg Asn Asp Glu Glu Leu Glu Thr Arg Ala His Arg Val
                245                 250                 255

Ala Thr Glu Glu Arg Gly Arg Lys Pro His Gln Ile Pro Ala Ser Thr
            260                 265                 270

Pro Gln Asn Pro Ala Thr Ser Gln His Pro Pro Pro Pro Pro Gly His
        275                 280                 285

Arg Ser Gln Ala Pro Ser His Arg Pro Pro Pro Pro Gly His Arg Val
    290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
                325                 330                 335

Pro Pro His Gly Ala Ala Glu Asn Ser Leu Ser Pro Ser Ser Asn
            340                 345                 350
```

<210> SEQ ID NO 50
<211> LENGTH: 1098
<212> TYPE: DNA
<213> ORGANISM: Homo sapiens

<400> SEQUENCE: 50

```
atggccgtca tggctccccg aaccctcgtc ctgctactct cgggggctct ggccctgacc      60
```

```
cagacctggg cgggctctca ctccatgagg tatttcttca catccgtgtc ccggcccggc    120

cgcggggagc cccgcttcat cgcagtgggc tacgtggacg acacgcagtt cgtgcggttc    180

gacagcgacg ccgcgagcca gaggatggag ccgcgggcgc cgtggataga gcaggagggt    240

ccggagtatt gggacgggga gacacggaaa gtgaaggccc actcacagac tcaccgagtg    300

gacctgggga ccctgcgcgg ctactacaac cagagcgagg ccggttctca caccctccag    360

atgatgtttg gctgcgacgt ggggtcggac tggcgcttcc tccgcgggta ccaccagtac    420

gcctacgacg gcaaggatta catcgccctg aaagaggacc tgcgctcttg gaccgcggcg    480

gacatggcag ctcagaccac caagcacaag tgggaggcgg cccatgtggc ggagcagttg    540

agagcctacc tggagggcac gtgcgtggag tggctccgca gatacctgga gaacgggaag    600

gagacgctgc agcgcacgga cgcccccaaa acgcatatga ctcaccacgc tgtctctgac    660

catgaagcca ccctgaggtg ctgggccctg agcttctacc ctgcggagat cacactgacc    720

tggcagcggg atggggagga ccagacccag gacacggagc tcgtggagac caggcctgca    780

ggggatggaa ccttccagaa gtgggcggct gtggtggtgc cttctggaca ggagcagaga    840

tacacctgcc atgtgcagca tgagggtttg cccaagcccc tcaccctgag atgggagccg    900

tcttcccagc ccaccatccc catcgtgggc atcattgctg gcctggttct ctttggagct    960

gtgatcactg gagctgtggt cgctgctgtg atgtggagga ggaagagctc agatagaaaa   1020

ggagggagct actctcaggc tgcaagcagt gacagtgccc agggctctga tgtgtctctc   1080

acagcttgta aagtgtga                                                 1098
```

<210> SEQ ID NO 51
<211> LENGTH: 365
<212> TYPE: PRT
<213> ORGANISM: Homo sapiens

<400> SEQUENCE: 51

```
Met Ala Val Met Ala Pro Arg Thr Leu Val Leu Leu Leu Ser Gly Ala
 1               5                  10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Leu Gln Met Met Phe Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190
```

```
Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365
```

<210> SEQ ID NO 52
<211> LENGTH: 987
<212> TYPE: DNA
<213> ORGANISM: Homo sapiens

<400> SEQUENCE: 52

```
aatataagtg gaggcgtcgc gctggcgggc attcctgaag ctgacagcat tcgggccgag      60

atgtctcgct ccgtggcctt agctgtgctc gcgctactct ctctttctgg cctggaggct     120

atccagcgta ctccaaagat tcaggtttac tcacgtcatc cagcagagaa tggaaagtca     180

aatttcctga attgctatgt gtctgggttt catccatccg acattgaagt tgacttactg     240

aagaatggag agagaattga aaaagtggag cattcagact tgtctttcag caaggactgg     300

tctttctatc tcttgtacta cactgaattc acccccactg aaaaagatga gtatgcctgc     360

cgtgtgaacc atgtgacttt gtcacagccc aagatagtta agtgggatcg agacatgtaa     420

gcagcatcat ggaggtttga agatgccgca tttggattgg atgaattcca aattctgctt     480

gcttgctttt taatattgat atgcttatac acttacactt tatgcacaaa atgtagggtt     540

ataataatgt taacatggac atgatcttct ttataattct actttgagtg ctgtctccat     600

gtttgatgta tctgagcagg ttgctccaca ggtagctcta ggagggctgg caacttagag     660

gtggggagca gagaattctc ttatccaaca tcaacatctt ggtcagattt gaactcttca     720

atctcttgca ctcaaagctt gttaagatag ttaagcgtgc ataagttaac ttccaattta     780

catactctgc ttagaatttg ggggaaaatt tagaaatata attgacagga ttattggaaa     840

tttgttataa tgaatgaaac attttgtcat ataagattca tatttacttc ttatacattt     900

gataaagtaa ggcatggttg tggttaatct ggtttatttt tgttccacaa gttaaataaa     960

tcataaaact tgatgtgtta tctctta                                         987
```

<210> SEQ ID NO 53
<211> LENGTH: 119

-continued

```
<212> TYPE: PRT
<213> ORGANISM: Homo sapiens

<400> SEQUENCE: 53

Met Ser Arg Ser Val Ala Leu Ala Val Leu Ala Leu Leu Ser Leu Ser
 1               5                  10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115
```